US012017994B2

(12) United States Patent
Tavares et al.

(10) Patent No.: US 12,017,994 B2
(45) Date of Patent: Jun. 25, 2024

(54) COMPOUNDS, COMPOSITIONS, AND METHODS FOR SELECTIVELY INHIBITING β-GLUCURONIDASES AND ALLEVIATING SIDE EFFECTS ASSOCIATED WITH DRUG TREATMENT INDUCED DIARRHEA

(71) Applicant: SYMBERIX, INC., Durham, NC (US)

(72) Inventors: Francis X. Tavares, Durham, NC (US); Bret D. Wallace, Durham, NC (US); Ward Peterson, Morrisville, NC (US)

(73) Assignee: Symberix, Inc., Durham, NC (US)

( * ) Notice: Subject to any disclaimer, the term of this patent is extended or adjusted under 35 U.S.C. 154(b) by 332 days.

(21) Appl. No.: 16/959,491

(22) PCT Filed: Sep. 7, 2018

(86) PCT No.: PCT/US2018/049891
§ 371 (c)(1),
(2) Date: Jul. 1, 2020

(87) PCT Pub. No.: WO2019/051185
PCT Pub. Date: Mar. 14, 2019

(65) Prior Publication Data
US 2021/0094917 A1 Apr. 1, 2021

Related U.S. Application Data

(60) Provisional application No. 62/555,847, filed on Sep. 8, 2017.

(51) Int. Cl.
*C07D 215/227* (2006.01)
*A61K 45/06* (2006.01)
*A61P 1/12* (2006.01)

(52) U.S. Cl.
CPC .......... *C07D 215/227* (2013.01); *A61K 45/06* (2013.01); *A61P 1/12* (2018.01)

(58) Field of Classification Search
None
See application file for complete search history.

(56) References Cited

U.S. PATENT DOCUMENTS

| 2010/0035912 | A1 | 2/2010 | Debnath |
| 2012/0322797 | A1 | 12/2012 | Redlinbo |
| 2014/0107139 | A1 | 4/2014 | Alvaro |

FOREIGN PATENT DOCUMENTS

| WO | 2004/030629 A2 | 4/2004 | |
| WO | 2007/136592 A2 | 11/2007 | |
| WO | WO 2009/128262 A1 * | 10/2009 | ........... C07D 215/22 |
| WO | 2011/072127 A1 | 6/2011 | |
| WO | 2011072127 | 6/2011 | |

OTHER PUBLICATIONS

Wallace et al., Science (2010), vol. 330, pp. 831-835.*
International Search Report dated Jan. 28, 2019 for PCT/US2018/049891.
Pubmed Compound Summary for CID 1138022, 'KYAOCDYAEUCDCP-UHFFFAOYSA-N', U.S. National Library of Medicine, Jul. 10, 2005 (Jul. 10, 2005), pp. 1-11; p. 3 (https://pubchem.ncbi.nlm.nih.gov/compound/1138022).
Pubmed Compound Summary for CID 644672, '1-[3-(Dimethylamino)propyl]-1-((6-methoxy-2-oxo-1H-quinolin-3-yl)methyl-3-phenylurea', U.S. National Library of Medicine, Jun. 4, 2005 (Jun. 4, 2005). pp. 1-14; p. 4 (https://pubchem.ncbi.nlm.nih.gov/compound/644672).
Ahmad, et al., "A high throughput for discovery of bacterial beta-glucuronidase inhibitors", Current Chemical Genomics, (Apr. 2011), vol. 5, pp. 13-20.
Wallace, B.D., et al., "Structure and inhibition of microbiome beta-glucuronidases essential to the alleviation of cancer drug toxicity", Chemistry and Biology (Sep. 2015), vol. 22, No. 9, pp. 1238-1249.
Massai, F., et al., "Development, optimization, and validation of a high throughpubiot screening assay for identification of tat and type II secretion inhibitors of pseudomonas aeruginosa", Frontiers in Cellular and Infection Microbiology (Jul. 2019), vol. 9.
Kishore-Reddy, B.K., et al., "Assessment of *Mycobacterium tuberculosis* pantothenate kinase vulnerability through target knockdown and mechanistically diverse inhibitors", Antimicrobial Agents and Chemotherapy (Jun. 2014), vol. 58, No. 6, pp. 3312-3326.
Anantaraju, et al., "Cathepsin D inhibitors as potential therapeutics for breast cancer treatment: Molecular docking and bioevaluation against triple-negative and triple-positive breast cancers", Molecular Diversity, (Nov. 2015), vol. 20, No. 2, pp. 521-535.
McKay, P.B., et al., "Identification of plasmepsin inhibitors as selective anti-malarial agents using ligand based drug design", Bioorganic & Medicinal Chemistry Letters, (Apr. 2011), vol. 21, No. 11, pp. 3335-3341.
Tintori, C., et al., "Studies on the ATP Binding Site of Fyn Kinase for the Identification of New Inhibitors and Their Evaluation as Potential Agents against Tauopathies and Tumors", Journal of Medicinal Chemistry, (Jun. 2015), vol. 58, No. 11, pp. 4590-4609.
Kaur, M, et al., "Ligand-based and e-pharmacophore modeling, 3D-QSAR and hierarchical virtual screening to identify dual inhibitors of spleen tyrosine kinase (Syk) and janus kinase 3 (JAK3)", Journal of Biomolecular Structure & Dynamics, (Nov. 2016), vol. 35, No. 14, pp. 3043-3060.
Office action from corresponding European Application No. 18854689.9, dated Sep. 3, 2021.
Database Registry [Online] Chemical Abstracts Service, Columbus, Ohio, US; Jan. 31, 2003, XP002805372, Database accession No. 484057-34-3.
Ahmad, et al., A High Throughput Assay for Discovery of Bacterial b-Glucuronidase Inhibitors; Current Chemical Genomics, May 13-20, 2011; North Carolina, USA.

(Continued)

*Primary Examiner* — Brian J Davis
(74) *Attorney, Agent, or Firm* — Barnes & Thornburg LLP; Aisha R. Hasan

(57) ABSTRACT

The present disclosure describes compounds and compositions that inhibit β-glucuronidase activity, and methods for attenuating the side effects of one or more drugs and improving the efficacy of drugs by administration of selective β-glucuronidase inhibitors.

12 Claims, 2 Drawing Sheets

(56) References Cited

OTHER PUBLICATIONS

Wallace, et al., Structure and Inhibition of Microbiome b-Glucuronidases Essential to the Alleviation of Cancer Drug Toxicity; Chemistry & Biology 22, 1238-1249; Sep. 17, 2015; North Carolina, USA.
Office Action dated Jun. 16, 2023—Japanese Patent application No. 2020-568659.
European Search Report for EP 18 85 4689, dated Jan. 21, 2022.
Database Registry [Online] Chemical Abstracts Service, Columbus, Ohio, US; Sep. 30, 2009 (Sep. 30, 2009), XP002805366, Database accession No. 1177947-56-6.
Database Registry [Online] Chemical Abstracts Service, Columbus, Ohio, US; Jan. 31, 2005 (Jan. 31, 2005), XP002805367, Database accession No. 823230-20-2.
Database Registry [Online] Chemical Abstracts Service, Columbus, Ohio, US; Sep. 5, 2003 (Sep. 5, 2003), XP002805368, Database accession No. 579519-29-2.
Database Registry [Online] Chemical Abstracts Service, Columbus, Ohio, US; Jul. 22, 2003 (Jul. 22, 2003), XP002805369, Database accession No. 552311-94-1.
Database Registry [Online] Chemical Abstracts Service, Columbus, Ohio, US; Jul. 21, 2003 (Jul. 21, 2003), XP002805370, Database accession No. 551931-47-6.
Database Registry [Online] Chemical Abstracts Service, Columbus, Ohio, US; May 16, 2003 (May 16, 2003), XP002805371, Database accession No. 516476-45-2.

\* cited by examiner

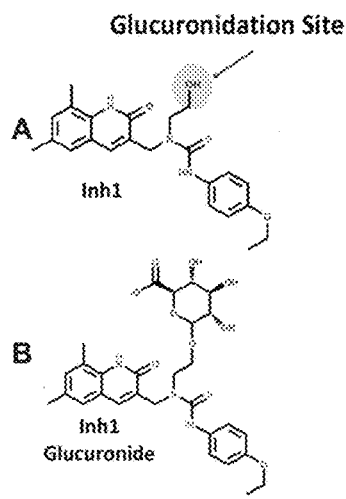

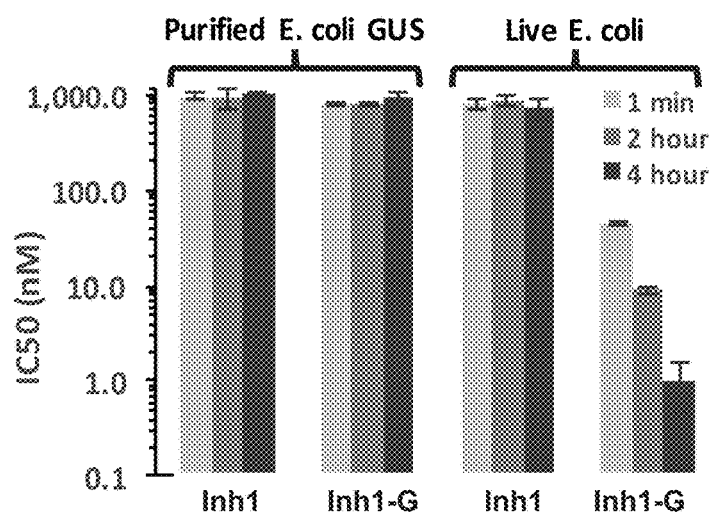

Figure 1: Structure of Inh1 and Inh1 glucuronide (Inh1-G)

Figure 2: Bar graphs summarizing the $IC_{50}$'s of Inh1 and Inh1-G

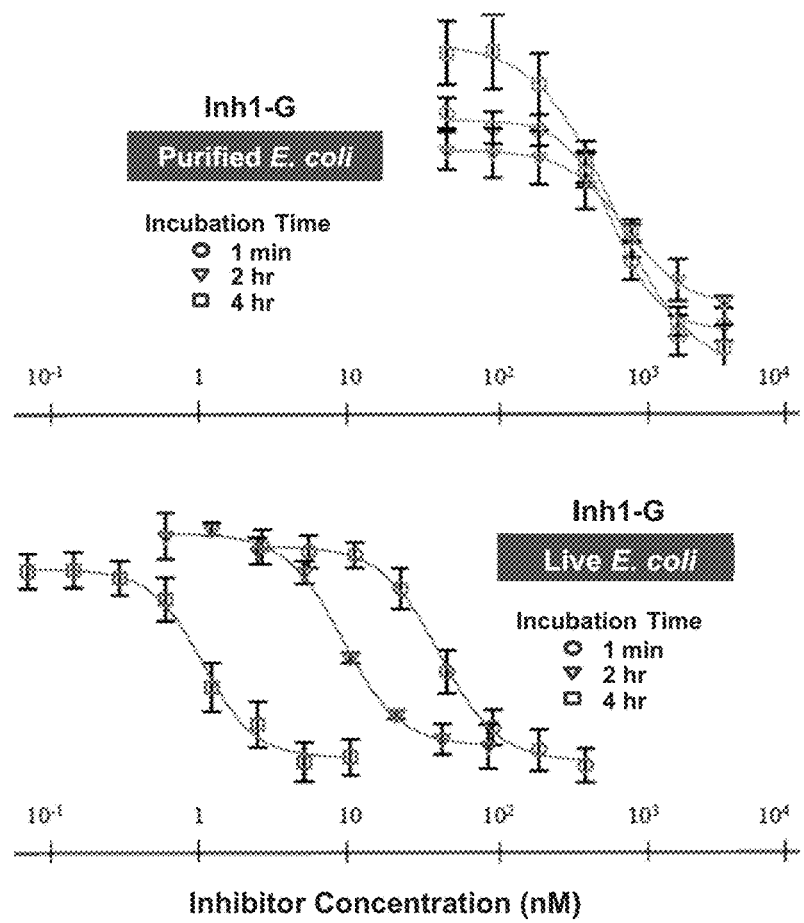

Figure 3: $IC_{50}$ potency curves of Inh1-G against purified E. coli GUS (top) and in live E. coli cells (bottom). Inh1-G was tested at nine concentrations over a >100-fold concentration range, and at three pre-incubation times (1 minute, 2 and 4 hours) with either purified enzyme or in live cells.

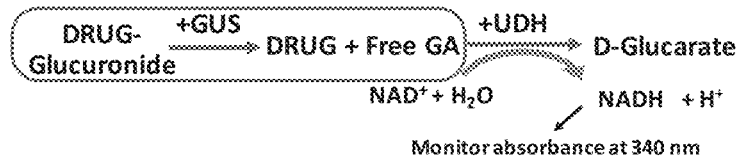

Figure 4: The GUS-UDH reaction for detection of free GA formed by the GUS-mediated catalysis of drug-glucuronides, using the UDH-mediated conversion of free GA to D-glucurate and the concomitant reduction of NAD+ to NADH, which can be monitored photometrically.

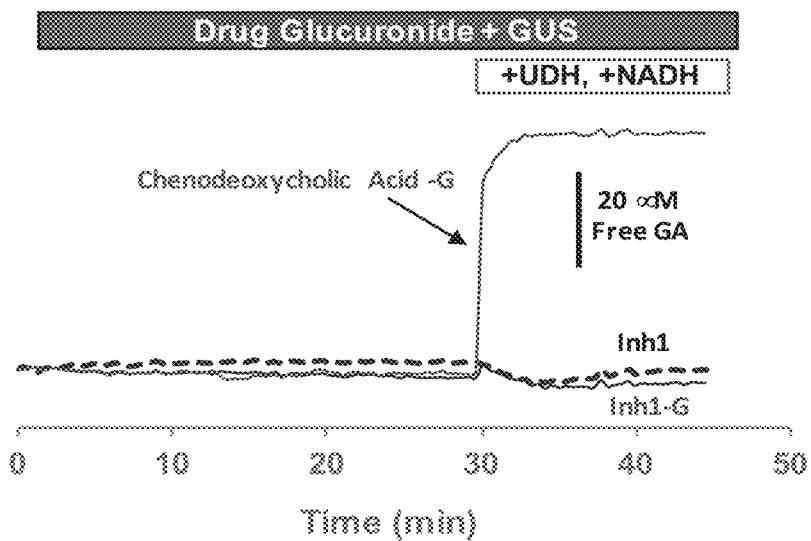

Figure 5: Inh1-G, Inh1 (negative control), and chenodeoxycholate-glucuronide (positive control) were incubated for ~30 minutes in *E. coli* GUS, followed by addition of NAD+ and UDH. NADH formation due to the production of free GA by the GUS reaction in the reaction wells were detected only for the positive control. No free GA was detected following incubation of Inh1-G with GUS.

COMPOUNDS, COMPOSITIONS, AND METHODS FOR SELECTIVELY INHIBITING β-GLUCURONIDASES AND ALLEVIATING SIDE EFFECTS ASSOCIATED WITH DRUG TREATMENT INDUCED DIARRHEA

CROSS-REFERENCE TO RELATED APPLICATIONS

This application is a 371 national phase of PCT/US2018/049891, filed Sep. 7, 2018, which claims the benefit of U.S. Provisional Application No. 62/555,847, filed Sep. 8, 2017, the entire contents of which are hereby incorporated herein by reference.

This invention was made with government support under grant number 1R43CA180270 awarded by the National Institute of Health, National Cancer Institute. The government has certain rights to the invention.

FIELD OF THE INVENTION

The present disclosure describes compounds and compositions that inhibit β-glucuronidase activity, and methods for attenuating the side effects of one or more drugs and improving the efficacy of drugs by administration of selective β-glucuronidase inhibitors.

BACKGROUND

Diarrhea is a common adverse effect associated with drug therapy. Hundreds of drugs have been implicated in causing diarrhea or gastrointestinal distress, including antibiotics, laxatives, magnesium-containing antacids, lactose- or sorbitol-containing products, nonsteroidal anti-inflammatory drugs, prostaglandins, colchicine, antineoplastic agents, antiarrhythmic drugs and cholinergic agents. The administration of all these drugs involves the delicate balance between efficacious therapy and patient discomfort and or severe gastrointestinal distress. Drug induced diarrhea can occur without warning and escalate within hours to become severe. Even mild-to-moderate grade diarrhea can be life-threatening when complicated by comorbid vomiting, dehydration, or neutropenia. In the early 2000's, chemotherapy regimens containing irinotecan (IRI) and 5-fluorouracil/leucovorin (5-FU/LV) revolutionized treatment for patients with advanced colorectal cancer, but their therapeutic benefit was compromised by diarrhea that occurred in up to 88% of patients. Clinical trials of IRI plus highdose 5-FU/LV reported early death rates of 2.2% to 4.8%, primarily due to gastrointestinal toxicity.

Drug induced diarrhea (DID) is a burden on multiple levels and can have psychosocial effects on sufferers, who may harbor feelings of embarrassment, isolation and distress. Patients avoid social contact and may not reach out to seek medical help until it escalates. Multiple studies suggest that DID is under-reported in clinical trials and in the real-world setting. In a recent survey of breast cancer patients, diarrhea was second only to nausea/vomiting as a feared toxicity of chemotherapy. When given the choice of certain death from stopping chemotherapy or chronic diarrhea from continuing chemotherapy, 42% surveyed chose death. For patients who cannot tolerate it, the oncologist's last, often used recourse is to reduce or stop chemotherapy before it kills the patient. Furthermore, DID can often become a dose-limiting side effect of the drug therapy that can impair treatment outcome.

One of the underlying mechanisms of DID is caused by enteric bacteria expressing the β-glucuronidase (bGUS) enzyme classified as a hydrolase. "Glucuronidation" is a common metabolic process involved in drug metabolism whereby glucuronide acts as a conjugation molecule and binds to a substrate via the catalysis of glucuronosyltransferase (UGT) enzymes. The human body uses glucuronidation to make a variety of substances more water-soluble, which allows easy elimination from the body through urine and/or feces. The β-glucuronidase enzyme is involved in the cleaving of glucuronide conjugates. However, drugs or their metabolites which are substrates for glucuronidases can have their respective properties altered by glucuronidase hydrolysis. For example, if the drug, agent compound or metabolite thereof has been metabolized to a glucuronide, the hydrolysis of the glucuronide can reactivate the drug, agent, compound or metabolite thereof. In many cases, this reactivation can cause adverse reactions, including but not limited to, gastrointestinal distress, leading to diarrhea.

For example, IRI (also called CPT-11) is an i.v.-infused pro-drug that is systemically metabolized by carboxylesterases into the active moiety SN-38, a potent topoisomerase-1 inhibitor. SN-38 is cytotoxic to rapidly dividing cancer cells, as well as enterocytes and neutrophils. It is metabolized by liver UGT enzymes into an inactive glucuronide metabolite SN-38G, which is then excreted along with bile secretions into the small intestine. As SN-38G is transported down the lower GI tract, enteric bacteria expressing the β-glucuronidase (bGUS) enzyme cleave SN-38G back into SN-38, which accumulates to toxic levels in the intestinal lumen. The local reactivation of SN-38 in the intestinal lumen by gut bacteria is considered to be the upstream triggering event that leads to delayed diarrhea.

While broad-spectrum antibiotics have been used to eliminate enteric bacteria from the gastrointestinal tract prior to chemotherapy treatment to reduce reactivation, this approach has several drawbacks. First, enteric bacteria (i.e., normal flora) play essential roles in carbohydrate metabolism, vitamin production and the processing of bile acids, sterols and xenobiotics. Thus, a partial or complete removal of enteric bacteria is not ideal for subjects already challenged by cancer and chemotherapy. Second, the elimination of the symbiotic enteric bacteria from even healthy subjects significantly increases risk of infection by pathogenic bacteria, including enterohemorrhagic *Escherichia coli* and *Clostridium difficile*. Third, bacterial antibiotic resistance is a human health crisis, and the unnecessary use of antibiotics is a significant contributor to this crisis.

Thus there remains a need to attenuate the side effects from drugs such as DID and also improve the efficacy drugs that cause DID through the administration of selective β-glucuronidase inhibitors.

SUMMARY

One embodiment of the present invention is a compound of formula (IA):

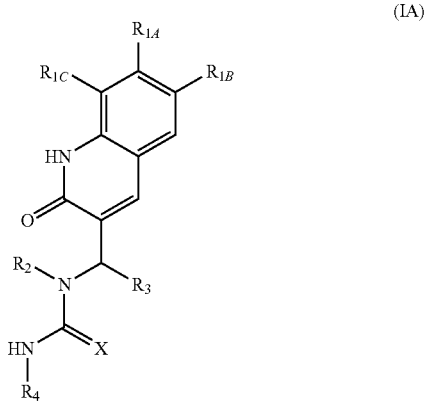

wherein
each of $R_{1A}$, $R_{1B}$, $R_{1C}$ independently is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of formula (IAG):

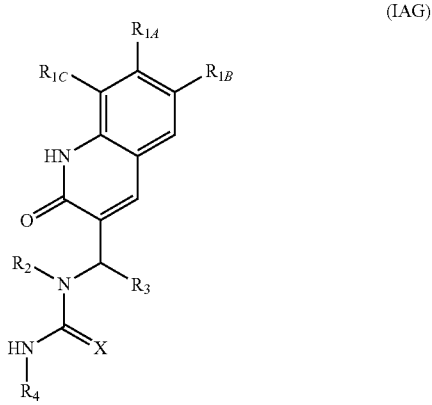

wherein
each of $R_{1A}$, $R_{1B}$, $R_{1C}$ independently is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, $C(O)R_d$, or

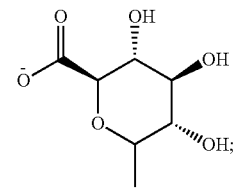

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One embodiment of the present invention is a compound of formula (IB):

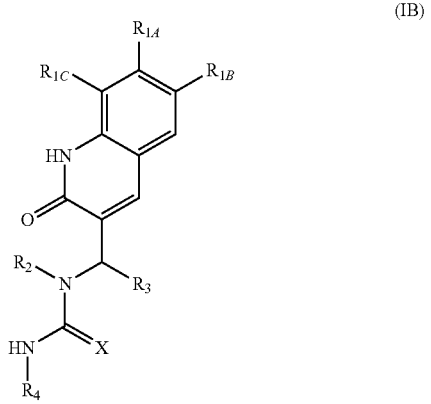

(IB)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_1$, $C_3$, $C_4$, $C_5$, or $C_6$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of formula (IBG):

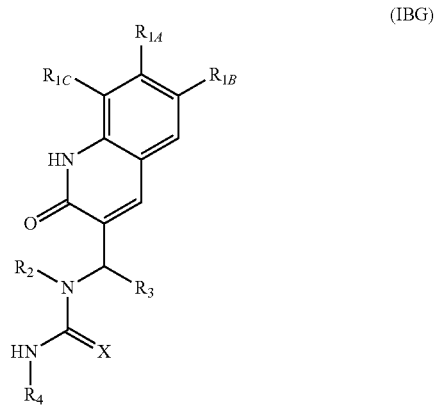

(IBG)

wherein
each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_1$, $C_3$, $C_4$, $C_5$ or $C_6$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, $C(O)R_d$, or

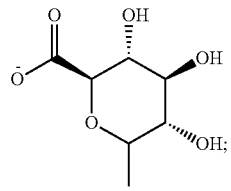

$R_c$ is aryl;
$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;
$R_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One embodiment of the present invention is a compound of formula (IC):

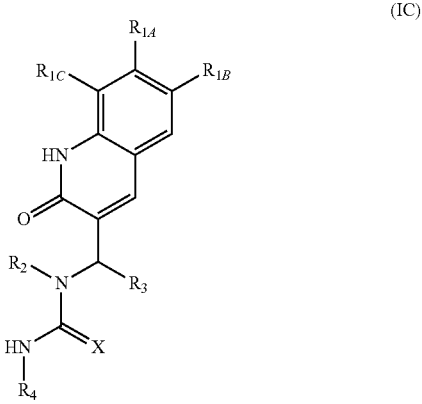

(IC)

wherein
each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;
$R_c$ is aryl;
$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted C$_{1-6}$ haloalkylthio, substituted or unsubstituted C$_{1-6}$ alkylamino, substituted or unsubstituted C$_{2-6}$ alkenyl, substituted or unsubstituted C$_{2-6}$ haloalkenyl, substituted or unsubstituted C$_{2-6}$ alkynyl, substituted or unsubstituted C$_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

R$_4$ is selected from the group consisting of unsubstituted phenyl, or a substituted or unsubstituted 3- to 10-membered ring, having one or more heteroatoms selected from N, O, or S, and optionally having one or more degrees of unsaturation;

or a glucuronide thereof or a pharmaceutically acceptable salt thereof.

One embodiment of the present invention is a compound of formula (ICG):

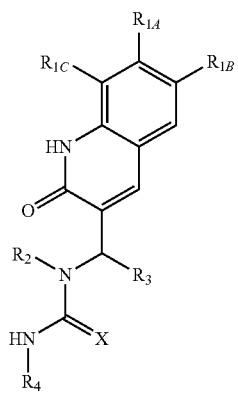

(ICG)

wherein each of R$_{1A}$, R$_{1B}$, R$_{1C}$ independently is hydrogen, substituted or unsubstituted C$_{1-6}$ alkyl, substituted or unsubstituted C$_{1-6}$ haloalkyl, substituted or unsubstituted C$_{1-6}$ alkoxy, substituted or unsubstituted C$_{1-6}$ alkylthio, substituted or unsubstituted C$_{1-6}$ haloalkoxy, substituted or unsubstituted C$_{1-6}$ haloalkylthio, substituted or unsubstituted C$_{1-6}$ alkylamino, substituted or unsubstituted C$_{1-6}$ alkylaminoalkyl, substituted or unsubstituted C$_{2-6}$ alkenyl, substituted or unsubstituted C$_{2-6}$ haloalkenyl, substituted or unsubstituted C$_{2-6}$ alkynyl, substituted or unsubstituted C$_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

R$_2$ is (L$_1$)$_n$R$_a$, wherein L$_1$ is a C$_{1-6}$ alkylene chain, n is 0 or 1, and R$_a$ is OR$_b$, C$_{1-6}$ alkylamino, or a substituted or unsubstituted 3- to 10-membered ring, optionally having one or more heteroatoms selected from N, O, or S, and optionally having one or more degrees of unsaturation;

R$_b$ is hydrogen, C(O)NHR$_c$, C(O)R$_d$, or

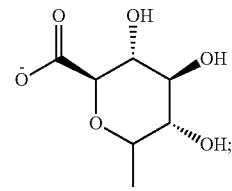

R$_c$ is aryl;

R$_d$ is substituted or unsubstituted C$_{1-6}$ alkyl, substituted or unsubstituted C$_{1-6}$ haloalkyl, substituted or unsubstituted C$_{1-6}$ alkoxy, substituted or unsubstituted C$_{1-6}$ alkylthio, substituted or unsubstituted C$_{1-6}$ haloalkoxy, substituted or unsubstituted C$_{1-6}$ haloalkylthio, substituted or unsubstituted C$_{1-6}$ alkylamino, substituted or unsubstituted C$_{1-6}$ alkylaminoalkyl, substituted or unsubstituted C$_{2-6}$ alkenyl, substituted or unsubstituted C$_{2-6}$ haloalkenyl, substituted or unsubstituted C$_{2-6}$ alkynyl, substituted or unsubstituted C$_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

R$_3$ is hydrogen, substituted or unsubstituted C$_{1-6}$ alkyl, substituted or unsubstituted C$_{1-6}$ haloalkyl, substituted or unsubstituted C$_{1-6}$ alkoxy, substituted or unsubstituted C$_{1-6}$ alkylthio, substituted or unsubstituted C$_{1-6}$ haloalkoxy, substituted or unsubstituted C$_{1-6}$ haloalkylthio, substituted or unsubstituted C$_{1-6}$ alkylamino, substituted or unsubstituted C$_{2-6}$ alkenyl, substituted or unsubstituted C$_{2-6}$ haloalkenyl, substituted or unsubstituted C$_{2-6}$ alkynyl, substituted or unsubstituted C$_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

R$_4$ is selected from the group consisting of unsubstituted phenyl, or a substituted or unsubstituted 3- to 10-membered ring, having one or more heteroatoms selected from N, O, or S, and optionally having one or more degrees of unsaturation;

or a pharmaceutically acceptable salt thereof.

One embodiment of the present invention is a compound of formula (ID):

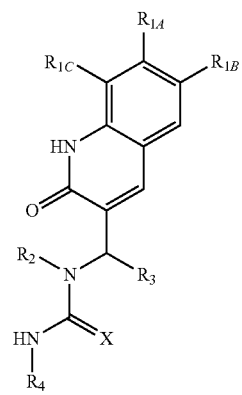

(ID)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O;

$R_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of formula (IDG):

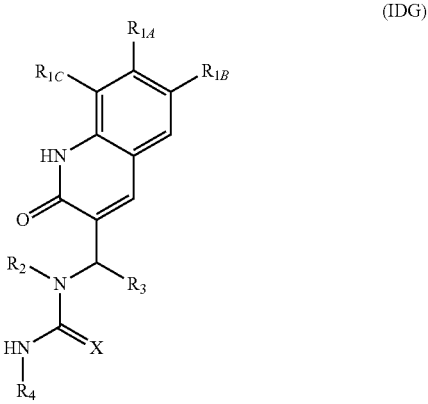

(IDG)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, $C(O)R_d$, or

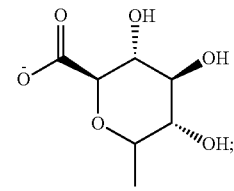

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

R$_3$ is hydrogen, substituted or unsubstituted C$_{1-6}$ alkyl, substituted or unsubstituted C$_{1-6}$ haloalkyl, substituted or unsubstituted C$_{1-6}$ alkoxy, substituted or unsubstituted C$_{1-6}$ alkylthio, substituted or unsubstituted C$_{1-6}$ haloalkoxy, substituted or unsubstituted C$_{1-6}$ haloalkylthio, substituted or unsubstituted C$_{1-6}$ alkylamino, substituted or unsubstituted C$_{2-6}$ alkenyl, substituted or unsubstituted C$_{2-6}$ haloalkenyl, substituted or unsubstituted C$_{2-6}$ alkynyl, substituted or unsubstituted C$_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O;

R$_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One embodiment of the present invention is a compound of formula (IE):

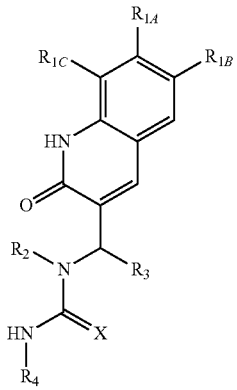

(IE)

wherein each of R$_{1A}$, R$_{1B}$, R$_{1C}$ independently is substituted or unsubstituted C$_{1-6}$ alkyl, substituted or unsubstituted C$_{1-6}$ haloalkyl, substituted or unsubstituted C$_{1-6}$ alkoxy, substituted or unsubstituted C$_{1-6}$ alkylthio, substituted or unsubstituted C$_{1-6}$ haloalkoxy, substituted or unsubstituted C$_{1-6}$ haloalkylthio, substituted or unsubstituted C$_{1-6}$ alkylamino, substituted or unsubstituted C$_{1-6}$ alkylaminoalkyl, substituted or unsubstituted C$_{2-6}$ alkenyl, substituted or unsubstituted C$_{2-6}$ haloalkenyl, substituted or unsubstituted C$_{2-6}$ alkynyl, substituted or unsubstituted C$_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

R$_2$ is (L$_1$)$_n$R$_a$, wherein L$_1$ is a C$_{1-6}$ alkylene chain, n is 0 or 1, and R$_a$ is OR$_b$, C$_{1-6}$ alkylamino, or a substituted or unsubstituted 3- to 10-membered ring, optionally having one or more heteroatoms selected from N, O, or S, and optionally having one or more degrees of unsaturation;

R$_b$ is hydrogen, C(O)NHR$_c$, or C(O)R$_d$;

R$_c$ is aryl;

R$_d$ is substituted or unsubstituted C$_{1-6}$ alkyl, substituted or unsubstituted C$_{1-6}$ haloalkyl, substituted or unsubstituted C$_{1-6}$ alkoxy, substituted or unsubstituted C$_{1-6}$ alkylthio, substituted or unsubstituted C$_{1-6}$ haloalkoxy, substituted or unsubstituted C$_{1-6}$ haloalkylthio, substituted or unsubstituted C$_{1-6}$ alkylamino, substituted or unsubstituted C$_{1-6}$ alkylaminoalkyl, substituted or unsubstituted C$_{2-6}$ alkenyl, substituted or unsubstituted C$_{2-6}$ haloalkenyl, substituted or unsubstituted C$_{2-6}$ alkynyl, substituted or unsubstituted C$_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

R$_3$ is substituted or unsubstituted C$_{1-6}$ alkyl, substituted or unsubstituted C$_{1-6}$ haloalkyl, substituted or unsubstituted C$_{1-6}$ alkoxy, substituted or unsubstituted C$_{1-6}$ alkylthio, substituted or unsubstituted C$_{1-6}$ haloalkoxy, substituted or unsubstituted C$_{1-6}$ haloalkylthio, substituted or unsubstituted C$_{1-6}$ alkylamino, substituted or unsubstituted C$_{2-6}$ alkenyl, substituted or unsubstituted C$_{2-6}$ haloalkenyl, substituted or unsubstituted C$_{2-6}$ alkynyl, substituted or unsubstituted C$_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

R$_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of formula (IEG):

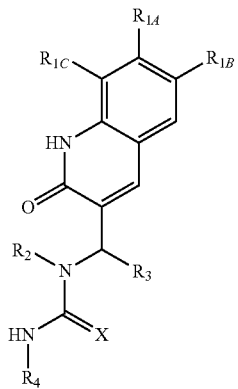

(IEG)

wherein each of R$_{1A}$, R$_{1B}$, R$_{1C}$ independently is substituted or unsubstituted C$_{1-6}$ alkyl, substituted or unsubstituted C$_{1-6}$ haloalkyl, substituted or unsubstituted C$_{1-6}$ alkoxy, substituted or unsubstituted C$_{1-6}$ alkylthio, substituted or unsubstituted C$_{1-6}$ haloalkoxy, substituted or unsubstituted C$_{1-6}$ haloalkylthio, substituted or unsubstituted C$_{1-6}$ alkylamino, substituted or unsubstituted C$_{1-6}$ alkylaminoalkyl, substituted or unsubstituted C$_{2-6}$ alkenyl, substituted or unsubstituted C$_{2-6}$ haloalkenyl, substituted or unsubstituted C$_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_nR_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, $C(O)R_d$, or

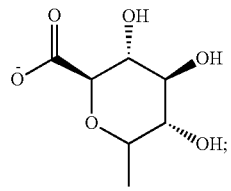

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One embodiment of the present invention is a compound of the formula (II):

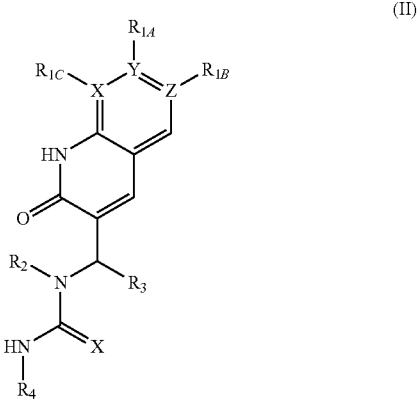

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

each of X, Y or Z individually is C or N;

$R_2$ is $(L_1)_nR_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of the formula (IIG):

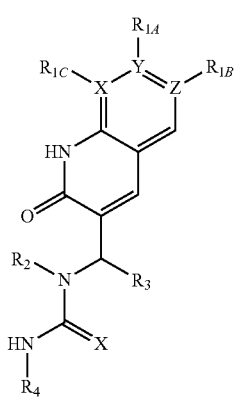

(IIG)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

each of X, Y or Z individually is C or N;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, $C(O)R_d$ or

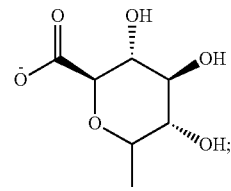

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One aspect of one or more embodiments of the present invention includes wherein $R_{1A}$ is selected from substituted $C_{1-6}$ alkyl or $C_{1-6}$ alkylaminoalkyl. One aspect of one or more embodiments of the present invention includes wherein the $C_{1-6}$ alkyl is substituted with a. a substituted or unsubstituted 3- to 10-membered ring, optionally having one or more heteroatoms selected from N, O, or S, and optionally having one or more degrees of unsaturation, or b. $OC(O)R_x$, wherein $R_x$ is $C_{1-6}$ alkyl.

One aspect of one or more embodiments of the present invention includes wherein $R_2$ is $(L_1)_n R_a$, wherein $L_1$ is a $C_2$ alkylene, n is 1, and $R_a$ is $OR_b$, wherein $R_b$ is hydrogen.

One aspect of one or more embodiments of the present invention includes wherein $R_2$ is $(L_1)_n R_a$, n is 0, and $R_a$ is a substituted or unsubstituted 3- to 10-membered ring, optionally having one or more heteroatoms selected from N, O, or S, and optionally having one or more degrees of unsaturation.

One aspect of one or more embodiments of the present invention includes wherein $R_{1A}$ is substituted $C_{1-6}$ alkyl; $R_2$ is $(L_1)_nR_a$, wherein $L_1$ is a $C_2$ alkylene, n is 1, and $R_a$ is $OR_b$, wherein $R_b$ is hydrogen; and X is S. One aspect of one or more embodiments of the present invention includes wherein the $C_{1-6}$ alkyl is substituted with a. a substituted or unsubstituted 3- to 10-membered ring, optionally having one or more heteroatoms selected from N, O, or S, and optionally having one or more degrees of unsaturation, or b. $OC(O)R_x$, wherein $R_x$ is $C_{1-6}$ alkyl.

One aspect of one or more embodiments of the present invention includes wherein $R_{1A}$ is $C_{1-6}$ alkylaminoalkyl; and $R_2$ is $(L_1)_nR_a$, wherein $L_1$ is a $C_2$ alkylene, n is 1, and $R_a$ is $OR_b$, wherein $R_b$ is hydrogen.

One aspect of one or more embodiments of the present invention includes wherein $R_{1A}$ is $C_{1-6}$ alkylaminoalkyl; and $R_2$ is $(L_1)_nR_a$, wherein n is 0, and $R_a$ is a substituted or unsubstituted 3- to 10-membered ring, optionally having one or more heteroatoms selected from N, O, or S, and optionally having one or more degrees of unsaturation.

One aspect of one or more embodiments of the present invention includes wherein $R_1$ is $C_{1-6}$ alkylaminoalkyl, and $R_2$ is $(L_1)_nR_a$, wherein n is 0, and $R_a$ is a substituted or unsubstituted 3- to 10-membered ring, optionally having one or more heteroatoms selected from N, O, or S, and optionally having one or more degrees of unsaturation; and X is O.

One aspect of one or more embodiments of the present invention includes wherein $R_2$ is $C(O)R_d$, and wherein $R_d$ is $C_{1-6}$ alkyl or a substituted or unsubstituted 3- to 10-membered ring, optionally having one or more heteroatoms selected from N, O, or S, and optionally having one or more degrees of unsaturation.

One aspect of one or more embodiments of the present invention includes wherein: each of $R_{1A}$, $R_{1B}$, and $R_{1C}$ independently is hydrogen or $C_{1-6}$ alkyl; $R_2$ is $(L_1)_nR_a$, wherein $L_1$ is a $C_2$ alkylene, n is 1, and $R_a$ is $OR_b$, wherein $R_b$ is hydrogen; $R_3$ is hydrogen, a substituted or unsubstituted $C_{1-6}$ alkyl, or a substituted or unsubstituted 3- to 10-membered ring, optionally having one or more heteroatoms selected from N, O, or S, and optionally having one or more degrees of unsaturation; $R_4$ is a substituted or unsubstituted 6-membered ring, optionally having one or more heteroatoms selected from N, O, or S, and optionally having one or more degrees of unsaturation. One aspect of one or more embodiments of the present invention includes wherein: $R_{1A}$ is hydrogen; each of $R_{1B}$ and $R_{1C}$ is methyl; $R_3$ is hydrogen, $C_{1-6}$ alkyl, or $C_{3-10}$ cycloalkyl; and $R_4$ is a substituted or unsubstituted phenyl or pyridyl.

One aspect of one or more embodiments of the present invention includes wherein $R_3$ is $C_{1-6}$ alkyl or a substituted or unsubstituted 3- to 10-membered ring, optionally having one or more heteroatoms selected from N, O, or S, and optionally having one or more degrees of unsaturation.

One aspect of one or more embodiments of the present invention includes wherein $R_3$ is $C_{1-6}$ alkyl or $C_{3-10}$ cycloalkyl.

One embodiment of the present invention includes a compound selected from the group consisting of:
[3[[(4-ethoxyphenyl)carbamothioyl-(2-hydroxyethyl) amino]methyl]-6,8-dimethyl-2-oxo-1H-quinolin-7-yl] methyl acetate;
1-[[6,8-dimethyl-7-[(4-methylpiperazin-1-yl)methyl]-2-oxo-1H-quinolin-3-yl]methyl]-3-(4-ethoxyphenyl)-1-(2-hydroxyethyl)thiourea;
1-[[6,8-dimethyl-7-[(4-methylpiperazin-1-yl)methyl]-2-oxo-1H-quinolin-3-yl]methyl]-3-(4-ethoxy phenyl)-1-(2-hydroxyethyl)urea;

1-[[7-(diethylaminomethyl)-6,8-dimethyl-2-oxo-1H-quinolin-3-yl]methyl]-3-(4-ethoxyphenyl)-1-(2-hydroxyethyl) thiourea;
1-[[7-(diethylaminomethyl)-6,8-dimethyl-2-oxo-1H-quinolin-3-yl]methyl]-3-(4-ethoxy phenyl)-1-(2-hydroxyethyl) urea;
tert-butyl-3-[[7-(diethylaminomethyl)-6,8-dimethyl-2-oxo-1H-quinolin-3-yl]methyl-[(4-ethoxyphenyl)carbamoyl] amino]pyrrolidine-1-carboxylate;
1-[[7-(diethylaminomethyl)-6,8-dimethyl-2-oxo-1H-quinolin-3-yl]methyl]-3-(4-ethoxyphenyl)-1-pyrrolidin-3-yl-thiourea;
1-[[7-(diethylaminomethyl)-6,8-dimethyl-2-oxo-1H-quinolin-3-yl]methyl]-3-(4-ethoxyphenyl)-1-pyrrolidin-3-yl-urea;
tert-butyl 3-[[7-(diethylaminomethyl)-6,8-dimethyl-2-oxo-1H-quinolin-3-yl]methyl-[((4-ethoxyphenyl)carbamothioyl]amino]azetidine-1-carboxylate;
tert-butyl 3-[[7-(diethylaminomethyl)-6,8-dimethyl-2-oxo-1H-quinolin-3-yl]methyl-[(4-ethoxyphenyl)carbamoyl] amino]azetidine-1-carboxylate;
1-(azetidin-3-yl)-1-[[7-(diethylaminomethyl)-6,8-dimethyl-2-oxo-1H-quinolin-3-yl]methyl]-3-(4-ethoxyphenyl)thiourea;
1-(azetidin-3-yl)-1-[[7-(diethylaminomethyl)-6,8-dimethyl-2-oxo-1H-quinolin-3-yl]methyl]-3-(4-ethoxyphenyl) urea;
1-[[7-(diethylaminomethyl)-6,8-dimethyl-2-oxo-1H-quinolin-3-yl]methyl]-3-(4-ethoxyphenyl)-1-(3-hydroxycyclobutyl)thiourea;
1-[[7-(diethylaminomethyl)-6,8-dimethyl-2-oxo-1H-quinolin-3-yl]methyl]-3-(4-ethoxyphenyl)-1-(3-hydroxycyclobutyl)urea;
1-[[6,8-dimethyl-7-(morpholinomethyl)-2-oxo-1H-quinolin-3-yl]methyl]-3-(4-ethoxyphenyl)-1-(2-hydroxyethyl) urea; and
1-[[6,8-dimethyl-7-(morpholinomethyl)-2-oxo-1H-quinolin-3-yl]methyl]-3-(4-ethoxyphenyl)-1-(2-hydroxyethyl) thiourea;

or a pharmaceutically acceptable salt thereof.

One embodiment of the present invention includes a compound selected from the group consisting of:

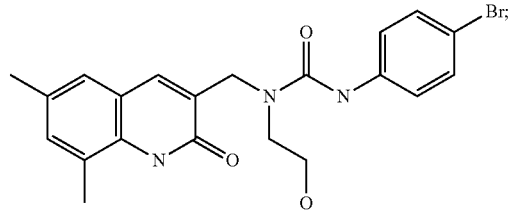

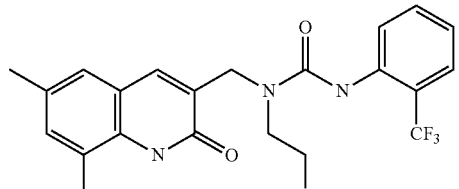

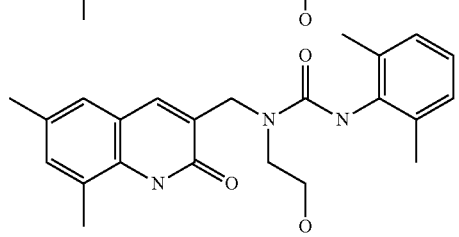

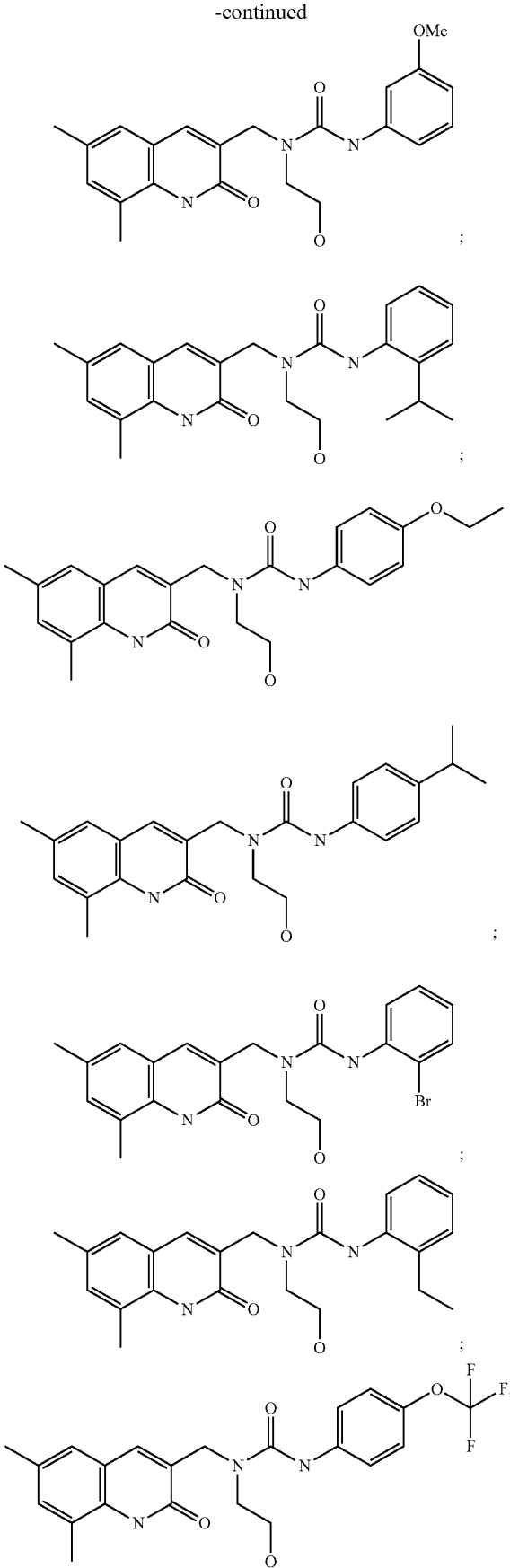
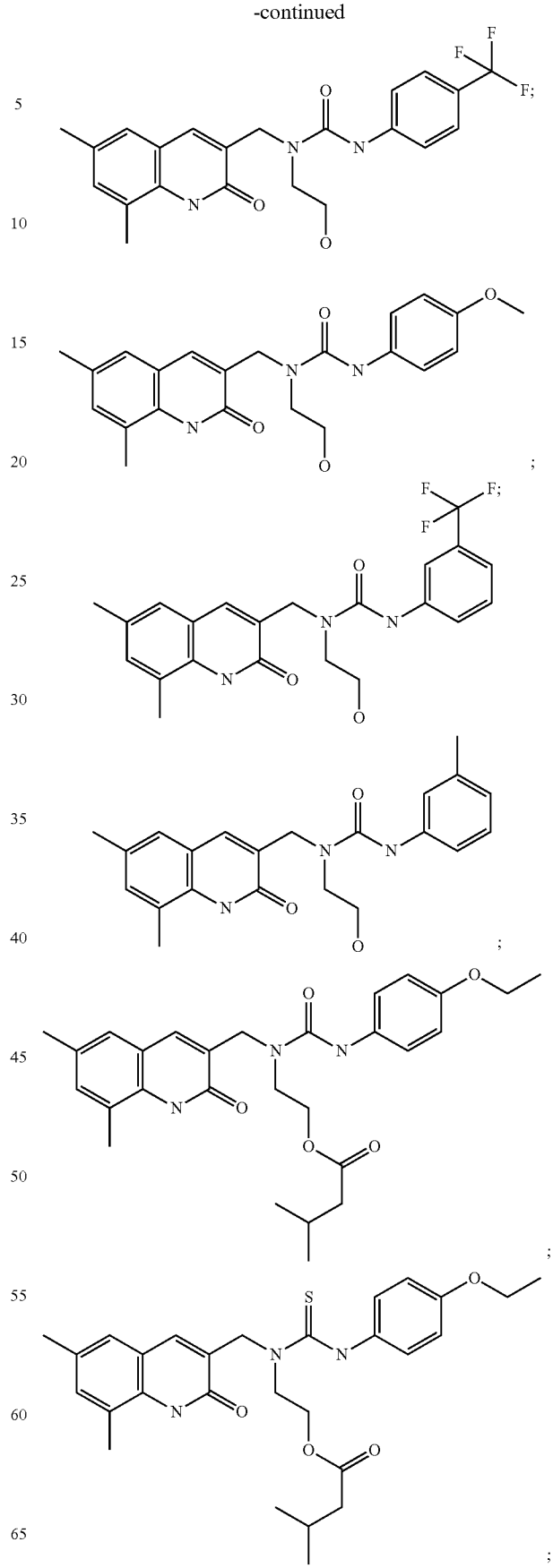

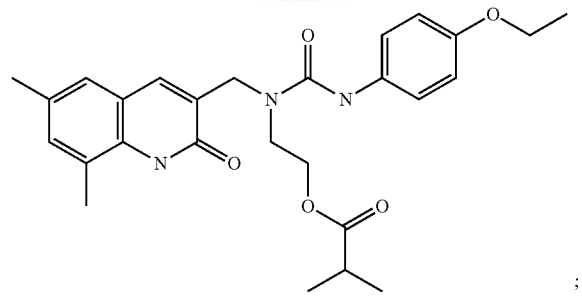
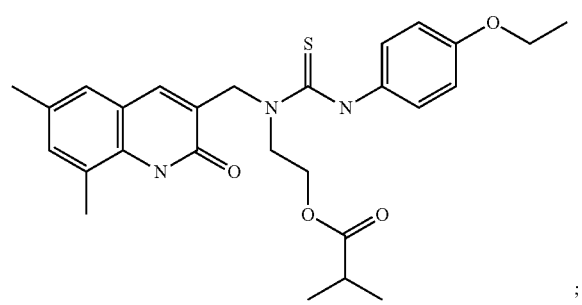
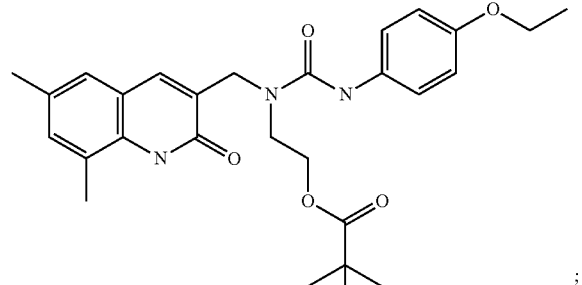
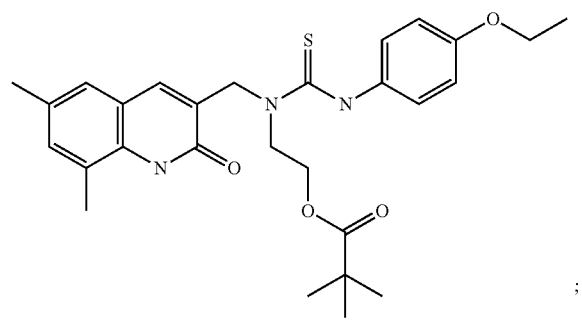
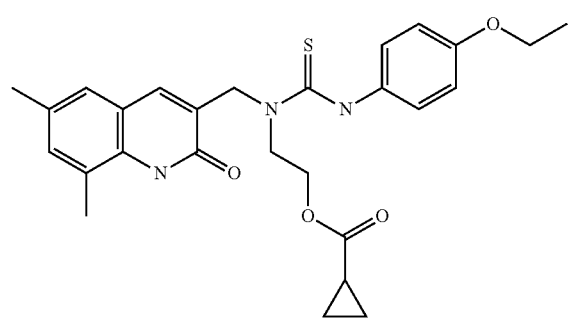

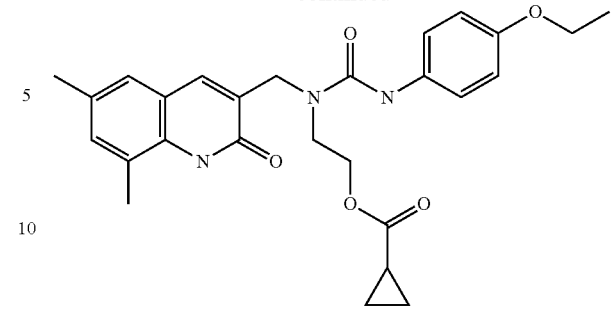

or a pharmaceutically acceptable salt thereof.

One embodiment of the present invention includes a compound selected from the group consisting of:
3-(2-Bromophenyl)-1-[(6,8-dimethyl-2-oxo-1H-quinolin-3-yl)methyl]-1-(2-hydroxyethyl)urea;
1-[(6,8-dimethyl-2-oxo-1H-quinolin-3-yl)methyl]-1-(2-hydroxyethyl)-3-(2-isopropylphenyl)urea;
1-[(6,8-dimethyl-2-oxo-1H-quinolin-3-yl)methyl]-1-(2-hydroxyethyl)-3-(2-phenylphenyl)urea;
1-[(6,8-dimethyl-2-oxo-1H-quinolin-3-yl)methyl]-1-(2-hydroxyethyl)-3-(3-pyridyl)urea;
1-[(6,8-dimethyl-2-oxo-1H-quinolin-3-yl)methyl]-1-(2-hydroxyethyl)-3-(2-iodophenyl)urea;
1-[(6,8-dimethyl-2-oxo-1H-quinolin-3-yl)methyl]-3-(4-fluoro-2-iodo-phenyl)-1-(2-hydroxyethyl)urea;
1-[1-(6,8-dimethyl-2-oxo-1H-quinolin-3-yl)ethyl]-1-(2-hydroxyethyl)-3-(3-methoxyphenyl)urea;
1-[(6,8-dimethyl-2-oxo-1H-quinolin-3-yl)methyl]-1-(2-hydroxyethyl)-3-(m-tolyl)urea;
1-[(6,8-dimethyl-2-oxo-1H-quinolin-3-yl)methyl]-1-(2-hydroxyethyl)-3-(3-isopropylphenyl)urea;
1-[(6,8-dimethyl-2-oxo-1H-quinolin-3-yl)methyl]-1-(2-hydroxyethyl)-3-[4-methyl-2-(2-trimethylsilylethynyl)phenyl]urea;
1-[(6,8-dimethyl-2-oxo-1H-quinolin-3-yl)methyl]-3-(2-ethynyl-4-fluoro-phenyl)-1-(2-hydroxyethyl)urea;
1-[1-(6,8-dimethyl-2-oxo-1H-quinolin-3-yl)ethyl]-1-(2-hydroxyethyl)-3-(2-isopropylphenyl)urea;
1-[1-(6,8-dimethyl-2-oxo-1H-quinolin-3-yl)ethyl]-3-(4-fluoro-2-iodo-phenyl)-1-(2-hydroxyethyl)urea;
1-[1-(6,8-dimethyl-2-oxo-1H-quinolin-3-yl)ethyl]-1-(2-hydroxyethyl)-3-(o-tolyl)urea; and 1-[1-(6,8-dimethyl-2-oxo-1H-quinolin-3-yl)ethyl]-1-(2-hydroxyethyl)-3-(4-methoxyphenyl)urea;
or a pharmaceutically acceptable salt thereof.

One embodiment of the present invention includes a compound or compounds of the present invention and one or more pharmaceutically acceptable carriers.

One embodiment of the present invention includes a method for attenuating the side effects of one or more drug, by administering to a subject in need thereof an effective amount of one or more compounds of the present invention. In one aspect of an embodiment, the one or more compounds selectively inhibit β-glucuronidase. In one aspect of an embodiment, the one or more compounds can be co-administered with the one or more therapeutic compound or product.

One embodiment of the present invention includes a compound of the present invention for use in medicine. In one aspect of an embodiment, the one or more compounds selectively inhibit β-glucuronidase. In one aspect of an embodiment, the one or more compounds can be co-administered with the one or more therapeutic compound or product.

One embodiment of the present invention includes a compound of the present invention for the manufacture of a medicament for attenuating side effects of one or more drug. In one aspect of an embodiment the one or more compounds selectively inhibit β-glucuronidase. In one aspect of an embodiment, the one or more compounds can be co-administered with the one or more therapeutic compound or product.

One embodiment of the present invention includes use of a compound of the present invention for attenuating the side effects of one or more drug. In one aspect of an embodiment, the one or more compounds selectively inhibit β-glucuronidase. In one aspect of an embodiment, the one or more compounds can be co-administered with the one or more therapeutic compound or product.

One or more aspects and embodiments may be incorporated in a different embodiment although not specifically described. That is, all aspects and embodiments can be combined in any way or combination.

BRIEF DESCRIPTION OF THE FIGURES

FIG. 1 depicts the structure of Inh1 and Inh1 glucuronide (Inh1-G).

FIG. 2 depicts bar graphs summarizing the $IC_{50}$'s of Inh1 and Inh1-G.

FIG. 3 depicts $IC_{50}$ potency curves of Inh1-G against purified E. coli GUS (top) and in live E. coli cells (bottom). Inh1-G was tested at nine concentrations over a >100-fold concentration range, and at three pre-incubation times (1 minute, 2 and 4 hours) with either purified enzyme or in live cells.

FIG. 4 depicts the GUS-UDH reaction for detection of free GA formed by the GUS-mediated catalysis of drug-glucuronides, using the UDH-mediated conversion of free GA to D-glucarate and the concomitant reduction of NAD+ to NADH, which can be monitored photometrically.

FIG. 5 depicts Inh1-G, Inh1 (negative control), and chenodeoxycholate-glucuronide (positive control) were incubated for 30 minutes in E. coli GUS, followed by addition of NAD+ and UDH. NADH formation due to the production of free GA by the GUS reaction in the reaction wells were detected only for the positive control. No free GA was detected following incubation of Inh1-G with GUS.

DETAILED DESCRIPTION

Definitions

When referring to the compounds disclosed herein, the following terms have the following meanings unless indicated otherwise. The following definitions are meant to clarify, but not limit the terms defined. If a particular term used herein is not specifically defined, such term should not be considered indefinite. Rather, terms are used within their accepted meanings.

As used herein, the term "alkoxy" refers to the group —OR where R is alkyl. Illustrative alkoxy groups include methoxy, ethoxy, n-propoxy, isopropoxy, n-butoxy, tert-butoxy, sec-butoxy, n-pentoxy, n-hexoxy, and 1,2-dimethylbutoxy.

As used herein, "alkyl" refers to monovalent saturated aliphatic hydrocarbyl groups having from 1 to 20 carbon atoms, preferably 1-8 carbon atoms, preferably 1-6 carbon atoms. The hydrocarbon chain can be either straight-chained or branched. Illustrative alkyl groups include methyl, ethyl, n-propyl, isopropyl, n-butyl, iso-butyl, and tert-butyl. Similarly, an "alkenyl" group refers to an alkyl group having one or more double bonds present in the chain. An "alkynyl" group refers to an alkyl group having one or more triple bonds present in the chain.

As used herein, "alkylamino" refers to monovalent saturated aliphatic hydrocarbyl groups having from 1 to 20 carbon atoms, preferably 1-8 carbon atoms, preferably 1-6 carbon atoms, wherein at least one hydrogen atom is substituted by an amine. Similarly, "alkylaminoalkyl" refers to dialkyl "alkylamino", or alkylamino groups with more than one alkyl chain.

As used herein "aryl" refers to an aromatic ring system containing from 5 to 10 ring atoms. Illustrative aryl groups include phenyl and naphthyl.

As used herein "β-glucuronidase" refers to the bacterial or mammalian enzyme capable of hydrolyzing β-glucuronides. As used herein, "glucuronide" refers to a substance produced by linking glucuronic add to another substance. An illustrative example of glucuronides are those derived from neoplastic agents such as 7-ethyl-10-hydroxycamptothecin glucouronide derived from camptothecin antineoplastic agents.

As used herein "co-administration" refers to prior to, the same time as, or following administration of a glucuronidase-substrate agent(s)" or compounds, as defined below.

As used herein, "cycloalkyl" refers to an unsaturated or partially saturated hydrocarbon ring, containing from 3 to 6 ring atoms. Illustrative cycloalkyl groups include cyclopropyl, cyclobutyl, cyclopentyl, cyclohexyl, as well as partially saturated versions thereof, such as cyclohexenyl, and cyclohexadienyl.

As used herein, "dose-limiting" refers to a side effect from administration of a drug or glucuronidase-substrate agent or compound that prevents a subject in need thereof from receiving a therapeutically effective amount.

As used herein, "effective amount" refers to the amount sufficient to achieve a therapeutic effect when administered to a patient in need of treatment.

As used herein "halogen" or "halo" refers to a halogen. In some embodiments, the halogen is preferably Br, Cl, or F.

As used herein, "haloalkyl" refers to monovalent saturated aliphatic hydrocarbyl groups having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms. The haloalkyl chain can be either straight-chained or branched. Illustrative alkyl groups include trifluoromethyl, trifluoroethyl, trifluoropropyl, trifluorobutyl, and pentafluoroethyl. Similarly, a "haloalkenyl" group refers to a haloalkyl group having one or more double bonds present in the chain. A "haloalkynyl" group refers to a haloalkyl group having one or more triple bonds present in the chain.

As used herein, "haloalkylthio" refers to monovalent saturated aliphatic hydrocarbyl groups having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms, and a second hydrogen atom is substituted by sulfur. The haloalkylthio chain can be either straight-chained or branched.

As used herein "glucuronidase-substrate agent(s)" or compounds" refers to any drug, agent, compound, or metabolite thereof that can be a substrate for glucuronidase. In some instances, a drug, compound or agent that is not itself a substrate, but is metabolized to a substrate is encompassed by the term above as used herein. Any drug, compound, agent or metabolite thereof that is glucuronidated, also referred to as glucuuronides, can be a substrate for glucuronidase and is also described herein as glucuronidase-substrate agent(s) or compound(s). Many drugs, agents or compounds undergo glucuronidation at some point in their metabolism. Alternatively, the drug, agent, or compound may be a glucuronide pro-drug. These glucuronides may have different properties than the parent drug, agent or compound.

As used herein "optionally having one or more heteroatoms" refers to the substitution of a ring carbon atom with a nitrogen, oxygen, or sulfur atom. Similarly, "optionally having one or more degrees of unsaturation" refers to varying the number of bonds between atoms of a ring due any substitutions in the ring atoms that results in changes the number of valence electrons available for bonding.

As used herein "pharmaceutically acceptable salt" refers to any salt of a compound disclosed herein which retains its biological properties and which is not toxic or otherwise undesirable for pesticidal, veterinary, or pharmaceutical use. Such salts may be derived from a variety of organic and inorganic counter-ions known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfemic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzene sulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

As used herein, the term "selectively inhibits" and the like means that the β-glucuronidase inhibitor reduces either bacterial or mammalian β-glucuronidase activity.

As used herein, the terms "subject" and "patient" are used interchangeably herein. The terms "subject" and "subjects" refer to a primate such as a monkey such as a cynomolgous monkey, a chimpanzee, and a human or non-primate animal. In one embodiment the subject is a human. In another embodiment, the subject is a companion animal such as a dog or cat. In a further embodiment the subject is an animal of agricultural importance such as a sheep, cow, horse, goat fish, pig, or domestic fowl (such as a chicken, turkey, duck, or goose).

As used herein "substituted" refers to a substitution of a hydrogen atom, which would otherwise be present on the substituent. Wien discussing ring systems, the optional substitution is typically with 1, 2, or 3 substituents replacing the normally-present hydrogen. Wien referencing straight and branched moieties, however, the number of substitutions can be more, occurring wherever hydrogen is usually present. The substitutions can be the same or different. Illustrative substitutions include nitro, —NR'R", cyano, —NR'COR'", alkyl, alkenyl, alkynyl, alkylsilylalkynyl (namely, —C≡C—Si-alkyl), C(O), SO$_2$R'", NR'SO$_2$R'", SO$_2$NR'R", CONR'R", CONHC$_6$H$_5$, hydroxy, alkoxy, alkylsulfonyl, haloalkyl, haloalkenyl, haloalkoxy, mercapto (namely, —SH), thioalkyl, halogen, cycloalkyl, heterocyclyl, aryl, or heteroaryl, where R' and R" are the same or different and each represents hydrogen or alkyl; or when R' and R" are each attached to a nitrogen atom, they may form a saturated or unsaturated heterocyclic ring containing from 4 to 6 ring atoms, and wherein R'" is alkyl or haloalkyl.

In certain cases, the depicted substituents can contribute to optical and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposabie mirror images of each other are termed "enantiomers". When a compound has an asymmetric center, for example when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78: 413-447, *Angew. Chem., Int. Ed. Engl.* 5: 385-414 (errata: *Angew. Chem., Int. Ed. Engl.* 5:511); Prelog and Helmchen, 1982, *Angew. Chem.* 94: 614-631, *Angew. Chem. Internal. Ed. Eng.* 21: 567-583; Mata and Lobo, 1993, *Tetrahedron: Asymmetry* 4:657-668) or can be characterized by the manner in which the molecule rotates the plane of polarized light and is designated dextrorotatory or levorotatory (namely, as (+)- or (−)-isomers, respectively). A chiral compound can exist as either an individual enantiomer or as a mixture thereof. A mixture containing equal proportions of enantiomers is called a "racemic mixture".

In certain embodiments, the compounds disclosed herein can possess one or more asymmetric centers; and such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, stereoisomers of the compounds provided herein are depicted upon treatment with base.

In certain embodiments, the compounds disclosed herein are "stereochemically pure". A stereochemically pure compound has a level of stereochemical purity that would be recognized as "pure" by those of skill in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labelled compounds of the invention, such as those incorporating a radioactive isotope, may be useful in drug or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

Compounds that Inhibit β-Glucuronidase Activity

The present disclosure provides compounds and methods of inhibiting β-glucuronidase activity. Also described herein are methods of attenuating the side effects of one or more drugs comprising administration of the compounds described herein.

Drugs, agents, compounds or metabolites thereof which are substrates for β-glucuronidase (glucuronidase-substrate agents) can have their respective properties altered by glucuronidase hydrolysis. For example, if the drug, agent, compound or metabolite thereof has been metabolized to a glucuronide, the hydrolysis of the glucuronide can reactivate the drug, agent, compound or metabolite thereof. In many cases, this reactivation can cause adverse reactions, including but not limited to, gastrointestinal distress, leading to diarrhea.

For example, camptothecin-derived antineoplastic agents are useful for treating solid malignancies of the brain, colon and lung, as well as refractory forms of leukemia and lymphoma. Irinotecan is a prodrug that must be converted to its active form, SN-38 (7-ethyl-10-hydroxycamptohtecin), to have antineoplastic activity. During its excretion, SN-38 is glucuronidated to SN-38 glucuronide (SN-380) by drug metabolizing UDP-glucuronosyltranserases. As increasing amounts of the drug are administered to a subject, increased amounts of metabolites are therefore available as a substrate for β-glucuronidases. The resulting reactivated metabolites not only adversely affect a subject's well-being by causing serious side effects, particularly gastrointestinal distress, but also impair treatment outcome by limiting the amount of the glucuronidase-substrate agents that can be administered to the subject.

Another example of commonly used glucuronidase-substrate agents are non-steroidal anti-inflammatory agents (NSAIDs). Gastrointestinal Injury (GI) is one of the major adverse NSAIDs. This iatrogenic disease is manifested as ulceration and bleeding of the mucosa, inflammation, and even perforation (Allison et al., New Engl. J. Med, 327:749-754 (1992); Bjarnason et al., Gastroenterology, 104:1832-1847 (1993); Wolfe et al., New Engl. J. Med., 340:1888-1899 (1999)). A portion of the carboxylic acid-containing NSAIDs are conjugated with glucuronic acid in vivo and form acyl glucuronides. Although not wanting to be bound by this, it is believed that inhibition of carboxylic acid NSAID/glucuronic add deconjugation by inhibition of β-glucuronidase activity results in a reduced exposure of the intestinal mucosa to the NSAID and thereby reduces NSAID toxicity.

Thus, without intending to be bound by any particular theory, the compounds provided herein are thought to inhibit the interaction between β-glucuronidase and its substrate. Compounds contemplated by the disclosure include, but are not limited to, the exemplary compounds provided herein and salts thereof.

Compounds

One embodiment of the present invention is a compound of formula (IA):

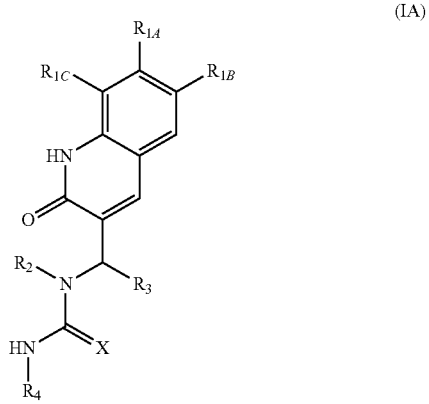

(IA)

wherein
each of $R_{1A}$, $R_{1B}$, $R_{1C}$ independently is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of formula (IAG):

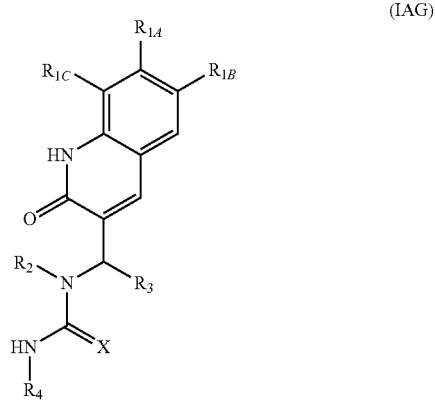

(IAG)

wherein
each of $R_{1A}$, $R_{1B}$, $R_{1C}$ independently is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, $C(O)R_d$, or

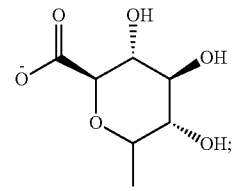

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One embodiment of the present invention is a compound of formula (IB):

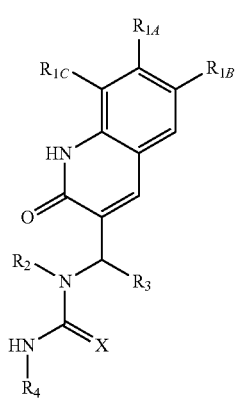

(IB)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_1$, $C_3$, $C_4$, $C_5$, or $C_6$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of formula (IBG):

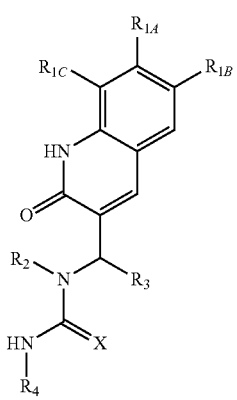

(IBG)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_1$, $C_3$, $C_4$, $C_5$, or $C_6$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, $C(O)R_d$, or

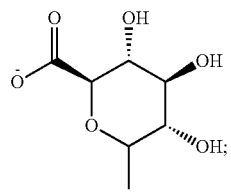

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One embodiment of the present invention is a compound of formula (IC):

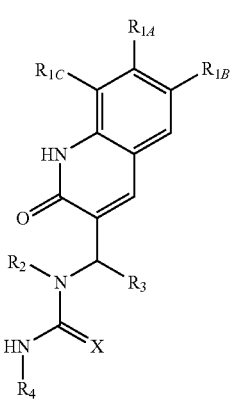

(IC)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of unsubstituted phenyl, or a substituted or unsubstituted 3- to 10-membered ring, having one or more heteroatoms selected from N, O, or S, and optionally having one or more degrees of unsaturation;

or a glucuronide thereof or a pharmaceutically acceptable salt thereof.

One embodiment of the present invention is a compound of formula (ICG):

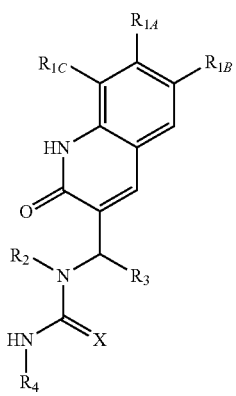

(ICG)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, $C(O)R_d$, or

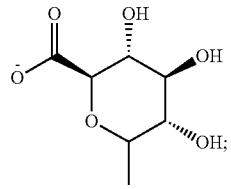

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of unsubstituted phenyl, or a substituted or unsubstituted 3- to 10-membered ring, having one or more heteroatoms selected from N, O, or S, and optionally having one or more degrees of unsaturation;

or a pharmaceutically acceptable salt thereof.

One embodiment of the present invention is a compound of formula (ID):

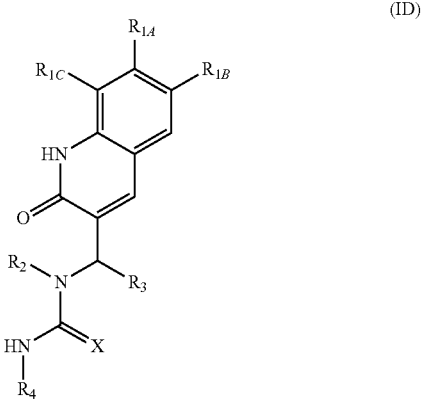

(ID)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O;

$R_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of formula (IDG):

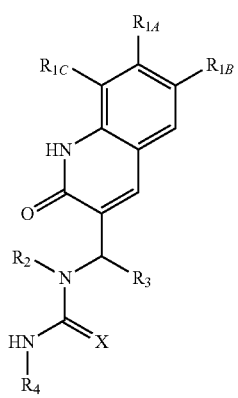

(IDG)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, $C(O)R_d$, or

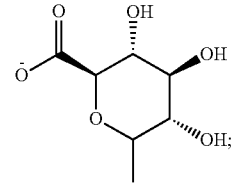

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O;

$R_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One embodiment of the present invention is a compound of formula (IE):

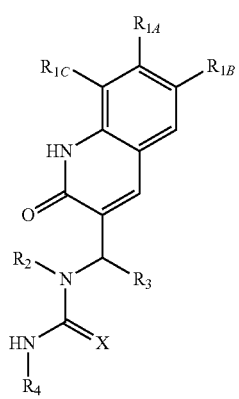

(IE)

wherein
each of $R_{1A}$, $R_{1B}$, $R_{1C}$ independently is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to IQ-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, $C(O)NHR_c$, or $C(O)R_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of formula (IEG):

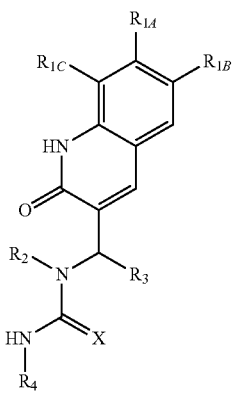

(IEG)

wherein
each of $R_{1A}$, $R_{1B}$, $R_{1C}$ independently is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, C(O)NHR$_c$, C(O)R$_d$, or

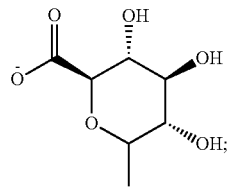

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One embodiment of the present invention is a compound of the formula (II):

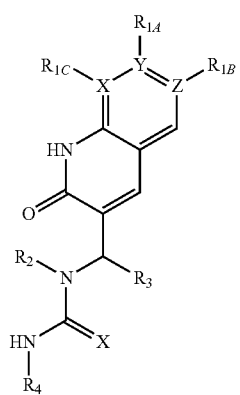

(II)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

each of X, Y or Z individually is C or N;

$R_2$ is $(L_1)_n R_a$, wherein $L_1$ is a $C_{1-6}$ alkylene chain, n is 0 or 1, and $R_a$ is OR$_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, C(O)NHR$_c$, or C(O)R$_d$;

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a glucuronide thereof;

or a pharmaceutically acceptable salt thereof.

One embodiment of the present invention is a compound of the formula (IIG):

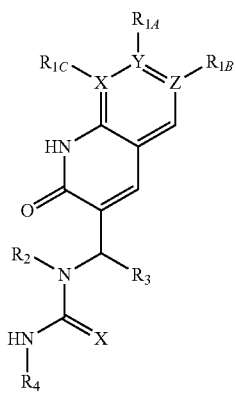
(IIG)

wherein each of $R_{1A}$, $R_{1B}$, $R_{1C}$ independently is hydrogen, substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

each of X, Y or Z individually is C or N;

$R_2$ is $(L_1)_n R_a$, wherein $L_1$ is a $C_{1-6}$ alkylene chain, n is 0 or 1, and $R_a$ is $OR_b$, $C_{1-6}$ alkylamino, or a substituted or unsubstituted 3- to 10-membered ring, optionally having one or more heteroatoms selected from N, O, or S, and optionally having one or more degrees of unsaturation;

$R_b$ is hydrogen, C(O)NHR_c, C(O)R_d or;

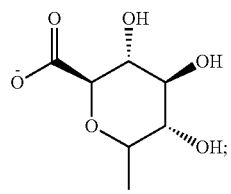

$R_c$ is aryl;

$R_d$ is substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{1-6}$ alkylaminoalkyl, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

$R_3$ is hydrogen substituted or unsubstituted $C_{1-6}$ alkyl, substituted or unsubstituted $C_{1-6}$ haloalkyl, substituted or unsubstituted $C_{1-6}$ alkoxy, substituted or unsubstituted $C_{1-6}$ alkylthio, substituted or unsubstituted $C_{1-6}$ haloalkoxy, substituted or unsubstituted $C_{1-6}$ haloalkylthio, substituted or unsubstituted $C_{1-6}$ alkylamino, substituted or unsubstituted $C_{2-6}$ alkenyl, substituted or unsubstituted $C_{2-6}$ haloalkenyl, substituted or unsubstituted $C_{2-6}$ alkynyl, substituted or unsubstituted $C_{2-6}$ haloalkynyl, halogen, cyano, nitro, or a substituted or unsubstituted 3- to 10-membered ring, optionally having one or more heteroatoms selected from N, O, or S, and optionally having one or more degrees of unsaturation;

X is O or S;

$R_4$ is selected from the group consisting of a substituted or unsubstituted 3- to 10-membered ring, optionally having one or more heteroatoms selected from N, O, or S, and optionally having one or more degrees of unsaturation;

or a pharmaceutically acceptable salt thereof.

One aspect of one or more embodiments of the present invention includes wherein $R_{1A}$ is selected from substituted $C_{1-6}$ alkyl or $C_{1-6}$ alkylaminoalkyl. One aspect of one or more embodiments of the present invention includes wherein the $C_{1-6}$ alkyl is substituted with (a) a substituted or unsubstituted 3- to 10-membered ring, optionally having one or more heteroatoms selected from N, O, or S, and optionally having one or more degrees of unsaturation, or (b) $OC(O)R_x$, wherein $R_x$ is $C_{1-6}$ alkyl.

One aspect of one or more embodiments of the present invention includes wherein $R_2$ is $(L_1)_n R_a$, wherein $L_1$ is a $C_2$ alkylene, n is 1, and $R_a$ is $OR_b$, wherein $R_b$ is hydrogen.

One aspect of one or more embodiments of the present invention includes wherein $R_2$ is $(L_1)_n R_a$, n is 0, and $R_a$ is a substituted or unsubstituted 3- to 10-membered ring, optionally having one or more heteroatoms selected from N, O, or S, and optionally having one or more degrees of unsaturation.

One aspect of one or more embodiments of the present invention includes wherein $R_{1A}$ is substituted $C_{1-6}$ alkyl; $R_2$ is $(L_1)_n R_a$, wherein $L_1$ is a $C_2$ alkylene, n is 1, and $R_a$ is $OR_b$, wherein $R_b$ is hydrogen; and X is S. One aspect of one or more embodiments of the present invention includes wherein the $C_{1-6}$ alkyl is substituted with (a) a substituted or unsubstituted 3- to 10-membered ring, optionally having one or more heteroatoms selected from N, O, or S, and optionally having one or more degrees of unsaturation, or (b) $OC(O)R_x$, wherein $R_x$ is $C_{1-6}$ alkyl.

One aspect of one or more embodiments of the present invention includes wherein $R_{1A}$ is $C_{1-6}$ alkylaminoalkyl; and $R_2$ is $(L_1)_n R_a$, wherein $L_1$ is a $C_2$ alkylene, n is 1, and $R_a$ is $OR_b$, wherein $R_b$ is hydrogen.

One aspect of one or more embodiments of the present invention includes wherein $R_{1A}$ is $C_{1-6}$ alkylaminoalkyl; and $R_2$ is $(L_1)_n R_a$, wherein n is 0, and $R_a$ is a substituted or unsubstituted 3- to 10-membered ring, optionally having one or more heteroatoms selected from N, O, or S, and optionally having one or more degrees of unsaturation.

One aspect of one or more embodiments of the present invention includes wherein $R_1$ is $C_{1-6}$ alkylaminoalkyl, and $R_2$ is $(L_1)_n R_a$, wherein n is 0, and $R_a$ is a substituted or unsubstituted 3- to 10-membered ring, optionally having one or more heteroatoms selected from N, O, or S, and optionally having one or more degrees of unsaturation; and X is O.

One aspect of one or more embodiments of the present invention includes wherein $R_2$ is $C(O)R_d$, and wherein $R_d$ is $C_{1-6}$ alkyl or a substituted or unsubstituted 3- to 10-membered ring, optionally having one or more heteroatoms selected from N, O, or S, and optionally having one or more degrees of unsaturation.

One aspect of one or more embodiments of the present invention includes wherein: each of $R_{1A}$, $R_{1B}$ and $R_{1C}$ independently is hydrogen or $C_{1-6}$ alkyl; $R_2$ is $(L_1)_nR_a$, wherein $L_1$ is a $C_2$ alkylene, n is 1, and $R_a$ is $OR_b$, wherein $R_b$ is hydrogen; $R_3$ is hydrogen, a substituted or unsubstituted $C_{1-6}$ alkyl, or a substituted or unsubstituted 3- to 10-membered ring, optionally having one or more heteroatoms selected from N, O, or S, and optionally having one or more degrees of unsaturation; $R_4$ is a substituted or unsubstituted 6-membered ring, optionally having one or more heteroatoms selected from N, O, or S, and optionally having one or more degrees of unsaturation. One aspect of one or more embodiments of the present invention includes wherein: $R_{1A}$ is hydrogen; each of $R_{1B}$ and $R_{1C}$ is methyl; $R_3$ is hydrogen, $C_{1-6}$ alkyl, or $C_{3-10}$ cycloalkyl; and $R_4$ is a substituted or unsubstituted phenyl or pyridyl.

One aspect of one or more embodiments of the present invention includes wherein $R_3$ is $C_{1-6}$ alkyl or a substituted or unsubstituted 3- to 10-membered ring, optionally having one or more heteroatoms selected from N, O, or S, and optionally having one or more degrees of unsaturation.

One aspect of one or more embodiments of the present invention includes wherein $R_3$ is $C_{1-6}$ alkyl or $C_{3-10}$ cycloalkyl.

One embodiment of the present invention includes a compound selected from the group consisting of:
[3-[[(4-ethoxyphenyl)carbamothioyl-(2-hydroxyethyl)amino]methyl]-6,8-dimethyl-2-oxo-1H-quinolin-7-yl]methyl acetate;
1-[[6,8-dimethyl-7-[(4-methylpiperazin-1-yl)methyl]-2-oxo-1H-quinolin-3-yl]methyl]-3-(4-ethoxyphenyl)-1-(2-hydroxyethyl)thiourea;
1-[[6,8-dimethyl-7-[(4-methylpiperazin-1-yl)methyl]-2-oxo-1H-quinolin-3-yl]methyl]-3-(4-ethoxyphenyl)-1-(2-hydroxyethyl)urea;
1-[[7-(diethylaminomethyl)-6,8-dimethyl-2-oxo-1H-quinolin-3-yl]methyl]-3-(4-ethoxyphenyl)-1-(2-hydroxyethyl)thiourea;
1-[[7-(diethylaminomethyl)-6,8-dimethyl-2-oxo-1H-quinolin-3-yl]methyl]-3-(4-ethoxy phenyl)-1-(2-hydroxyethyl)urea;
tert-butyl-3-[[7-(diethylaminomethyl)-6,8-dimethyl-2-oxo-1H-quinolin-3-yl]methyl-[(4-ethoxyphenyl)carbamoyl]amino]pyrrolidine-1-carboxylate;
1-[[7-(diethylaminomethyl)-6,8-dimethyl-2-oxo-1H-quinolin-3-yl]methyl]-3-(4-ethoxyphenyl)-1-pyrrolidin-3-yl-thiourea;
1-[[7-(diethylaminomethyl)-6,8-dimethyl-2-oxo-1H-quinolin-3-yl]methyl]-3-(4-ethoxyphenyl)-1-pyrrolidin-3-yl-urea;
tert-butyl 3-[[7-(diethylaminomethyl)-6,8-dimethyl-2-oxo-1H-quinolin-3-yl]methyl-[(4-ethoxyphenyl)carbamothioyl]amino]azetidine-1-carboxylate;
tert-butyl 3-[[7-(diethylaminomethyl)-6,8-dimethyl-2-oxo-1H-quinolin-3-yl]methyl-[(4-ethoxy phenyl)carbamoyl]amino]azetidine-1-carboxylate;
1-(azetidin-3-yl)-1-[[7-(diethylaminomethyl)-6,8-dimethyl-2-oxo-1H-quinolin-3-yl]methyl]-3-(4-ethoxyphenyl)thiourea;
1-(azetidin-3-yl)-1-[[7-(diethylaminomethyl)-6,8-dimethyl-2-oxo-1H-quinolin-3-yl]methyl]-3-(4-ethoxyphenyl)urea;
1-[[7-(diethylaminomethyl)-6,8-dimethyl-2-oxo-1H-quinolin-3-yl]methyl]-3-(4-ethoxyphenyl)-1-(3-hydroxycyclobutyl)thiourea;
1-[[7-(diethylaminomethyl)-6,8-dimethyl-2-oxo-1H-quinolin-3-yl]methyl]-3-(4-ethoxyphenyl)-1-(3-hydroxycyclobutyl)urea;
1-[[6,8-dimethyl-7-(morpholinomethyl)-2-oxo-1H-quinolin-3-yl]methyl]-3-(4-ethoxyphenyl)-1-(2-hydroxyethyl)urea; and
1-[[6,8-dimethyl-7-(morpholinomethyl)-2-oxo-1H-quinolin-3-yl]methyl]-3-(4-ethoxyphenyl)-1-(2-hydroxyethyl)thiourea;

or a pharmaceutically acceptable salt thereof.

One embodiment of the present invention includes a compound selected from the group consisting of:

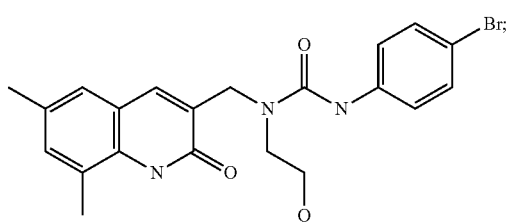

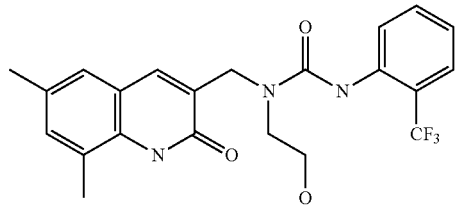

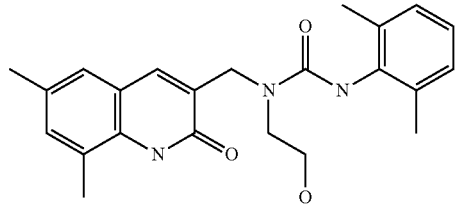

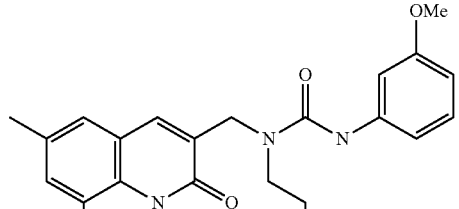

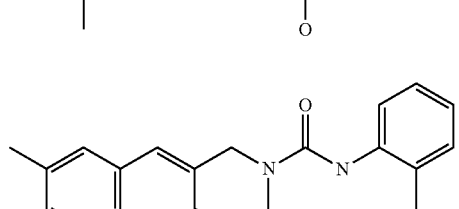

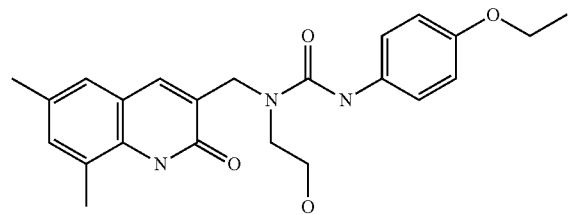
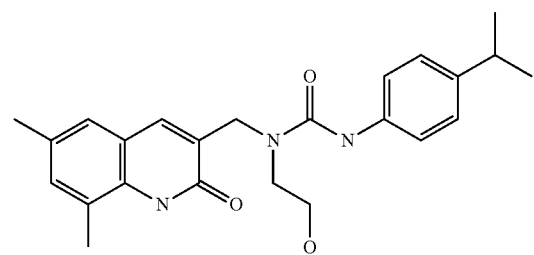
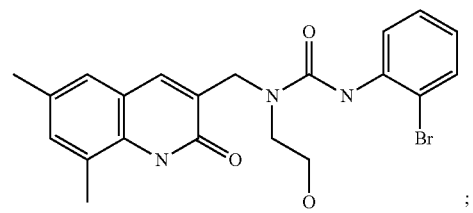
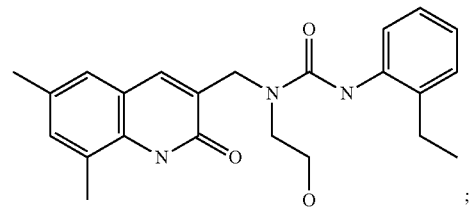
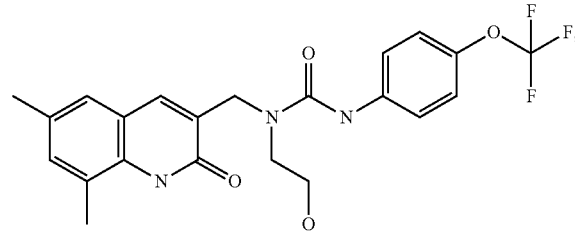
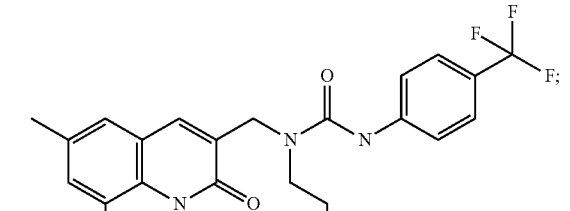
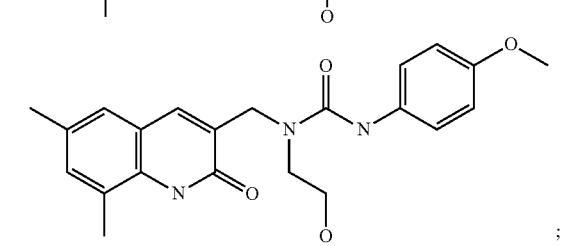
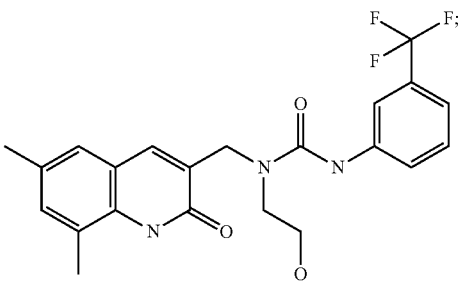
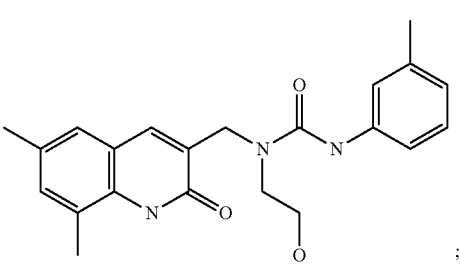
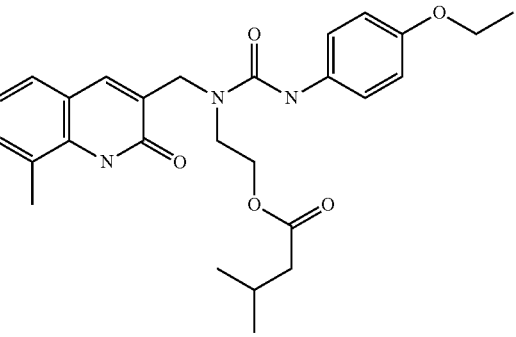
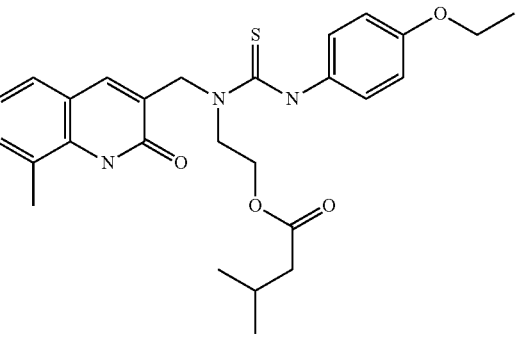
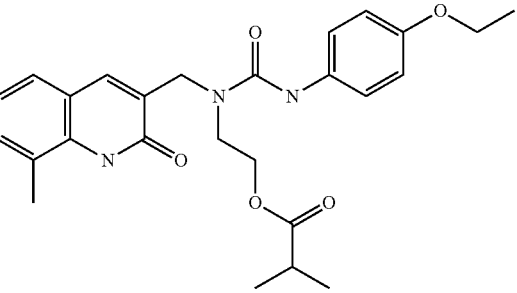

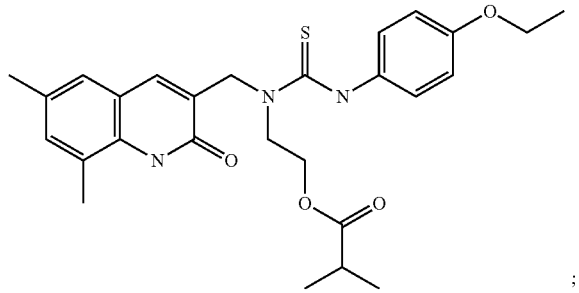

or a pharmaceutically acceptable salt thereof.

One embodiment of the present invention includes a compound selected from the group consisting of:
3-(2-Bromophenyl)-1-[(6,8-dimethyl-2-oxo-1H-quinolin-3-yl)methyl]-1-(2-hydroxyethyl)urea;
1-[(6,8-dimethyl-2-oxo-1H-quinolin-3-yl)methyl]-1-(2-hydroxyethyl)-3-(2-isopropylphenyl)urea;
1-[(6,8-dimethyl-2-oxo-1H-quinolin-3-yl)methyl]-1-(2-hydroxyethyl)-3-(2-phenylphenyl)urea;
1-[(6,8-dimethyl-2-oxo-1H-quinolin-3-yl)methyl]-1-(2-hydroxyethyl)-3-(3-pyridyl)urea;
1-[(6,8-dimethyl-2-oxo-1H-quinolin-3-yl)methyl]-1-(2-hydroxyethyl)-3-(2-iodophenyl)urea;
1-[(6,8-dimethyl-2-oxo-1H-quinolin-3-yl)methyl]-3-(4-fluoro-2-iodo-phenyl)-1-(2-hydroxyethyl)urea;
1-[1-(6,8-dimethyl-2-oxo-1H-quinolin-3-yl)ethyl]-1-(2-hydroxyethyl)-3-(3-methoxyphenyl)urea;
1-[(6,8-dimethyl-2-oxo-1H-quinolin-3-yl)methyl]-1-(2-hydroxyethyl)-3-(m-tolyl)urea;
1-[(6,8-dimethyl-2-oxo-1H-quinolin-3-yl)methyl]-1-(2-hydroxyethyl)-3-(3-isopropylphenyl)urea;
1-[(6,8-dimethyl-2-oxo-1H-quinolin-3-yl)methyl]-1-(2-hydroxyethyl)-3-[4-methyl-2-(2-trimethylsilylethynyl)phenyl]urea;
1-[(6,8-dimethyl-2-oxo-1H-quinolin-3-yl)methyl]-3-(2-ethynyl-4-fluoro-phenyl)-1-(2-hydroxyethyl)urea;
1-[1-(6,8-dimethyl-2-oxo-1H-quinolin-3-yl)ethyl]-1-(2-hydroxyethyl)-3-(2-isopropylphenyl)urea;
1-[1-(6,8-dimethyl-2-oxo-1H-quinolin-3-yl)ethyl]-3-(4-fluoro-2-iodo-phenyl)-1-(2-hydroxyethyl)urea;
1-[1-(6,8-dimethyl-2-oxo-1H-quinolin-3-yl)ethyl]-1-(2-hydroxyethyl)-3-(o-tolyl)urea; and
1-[1-(6,8-dimethyl-2-oxo-1H-quinolin-3-yl)ethyl]-1-(2-hydroxyethyl)-3-(4-methoxyphenyl)urea;
or a pharmaceutically acceptable salt thereof.

Compositions that Inhibit β-Glucuronidase Activity

One embodiment described in the present disclosure provides compositions that inhibit β-glucuronidase activity. Generally, the compositions that inhibit β-glucuronidase activity in humans and animals will comprise a pharmaceutically acceptable excipient or diluent and a compound having the formula provided above as formula (I).

In one embodiment described herein is a composition comprising one or more compounds as described herein and one or more pharmaceutically acceptable carriers.

The term "composition" as used herein is intended to encompass a product comprising specific ingredients in specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this disclosure may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Pat. No. 6,451,339, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil in water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent a preservative, and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present disclosure are employed. As used herein, topical application is also meant to include the use of mouth washes and gargles. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for parenteral administration include aqueous and non-aqueous sterile injection solutions, which may contain anti-oxidants, buffers, bacteriostats and solutes, which render the formulation isotonic with the blood of the intended recipient; and aqueous and non-aqueous sterile suspensions which may include suspending agents and thickening agents.

Formulations for rectal administration may be presented as a suppository with a suitable base comprising for example cocoa butter or a salicylate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments, a preferred pharmaceutical composition includes one or more of the presently disclosed compounds and one or more chemotherapeutic agent.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Methods of Inhibiting β-Glucuronidase Activity and Attenuating Side Effects from Drugs In yet another aspect, the present disclosure provides methods of attenuating the side effects of one or more drugs comprising administering to a subject an effective amount of one or more compounds of formula (I) as described herein. Compounds for use in the present methods include those compounds according to formula (I), those provided above as embodiments, those specifically exemplified in the Examples below, and those provided with specific structures herein.

In one embodiment described herein is a method for attenuating the side effects of one or more drug comprising administering to a subject an effective amount of one or more of any of the compounds described herein. In one aspect of the embodiment, the compounds described herein selectively inhibit β-glucuronidase. In one aspect described herein, the compounds can be co-administered with one or more drug.

The pharmaceutical compositions and methods of the present disclosure may further comprise other therapeutically active compounds as noted herein, including but not limited to treatment of 1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout (13) immune mediated food allergies such as Coeliac (Celiac) disease (14) pulmonary fibrosis and other fibrotic diseases, and (15) irritable bowel syndrome.

In another group of embodiments, diseases or conditions that induce side effects that can be treated with β-glucuronidase inhibitor compound include but are not limited to cancers, including but not limited to, carcinoma, lymphoma, blastoma, sarcoma, and leukemia or lymphoid malignancies.

More particular examples of such cancers include melanoma, squamous cell cancer (e.g., epithelial squamous cell cancer), lung cancer including melanoma, multiple myeloma, small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, glioblastoma multiforme, KRAS mutant solid tumors, indolent non-Hodgkin's lymphoma, chronic lymphocytic leukemia (CLL), diffuse large B-cell lymphoma, thyroid cancer, non-Hodgkin's lymphoma, basal cell carcinoma, hematological tumors, B-cell non-Hodgkin's lymphoma, acute myeloid leukemia (AML), cervical cancer, ovarian cancer, liver cancer, bladder cancer, hepatoma, breast cancer, including triple negative breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Also included are "hematological malignancies" or "hematological cancer," which are the types of cancer that affect blood, bone marrow, and lymph nodes. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes), cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions, chronic inflammation, autoimmune diseases such as rheumatoid arthritis and immune-mediated food allergies such as Coelaic disease.

Another embodiment described herein include methods for improving the treatment of a variety of diseases including neoplasms of the bone, brain, breast cervix, colon, intestines, kidney, liver, lung, pancreatic, prostate, rectum, stomach, throat, uterus, and the like.

Another embodiment described herein include methods for improving the efficacy of other drugs including but not limited to: chemotherapeutic drugs including but not limited to camptothecin, indolizino, irinotecan, diflomotecan, exatecan, gimatecan, irinotecan, karenitecin, lurtorecan, rubitecan, silatecan, topotecan, NSAIDs, sorafenib, alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); anti-androgens such as flutamide, nilutamide, bicalutamide, leuprolide, and goserelin; as well as troxacitabine (a 1,3-dioxolane nucleoside cytosine analog); (iv) protein kinase inhibitors; lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID® PROLEUKIN® rIL-2; a topoisomerase 1 inhibitor such as LURTOTECAN® ABARELIX® rmRH; (ix) anti-angiogenic agents such as bevacizumab (AVASTIN®, Genentech); and (x) pharmaceutically acceptable salts, acids and derivatives of any of the above; NSAIDs including but not limited to salicylates, p-amino phenol derivatives, propionic acid derivatives, carboxylic acid derivatives, enolic acid derivatives, fenamic acid derivatives, sulphonanilides, and selective COX-2 inhibitors. "NSAID salicylates" include, but are not limited to, aspirin (acetylsalicylic acid), diflunisal, and salsalate. "NSAID p-amino phenol derivatives" include, but are not limited to, paracetamol and phenacetin. "NSAID propionic acid derivatives" include, but are not limited to, ibuprofen, naproxen, fenoprofen, ketoprofen, dexketoprofen, fluribiprofen, oxaprozin, and loxoprofen. "NSAID carboxylic acid derivatives" include, but are not limited to, indomethadn, sulindac, etodolac, ketorolac, diclofenac. NSAID carboxylic acid derivatives include NSAID acetic acid derivatives. NSAID carboxylic acid derivatives are also referred to herein as "carboxylic acid NSAIDs." "NSAID enolic acid derivatives" include, but are not limited to, piroxicam, meloxicam, tenoxicam, droxicam, lomoxicam, and isoxicam. "NSAID fenamic acid derivatives" include, but are not limited to, mefenamic acid, medofenamic add, flufenamic add, and tolfenamic add. "NSAID sulphonanilides" include, but are not limited to, nimesulide. "NSAID selective COX-2 inhibitors" include, but are not limited to, celecoxib, rofecoxib, valdecoxib, parecoxib, lumiracoxib, etoricoxib, and firocoxib; antibiotics including not limited to cephalosporins such as cefixime and cefpodoxime, clindamycin, penicillins, fluoroquinolones such as ciprofloxacin and levofloxacin, the enediyne antibiotics (e. g., calicheamicin, especially calicheamicin gamma1I and calicheamicin omega1I (see, e.g., Nicolaou et al., *Angew. Chem Inti. Ed. Engl.,* 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic add analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; anti-adrenals such as aminoglutethimide, mitotane, trilostane; folic add replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paditaxel (TAXOL®), albumin-engineered nanoparticle formulation of paditaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, adds or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; EGFR inhibitor such as erlotinib or cetuximab; an anti-VEGF inhibitor such as bevacizumab; arinotecan; rmRH (e.g., ABARELIX®); 17AAG (geldanamycin derivative that is a heat shock protein (Hsp) 90 poison), and pharmaceutically acceptable salts, acids or derivatives of any of the above; anti-hormonal agents that act to regulate, reduce, block, or inhibit the effects of hormones that can promote the growth of cancer, and are often in the form of systemic, or whole-body treatment They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/ zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); immunosuppressants and anti-rejection drugs including but not limited to tacrolimus and cyclosporine, mycophenolate mofetil, mycophenolate sodium, azathioprine, sirolimus and prednisone; other β-glucuronidase substrate drugs including but not limited to morphine, paracetamol, oxazepam, androsterone, carbamazepine, codeine, lamotrigine, lorazepam, temazepam, testosterone, and zidovudine.

Preparation of the β-Glucuronidase Inhibitors

The following examples are offered to illustrate, but not to limit, the claimed disclosure.

Additionally, those skilled in the art will recognize that the molecules claimed in this patent may be synthesized using a variety of standard organic chemistry transformations. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Certain general reaction types employed widely to synthesize target compounds in this disclosure are summarized in the examples. Specifically, generic procedures for sulfonamide formation, pyridine N-oxide formation and 2-aminophenyl-arylmethanone synthesis via Friedel-Crafts type approaches are given, but numerous other standard chemistries are described within and were employed routinely.

While not intended to be exhaustive, representative synthetic organic transformations which can be used to prepare compounds of the disclosure are included below.

These representative transformations include; standard functional group manipulations; reductions such as nitro to amino; oxidations of functional groups including alcohols and pyridines; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buckwald, Suzuki and Sonigashira reactions; halogenations and other electrophilic aromatic substitution reactions; diazonium salt formations and reactions of these species; etherifications; cydative condensations, dehydrations, oxidations and reductions leading to heteroaryl groups; aryl metallations and transmetallations and reaction of the ensuing aryl-metal species with an electrophile such as an add chloride or Weinreb amide; amidations; esterifications; nudeophilic substitution reactions; alkylations; acylations; sulfonamide formation; chlorosulfonylations; ester and related hydrolyses, and the like.

Certain molecules claimed in this patent can exist in different enantiomeric and diastereomeric forms and all such variants of these compounds are within the scope of the disclosure.

In the descriptions of the syntheses that follow, some precursors were obtained from commercial sources. These commercial sources include Aldrich Chemical Co., A eras Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the present disclosure can be made by the methods and approaches described in the following experimental section and by the use of standard organic chemistry transformations that are well known to those skilled in the art.

EXAMPLES

The present disclosure explicitly encompasses those compounds presented in Table 1. A composition comprising a therapeutically acceptable amount of any of these compounds is also within the scope of the invention. The compounds of Table 1 may be synthesized using the techniques described and exemplified herein.

TABLE 1

| Reference No. | Compound Name | Compound Structure |
|---|---|---|
| Ref #1 | 1-((6,8-dicyclopropyl-2-oxo-1,2-dihydroquinolin-3-yl)methyl)-3-(4-ethoxyphenyl)-1-(2-hydroxyethyl)urea | 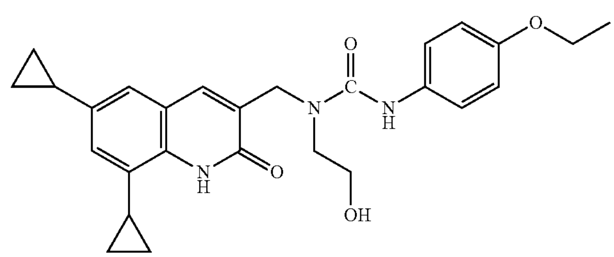 [SMILES: CCOc1ccc(NC(=O)N(CCO)Cc2cc3cc(C4CC4)cc(C4CC4)c3[nH]c2=O)cc1] |
| Ref #2 | 1-((8-cyclopropyl-6-methyl-2-oxo-1,2-dihydroquinolin-3-yl)methyl)-3-(4-ethoxyphenyl)-1-(2-hydroxyethyl)urea | 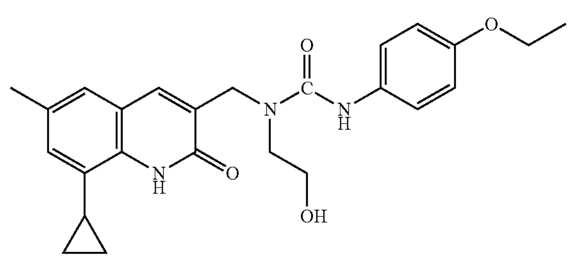 [SMILES: CCOc1ccc(NC(=O)N(CCO)Cc2cc3cc(C)cc(C4CC4)c3[nH]c2=O)cc1] |
| Ref #3 | 1-(1-(6,8-dimethyl-2-oxo-1,2-dihydroquinolin-3-yl)ethyl)-3-(4-ethoxyphenyl)-1-(2-hydroxyethyl)urea | 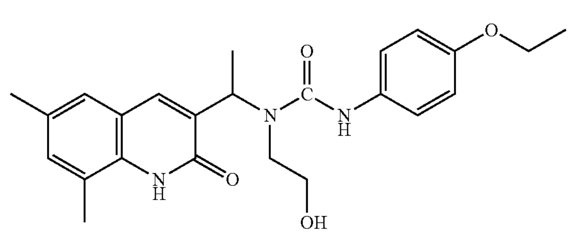 [SMILES: CCOc1ccc(NC(=O)N(CCO)C(C)c2cc3cc(C)cc(C)c3[nH]c2=O)cc1] |

TABLE 1-continued

| Reference No. | Compound Name | Compound Structure |
|---|---|---|
| Ref #4 | 3-(4-ethoxyphenyl)-1-(2-hydroxyethyl)-1-((2-oxo-6,8-bis(trifluoromethyl)-1,2-dihydroquinolin-3-yl)methyl)urea | 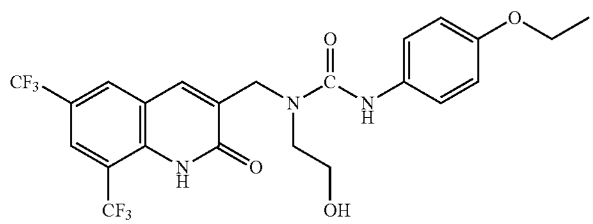 [SMILES: CCOc1ccc(NC(=O)N(CCO)Cc2cc3cc(C(F)(F)F)cc(C(F)(F)F)c3[nH]c2=O)cc1] |
| Ref #5 | 3-(4-ethoxyphenyl)-1-(2-hydroxyethyl)-1-(1-(2-oxo-6,8-bis(trifluoromethyl)-1,2-dihydroquinolin-3-yl)ethyl)urea | 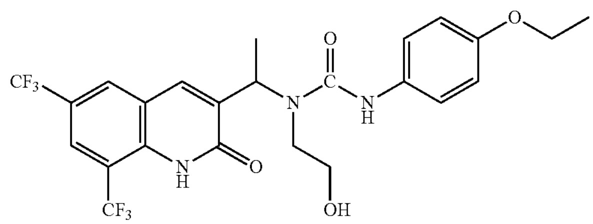 [SMILES: CCOc1ccc(NC(=O)N(CCO)C(C)c2cc3cc(C(F)(F)F)cc(C(F)(F)F)c3[nH]c2=O)cc1] |
| Ref #6 | 1-(1-(6,8-dimethyl-2-oxo-1,2-dihydroquinolin-3-yl)propyl)-3-(4-ethoxyphenyl)-1-(2-hydroxyethyl)urea | 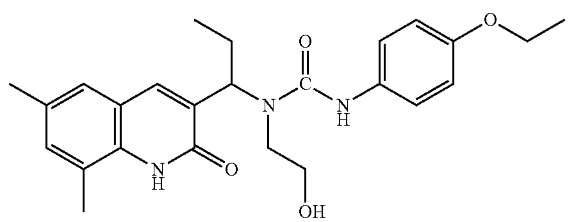 [SMILES: CCOc1ccc(NC(=O)N(CCO)C(CC)c2cc3cc(C)cc(C)c3[nH]c2=O)cc1] |
| Ref #7 | 1-((6,8-dimethyl-2-oxo-1,2-dihydroquinolin-3-yl)methyl)-1-(2-hydroxyethyl)-3-(4-(2,2,2-trifluoroethoxy)phenyl)urea | 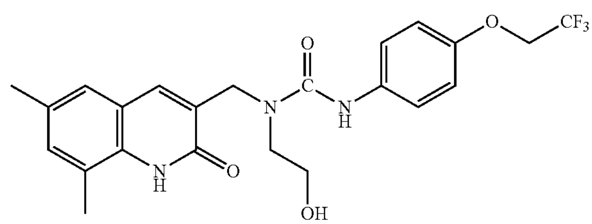 [SMILES: Cc1cc(C)c2[nH]c(=O)c(CN(CCO)C(=O)Nc3ccc(OCC(F)(F)F)cc3)cc2c1] |
| Ref #8 | 1-((6,8-dimethyl-2-oxo-1,2-dihydroquinolin-3-yl)methyl)-1-(2-hydroxyethyl)-3-(4-(trifluoromethoxy)phenyl)urea | 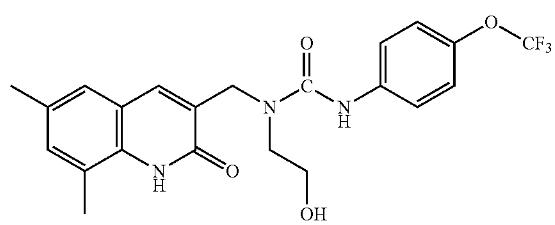 [SMILES: Cc1cc(C)c2[nH]c(=O)c(CN(CCO)C(=O)Nc3ccc(OC(F)(F)F)cc3)cc2c1] |
| Ref #9 | 3-(benzo[d]oxazol-5-yl)-1-((6,8-dimethyl-2-oxo-1,2-dihydroquinolin-3-yl)methyl)-1-(2-hydroxyethyl)urea | 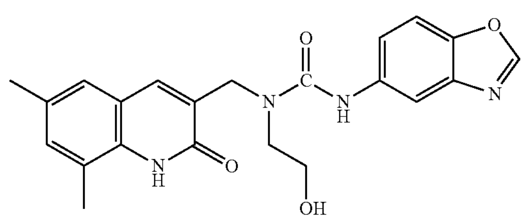 [SMILES: Cc1cc(C)c2[nH]c(=O)c(CN(CCO)C(=O)Nc3ccc4ocnc4c3)cc2c1] |
| Ref #10 | 3-(chroman-6-yl)-1-((6,8-dimethyl-2-oxo-1,2-dihydroquinolin-3-yl)methyl)-1-(2-hydroxyethyl)urea | 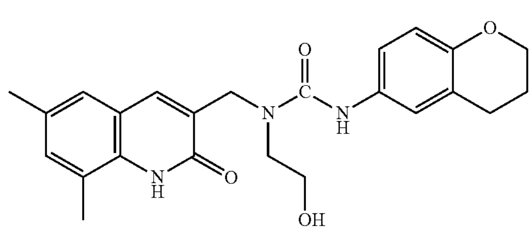 [SMILES: Cc1cc(C)c2[nH]c(=O)c(CN(CCO)C(=O)Nc3ccc4c(c3)CCCO4)cc2c1] |

TABLE 1-continued

| Reference No. | Compound Name | Compound Structure |
|---|---|---|
| Ref #11 | 3-(2,3-dihydrobenzo[b][1,4]dioxin-6-yl)-1-((6,8-dimethyl-2-oxo-1,2-dihydroquinolin-3-yl)methyl)-1-(2-hydroxyethyl)urea | 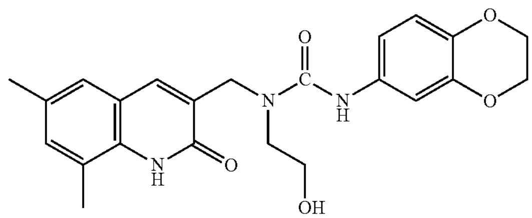 [SMILES: Cc1cc(C)c2[nH]c(=O)c(CN(CCO)C(=O)Nc3ccc4c(c3)OCCO4)cc2c1] |
| Ref #12 | 1-((6,8-dimethyl-2-oxo-1,2-dihydroquinolin-3-yl)methyl)-1-(2-hydroxyethyl)-3-(pyridin-4-yl)urea | 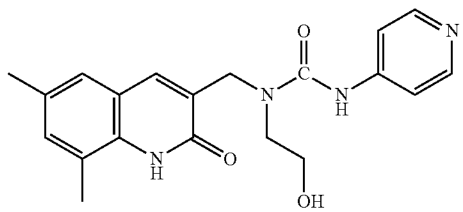 [SMILES: Cc1cc(C)c2[nH]c(=O)c(CN(CCO)C(=O)Nc3ccncc3)cc2c1] |
| Ref #13 | 3-(4-ethoxyphenyl)-1-(2-hydroxyethyl)-1-((6-methyl-2-oxo-1,2-dihydro-1,7-naphthyridin-3-yl)methyl)urea | 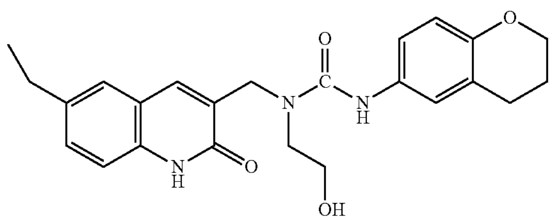 [SMILES: CCc1ccc2[nH]c(=O)c(CN(CCO)C(=O)Nc3ccc4c(c3)CCCO4)cc2c1] |
| Ref #14 | 1-((6,8-dimethyl-2-oxo-1,2-dihydroquinolin-3-yl)methyl)-1-(2-hydroxyethyl)-3-(4-(trifluoromethyl)phenyl)urea | 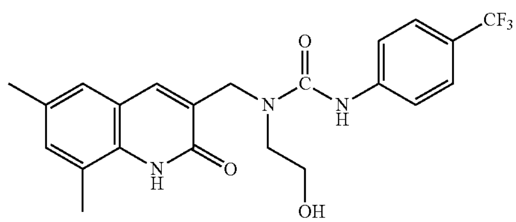 [SMILES: Cc1cc(C)c2[nH]c(=O)c(CN(CCO)C(=O)Nc3ccc(C(F)(F)F)cc3)cc2c1] |
| Ref #15 | 1-((6,8-dimethyl-2-oxo-1,2-dihydroquinolin-3-yl)methyl)-3-(4-ethoxy-3-fluorophenyl)-1-(2-hydroxyethyl)urea | 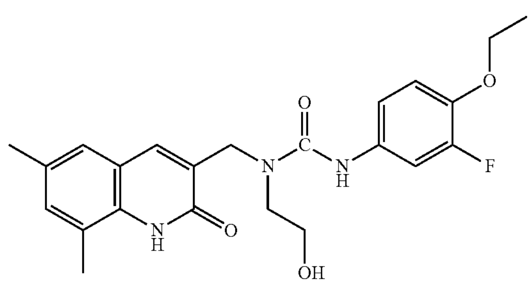 [SMILES: CCOc1ccc(NC(=O)N(CCO)Cc2cc3cc(C)cc(C)c3[nH]c2=O)cc1F] |
| Ref #16 | 4-(3-((6,8-dimethyl-2-oxo-1,2-dihydroquinolin-3-yl)methyl)-3-(2-hydroxyethyl)ureido)benzamide | 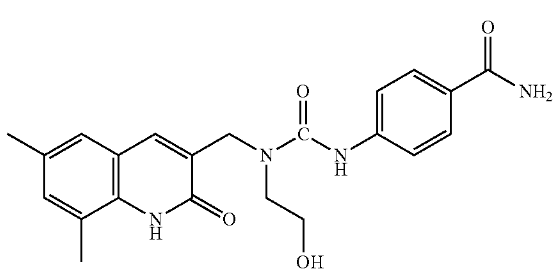 [SMILES: Cc1cc(C)c2[nH]c(=O)c(CN(CCO)C(=O)Nc3ccc(C(N)=O)cc3)cc2c1] |

TABLE 1-continued

| Reference No. | Compound Name | Compound Structure |
|---|---|---|
| Ref #17 | 1-((6,8-dimethyl-2-oxo-7-(trifluoromethyl)-1,2-dihydroquinolin-3-yl)methyl)-1-(2-hydroxyethyl)-3-(4-(2,2,2-trifluoroethoxy)phenyl)urea | 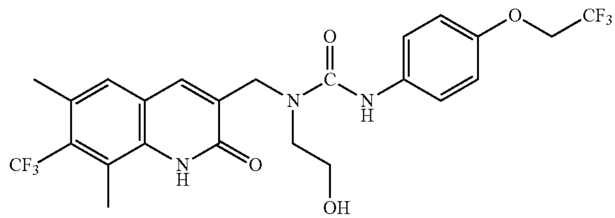 [SMILES: Cc1cc2cc(CN(CCO)C(=O)Nc3ccc(OCC(F)(F)F)cc3)c(=O)[nH]c2c(C)c1C(F)(F)F] |
| Ref #18 | 1-((6,7-dimethyl-2-oxo-1,2-dihydroquinolin-3-yl)methyl)-1-(2-hydroxyethyl)-3-(4-(2,2,2-trifluoroethoxy)phenyl)urea | 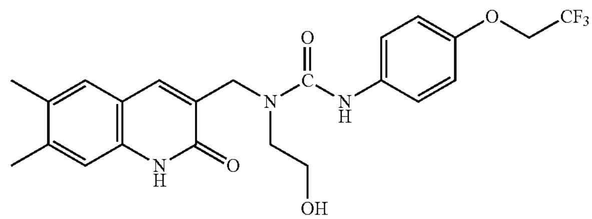 [SMILES: Cc1cc2cc(CN(CCO)C(=O)Nc3ccc(OCC(F)(F)F)cc3)c(=O)[nH]c2cc1C] |
| Ref #19 | 1-((6-bromo-8-chloro-2-oxo-1,2-dihydroquinolin-3-yl)methyl)-3-(4-ethoxyphenyl)-1-(2-hydroxyethyl)urea | 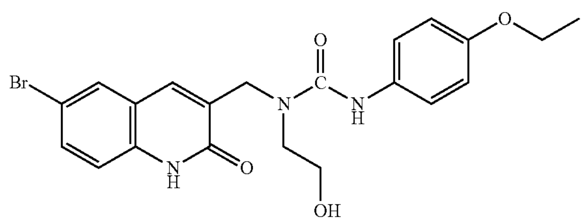 [SMILES: CCOc1ccc(NC(=O)N(CCO)Cc2cc3cc(Br)ccc3[nH]c2=O)cc1] |
| Ref #20 | 1-((6,8-dichloro-2-oxo-1,2-dihydroquinolin-3-yl)methyl)-1-(2-hydroxyethyl)-3-(4-methoxyphenyl)urea | 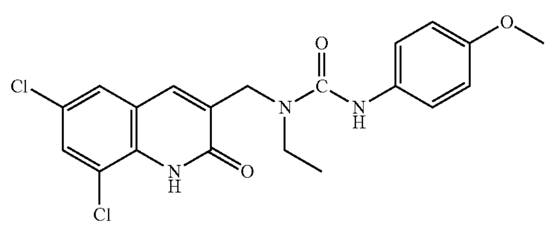 [SMILES: CCN(Cc1cc2cc(Cl)cc(Cl)c2[nH]c1=O)C(=O)Nc1ccc(OC)cc1] |

Examples of Compound Synthesis

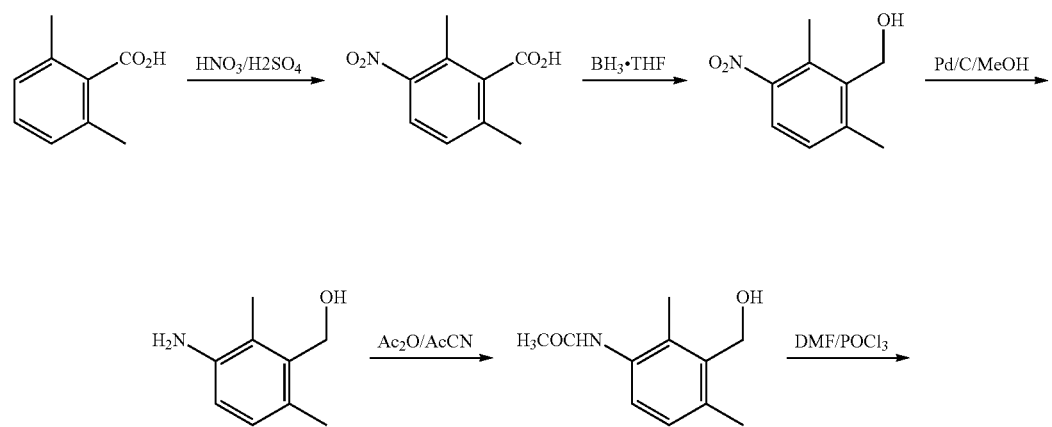

Synthesis Scheme 1

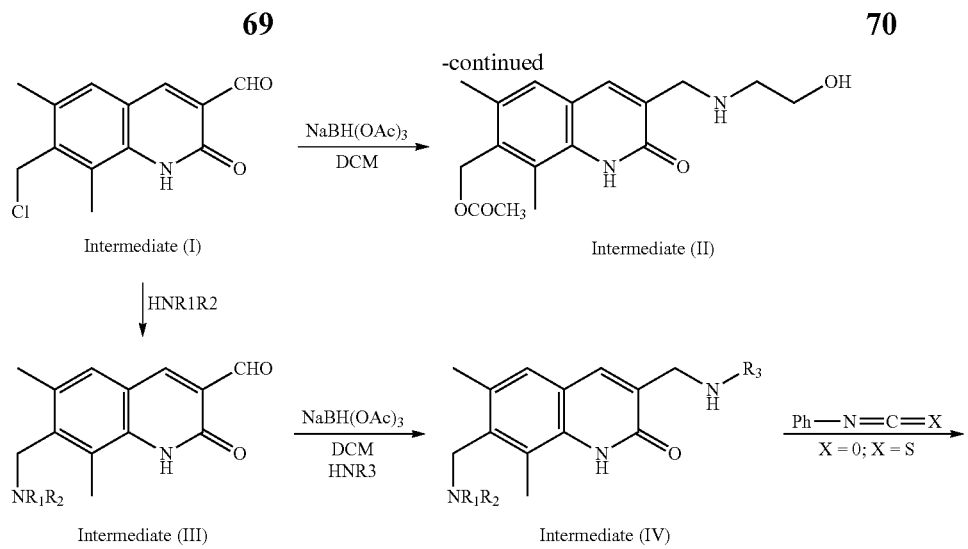

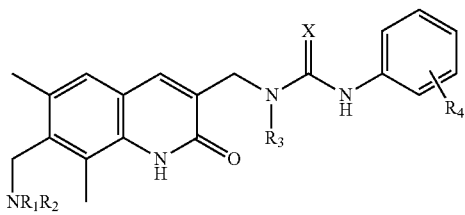

2,6-dimethylbenzoic acid was treated with nitric acid/sulfuric acid to afford the nitro compound which was then subjected to borane reduction to provide the alcohol. The nitro group was then reduced and then acetylated tp provide the N-acetyl derivative. The N-acetylated compound was then subjected to DMF/POCl3 conditions to directly provide 7-(chloromethyl)-6,8-dimethyl-2-oxo-1H-quinoline-3-carbaldehyde (I). Intermediate (I) was then treated with ethanol amine to afford intermediate (II) or treated with various amines to afford intermediate (III). Intermediate (III) was subjected to reductive amination with various amines to afford intermediate (IV). Intermediate (IV) was then reacted with various isocyanates or isothiocyanates to provide the final compounds (V).

Synthesis Scheme 2
Scheme for Inh-1 glucuronide synthesis

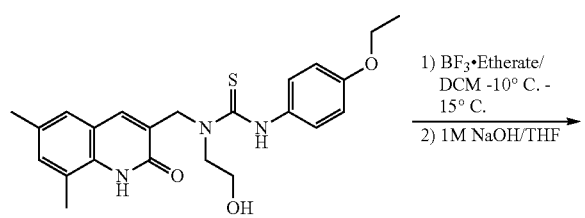

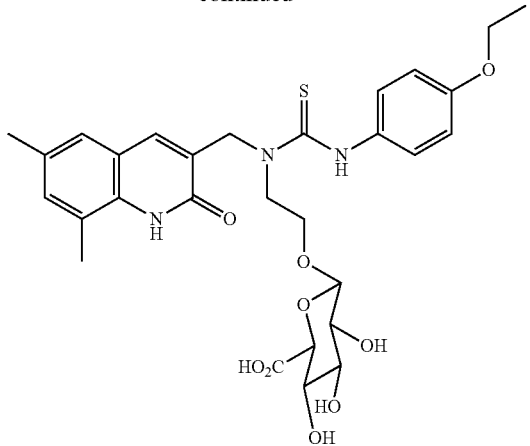

Inh-1 in dichloromethane was cooled to −10 degrees and was treated with 2,3,4-Tri-O-acetyl-1-O-trichloroacetimidoyl-α-D-glucopyranuronic acid methyl ester followed by borontrifluoride e the rate solution. After stirring for 30 minutes the reaction was warmed to room temperature, stirred for 3 hours and then quenched with saturated NaHCO₃. After separation of the organics layer and drying, the crude reaction was taken to the next step. Hydrolysis of the acetate's and methyl ester with 1N NaOH afforded the desired Inh-1 glucuronide. LCMS (ESI) 602 (M+H).

Alternative Glucuronide Synthesis:

To generate inhibitor-glucuronides using non-chemical synthesis, biosynthetic techniques are utilized, using Corning® Supersomes™ UGT. UGT supersomes are baculovirus generated UGTs, and far more pure than normal microsomal fractions. Briefly, supersome activation requires alamethicin (pore forming molecule), UGT supersomes, BSA, microsome buffer (100 mM Tris ph 7.5, 100 mM NaCl) and $MgCl_2$. This mixture was incubated on ice for 30 minutes to allow for pore formation followed by addition of the acceptor parent drug substrate, incubated for an additional 5 minutes at 37° C. Addition of the UGT cofactor UDP-glucuronic acid (UDP-GA) initiates the reaction, incubated at 37° C., for an overnight incubation.

Since it was unclear which specific UGT form conjugates with the inhibitors, a master mix of all available UGTs was created (14 in total from both the UGT1 and UGT2 line) to use in the UGT reactions.

A UDP-Glo™ assay kit from Promega was used to quantitate the amount of inhibitor glucuronide production. A luciferase reaction detects the formation of UDP molecules, which is generated during the UGT reaction converting UDP-GA to UDP, in a one-to-one molar ratio as production of inhibitor-glucuronide.

Example 1

2,6-dimethyl-3-nitro-benzoic acid

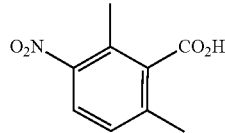

To the acid (10 g, 66.6 mmole) in nitromethane (100 mL) cooled to 0° C. is added conc sulfuric acid (67 mL) after stirring for 10 minutes, conc nitric acid (42 mL) is then added dropwise over 1 hr. The reaction mixture is stirred for 6 hrs. After addition of ice water (300 mL) ethyl acetate was added and the two layers separated. The organic layer was then dried with magnesium sulfate and then concentrated under vacuum to afford the desired product.

The crude product was taken to the next step.

Example 2

(2,6-dimethyl-3-nitro-phenyl)methanol

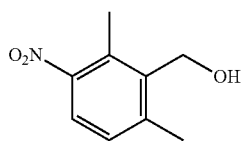

To the nitro acid (2.7 g, 13.8 mmole) in THF (15 mL) cooled to 0° C. is added a 2.0 M solution of Borane/THF complex (14.0 mL). The contents were then stirred at room temperature for 4 hrs. The reaction mixture is then quenched with methanol. Ethyl acetate was then added followed by sat'd $NaHCO_3$. The organic layer was then dried over magnesium sulfate and then concentrated under vacuum to afford the desired product.

Example 3

(3-amino-2,6-dimethyl-phenyl)methanol

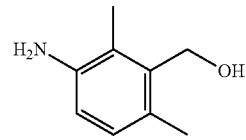

To a solution of the nitro alcohol (20 g, 110 mmole) in methanol (200 mL) is added 10% Pd/C (2 g). The contents were then pressured under hydrogen at 80 psi for 16 hrs. After filtration over celite and concentration under vacuum the crude product was taken to the next step.

Example 4

N-[3-(hydroxymethyl)-2,4-dimethyl-phenyl]acetamide

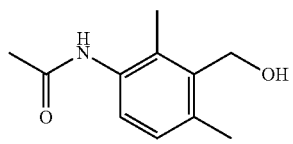

To the amino compound (7 g, 46.4 mmole) in acetonitrile (200 mL) cooled to 0° C. is added acetic anhydride (5.2 mL, 1.1 eq). The contents were then warmed to room temperature and then stirred for 20 hrs. The reaction is mixture is then concentrated under vacuum to afford the N-acetylated compound as an off-white solid.

Example 5

7-(chloromethyl)-6,8-dimethyl-2-oxo-1H-quinoline-3-carbaldehyde

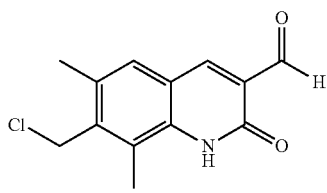 [SMILES: Cc1cc2cc(C=O)c(=O)[nH]c2c(C)c1CCl]

To DMF (0.478 mL, 6.19 mmole) was added phosphorous oxy chloride (1.06 mL, 11.41 mmole) followed by the addition of N-[3-(hydroxymethyl)-2,4-dimethyl-phenyl]acetamide (0.314 g, 1.63 mmole). The contents were refluxed for 4 hrs. After cooling, dichloromethane was added followed by satd $NaHCO_3$. The organic layer was separated, dried over magnesium sulfate and concentrated under vacuum. The crude product was columned using DCM/methanol (0-10%) to afford the desired product.

Example 6

[3-[(2-hydroxyethylamino)methyl]-6,8-dimethyl-2-oxo-1H-quinolin-7-yl]methyl acetate

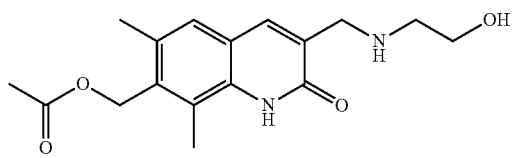 [SMILES: CC(=O)OCc1c(C)cc2cc(CNCCO)c(=O)[nH]c2c1C]

To a solution of 7-(chloromethyl)-6,8-dimethyl-2-oxo-1H-quinoline-3-carbaldehyde (0.1 g, 40.2 mmole) in DCE (3 mL) is added acetic acid (0.032 mL) followed by the addition of 2-aminoethanol (0.032 g, 1.3 eq) and sodium triacetoxyborohydride (0.255 g, 3 eq). The contents were stirred overnight, concentrated and then columned directly to afford the desired compound. LCMS ESI: 295.1 (M+H)

Example 7

[3-[[(4-ethoxyphenyl)carbamothioyl-(2-hydroxyethyl)amino]methyl]-6,8-dimethyl-2-oxo-1H-quinolin-7-yl]methyl acetate (1)

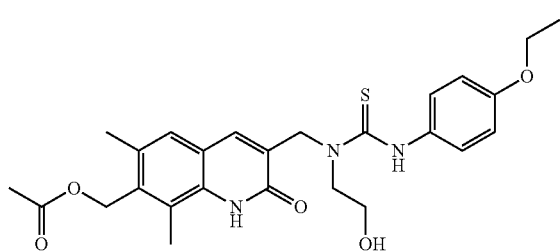 [SMILES: CCOc1ccc(NC(=S)N(CCO)Cc2cc3cc(C)c(COC(C)=O)c(C)c3[nH]c2=O)cc1]

To a solution of [3-[(2-hydroxyethylamino)methyl]-6,8-dimethyl-2-oxo-1H-quinolin-7-yl]methyl acetate (0.103 mmole) in DCE (2 mL) is added 1-ethoxy-4-isothiocyanatobenzene (0.103 mmole) and the contents heated overnight at 80° C. After cooling, the crude product is purified over silica gel using Ethyl acetate/hexane (0-100%) to afford the desired product. LCMS ESI: 482.6 (M+H).

Example 8

6,8-dimethyl-7-[(4-methylpiperazin-1-yl)methyl]-2-oxo-1H-quinoline-3-carbaldehyde (I)

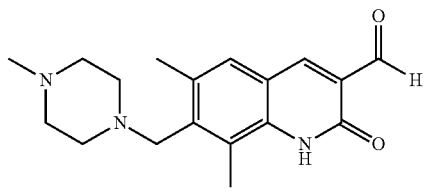 [SMILES: Cc1cc2cc(C=O)c(=O)[nH]c2c(C)c1CN1CCN(C)CC1]

To a solution of 7-(chloromethyl)-6,8-dimethyl-2-oxo-1H-quinoline-3-carbaldehyde (0.2 g, 0.80 mmole) in AcCN (6 mL) is added N-methylpiperazine (0.27 mL, 3 eq). The contents are refluxed for 16 hrs. After concentration under vacuum, the crude product is columned over silica gel using DCM/MeOH (0-10%) to afford the product as a yellow solid. LCMS ESI: 314 (M+H).

Example 9

3-[(2-hydroxyethylamino)methyl]-6,8-dimethyl-7-[(4-methylpiperazin-1-yl)methyl]-1H-quinolin-2-one (II)

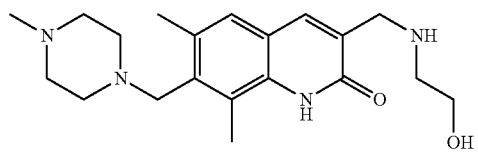 [SMILES: Cc1cc2cc(CNCCO)c(=O)[nH]c2c(C)c1CN1CCN(C)CC1]

To 6,8-dimethyl-7-[(4-methylpiperazin-1-yl)methyl]-2-oxo-1H-quinoline-3-carbaldehyde (0.135 g, 43.1 mmole) in DCE is added acetic acid (0.026 mL) followed by the addition of 2-aminoethanol (0.04 mL, 1.5 eq) and sodium triacetoxyborohydride (0.365 g, 4 eq). The contents are stirred for 12 hrs, after addition of satd NaHCO$_3$, the contents are stirred for 30 min, ethyl acetate is then added and the layers separated. The organic layer is dried with magnesium sulfate, concentrated under vacuum and then columned over silica gel using DCM/MeOH (0-20%) to afford the desired product. LCMS ESI: 359.6 (M+H).

Example 10

1-[[6,8-dimethyl-7-[(4-methylpiperazin-1-yl)methyl]-2-oxo-1H-quinolin-3-yl]methyl]-3-(4-ethoxyphenyl)-1-(2-hydroxyethyl)thiourea (2)

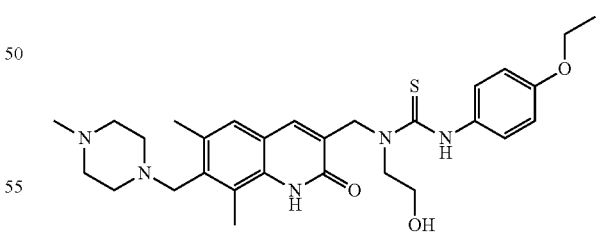

To a solution of 3-[(2-hydroxyethylamino)methyl]-6,8-dimethyl-7-[(4-methylpiperazin-1-yl)methyl]-1H-quinolin-2-one (0.0619 mmole) is added 1-ethoxy-4-isothiocyanatobenzene (0.0681 mmole) and the contents heated overnight at 80° C. After cooling, the crude product is purified over silica gel using Ethyl acetate/hexane (0-100%) to afford the desired product. LCMS ESI: 538.4 (M+H).

Example 11

1-[[6,8-dimethyl-7-[(4-methylpiperazin-1-yl)methyl]-2-oxo-1H-quinolin-3-yl]methyl]-3-(4-ethoxyphenyl)-1-(2-hydroxyethyl)urea (3)

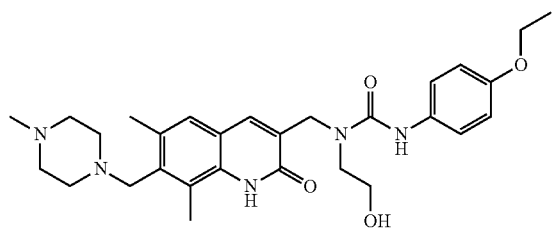 [SMILES: CCOc1ccc(NC(=O)N(CCO)Cc2cc3cc(C)c(CN4CCN(C)CC4)c(C)c3[nH]c2=O)cc1]

To a solution of 3-[(2-hydroxyethylamino)methyl]-6,8-dimethyl-7-[(4-methylpiperazin-1-yl)methyl]-1H-quinolin-2-one (0.0619 mmole) is added 1-ethoxy-4-isocyanato-benzene (0.0681 mmole) and the contents stirred overnight at room temperature. After concentration, the crude reaction mixture is purified over silica gel using Ethyl acetate/hexane (0-100%) to afford the desired product. LCMS ESI 522.6 (M+H).

Example 12

7-(diethylaminomethyl)-6,8-dimethyl-2-oxo-1H-quinoline-3-carbaldehyde (III)

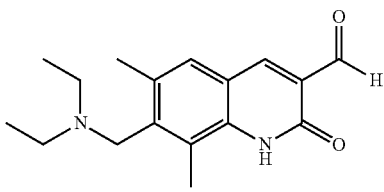 [SMILES: CCN(CC)Cc1c(C)cc2cc(C=O)c(=O)[nH]c2c1C]

To a solution of 7-(chloromethyl)-6,8-dimethyl-2-oxo-1H-quinoline-3-carbaldehyde (0.25 g, 1.0 mmole) in AcCN (6 mL) is added N,N-diethylamine (0.22 g, 3 eq). The contents are refluxed for 16 hrs. After concentration under vacuum, the crude product is columned over silica gel using DCM/MeOH (0-10%) to afford the product as a yellow solid. LCMS ESI: 287 (M+H).

Example 13

7-(diethylaminomethyl)-3-[(2-hydroxyethylamino)methyl]-6,8-dimethyl-1H-quinolin-2-one (IV)

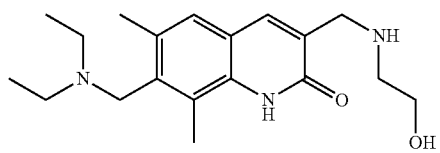 [SMILES: CCN(CC)Cc1c(C)cc2cc(CNCCO)c(=O)[nH]c2c1C]

To 7-(diethylaminomethyl)-6,8-dimethyl-2-oxo-1H-quinoline-3-carbaldehyde (0.15 g, 0.52 mmole) in DCE is added acetic acid (0.090 mL) followed by the addition of 2-aminoethanol (0.064 mL) and sodium triacetoxyborohydride (0.44 g, 4 eq). The contents are stirred for 12 hrs, after addition of satd NaHCO3, the contents are stirred for 30 min, ethyl acetate is then added and the layers separated. The organic layer is dried with magnesium sulfate, concentrated under vacuum and then columned over silica gel using DCM/MeOH (0-15%) to afford the desired product. LCMS ESI: 322.6 (M+H).

Example 14

1-[[7-(diethylaminomethyl)-6,8-dimethyl-2-oxo-1H-quinolin-3-yl]methyl]-3-(4-ethoxyphenyl)-1-(2-hydroxyethyl)thiourea (4)

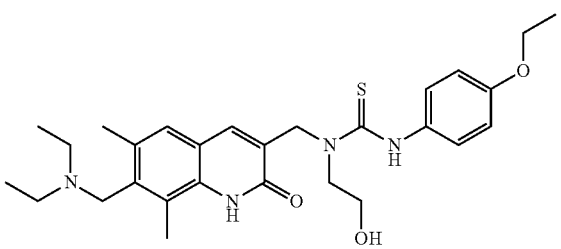 [SMILES: CCOc1ccc(NC(=O)N(CCO)Cc2cc3cc(C)c(CN(CC)CC)c(C)c3[nH]c2=O)cc1]

To a solution of 7-(diethylaminomethyl)-3-[(2-hydroxyethylamino)methyl]-6,8-dimethyl-1H-quinolin-2-one (0.075 mmole) is added 1-ethoxy-4-isothiocyanato-benzene (0.075 mmole) and the contents heated overnight at 80° C. After cooling, the crude product is purified over silica gel using Ethyl acetate/hexane (0-100%) to afford the desired product. LCMS ESI: 511.4 (M+H).

Example 15

1-[[7-(diethylaminomethyl)-6,8-dimethyl-2-oxo-1H-quinolin-3-yl]methyl]-3-(4-ethoxyphenyl)-1-(2-hydroxyethyl)urea (5)

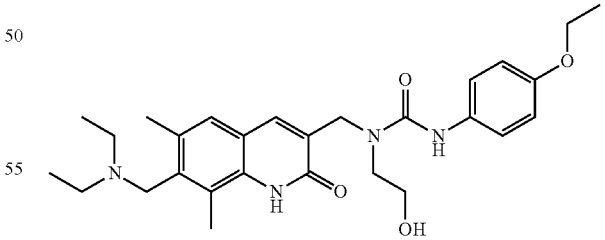

To a solution of 7-(diethylaminomethyl)-3-[(2-hydroxyethylamino)methyl]-6,8-dimethyl-1H-quinolin-2-one (0.075 mmole) is added 1-ethoxy-4-isocyanato-benzene (0.075 mmole) and the contents stirred at room temperature for 15 hrs. After concentration, the crude product is purified over silica gel using Ethyl acetate/hexane (0-100%) to afford the desired product. LCMS ESI: 495.6 (M+H).

Example 16 tert-butyl 3-[[7-(diethylaminomethyl)-6,8-dimethyl-oxo-1H-quinolin-3-yl]methylamino]pyrrolidine-1-carboxylate (V)

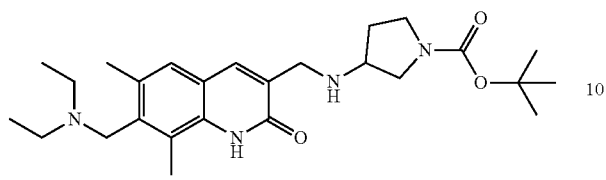

Intermediate (V) was synthesized using procedure similar to that for intermediate (IV) by treating intermediate (III) (0.349 mmole) with tert-butyl 3-aminopyrrolidine-1-carboxylate (0.095 g, 1.5 eq) to afford the desired product. LCMS ESI: 457.4 (M+H).

Example 17 tert-butyl 3-[[7-(diethylaminomethyl)-6,8-dimethyl-2-oxo-1H-quinolin-3-yl]methyl-[(4-ethoxyphenyl)carbamothioyl]amino]pyrrolidine-1-carboxylate (VI)

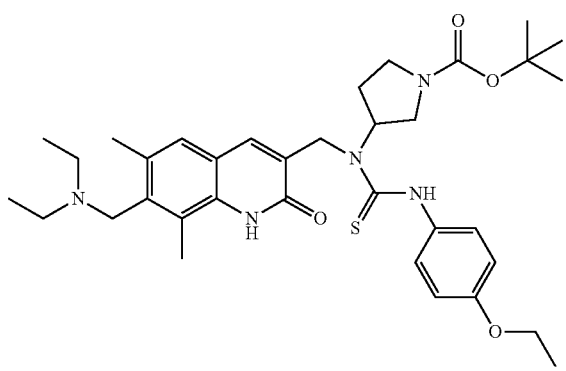 [SMILES: CCOc1ccc(NC(=S)N(Cc2cc3cc(C)c(CN(CC)CC)c(C)c3[nH]c2=O)C2CCN(C(=O)OC(C)(C)C)C2)cc1]

Intermediate (VI) is synthesized using a similar procedure to that in compound 2, by treating intermediate (V) (0.055 mmole) with 1-ethoxy-4-isothiocyanato-benzene (0.061 mmole) to afford the desired product LCMS ESI: 636.4 (M+H).

Example 20 tert-butyl-3-[[7-(diethylaminomethyl)-6,8-dimethyl-2-oxo-1H-quinolin-3-yl]methyl-[(4-ethoxyphenyl)carbamoyl]amino]pyrrolidine-1-carboxylate (VII)

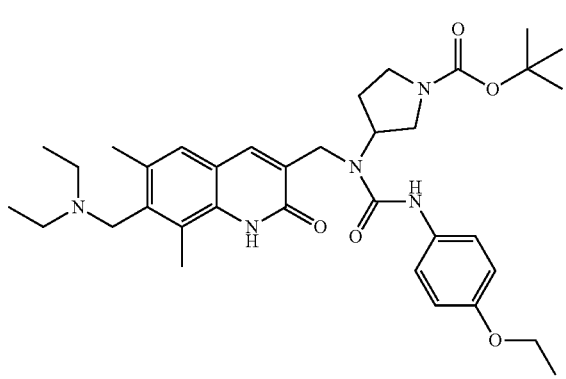 [SMILES: CCOc1ccc(NC(=O)N(Cc2cc3cc(C)c(CN(CC)CC)c(C)c3[nH]c2=O)C2CCN(C(=O)OC(C)(C)C)C2)cc1]

Intermediate (VII) is synthesized using a similar procedure to that in compound 2, by treating intermediate (V) (0.055 mmole) with 1-ethoxy-4-isothiocyanato-benzene (0.061 mmole) to afford the desired product LCMS ESI: 620.6 (M+H).

Example 21

1-[[7-(diethylaminomethyl)-6,8-dimethyl-2-oxo-1H-quinolin-3-yl]methyl]-3-(4-ethoxyphenyl)-1-pyrrolidin-3-yl-thiourea HCl salt (6)

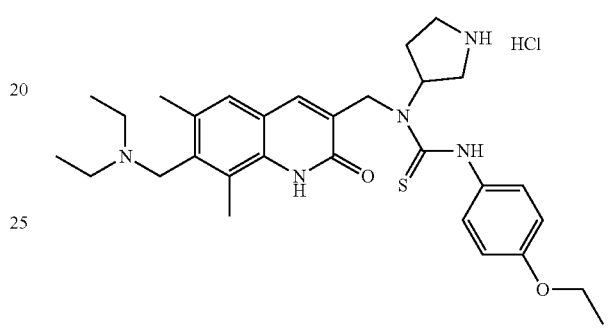

To intermediate (VI) (9 mg) in DCM (1 mL) is added 4N HCl/Dioxane (0.108 mL) at room temperature, after stirring for 2 hrs, the contents were concentrated under vacuum to afford the HCl salt of compound 6. LCMS ESI: 536.6 (M+H).

Example 22

1-[[7-(diethylaminomethyl)-6,8-dimethyl-2-oxo-1H-quinolin-3-yl]methyl]-3-(4-ethoxyphenyl)-1-pyrrolidin-3-yl-urea (7)

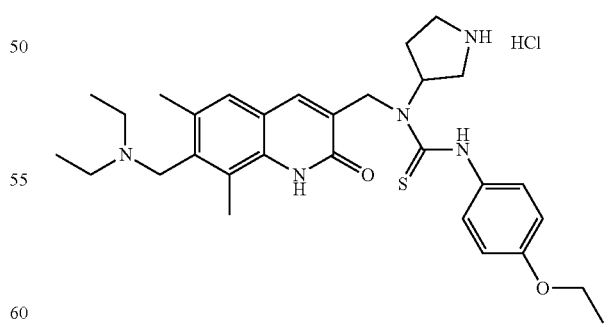

To intermediate (VII) (9 mg) in DCM (1 mL) is added 4N HCl/Dioxane (0.108 mL) at room temperature, after stirring for 2 hrs, the contents were concentrated under vacuum to afford the HCl salt of compound 7. LCMS ESI: 520.7 (M+H).

Example 23 tert-butyl 3-[[7-(diethylaminomethyl)-6,8-dimethyl-2-oxo-1H-quinolin-3-yl]methylamino]azetidine-1-carboxylate (VIII)

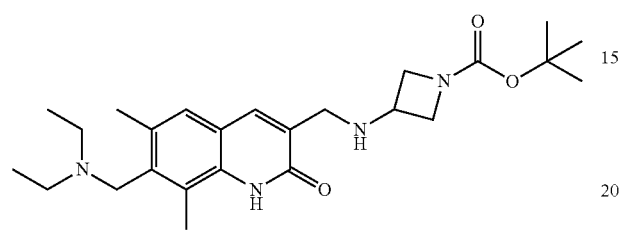

Intermediate (VIII) is synthesized using a similar experimental procedure as for intermediate (IV) by treating intermediate (III) (0.349 mmole) with tert-butyl 3-aminoazetidine-1-carboxylate (0.090 g, 1.5 eq) to afford the desired product. LCMS ESI: 443.5 (M+H).

Example 24 tert-butyl 3-[[7-(diethylaminomethyl)-6,8-dimethyl-2-oxo-1H-quinolin-3-yl]methyl-[(4-ethoxyphenyl)carbamothioyl]amino]azetidine-1-carboxylate (IX)

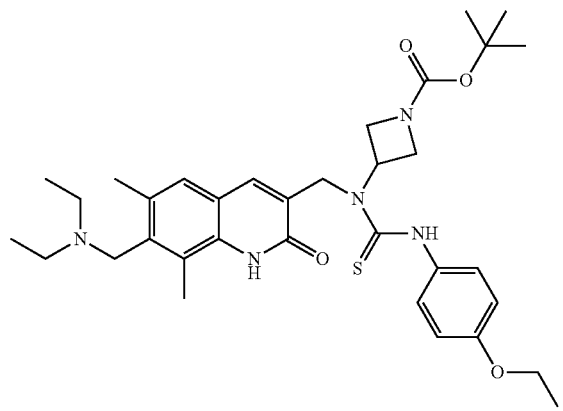 [SMILES: CCOc1ccc(NC(=S)N(Cc2cc3cc(C)c(CN(CC)CC)c(C)c3[nH]c2=O)C2CN(C(=O)OC(C)(C)C)C2)cc1]

Intermediate (IX) is synthesized using a similar procedure to that in compound 2, by treating intermediate (VIII) (0.056 mmole) with 1-ethoxy-4-isothiocyanato-benzene (0.062 mmole) to afford the desired product. LCMS ESI: 521.5 (-tertbutoxycarbonyl).

Example 25 tert-butyl 3-[[7-(diethylaminomethyl)-6,8-dimethyl-2-oxo-1H-quinolin-3-yl]methyl-[(4-ethoxyphenyl)carbamoyl]amino]azetidine-1-carboxylate (X)

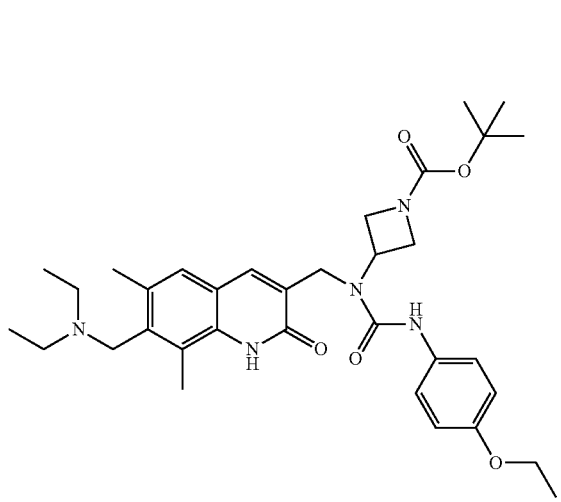 [SMILES: CCOc1ccc(NC(=O)N(Cc2cc3cc(C)c(CN(CC)CC)c(C)c3[nH]c2=O)C2CN(C(=O)OC(C)(C)C)C2)cc1]

Intermediate (XI) is synthesized using a similar procedure to that in compound 2, by treating intermediate (VIII) (0.056 mmole) with 1-ethoxy-4-isocyanato-benzene (0.062 mmole) to afford the desired product.

Example 26

1-(azetidin-3-yl)-1-[[7-(diethylaminomethyl)-6,8-dimethyl-2-oxo-1H-quinolin-3-yl]methyl]-3-(4-ethoxyphenyl)thiourea HCl salt (8)

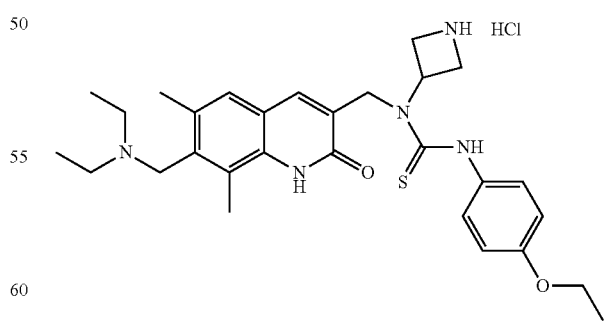

Compound 8 is synthesized using a similar experimental procedure as for compound 7 using 4N HCl/Dioxane. LCMS ESI 522.6 (M+H).

Example 27

1-(azetidin-3-yl)-1-[[7-(diethylaminomethyl)-6,8-dimethyl-2-oxo-1H-quinolin-3-yl]methyl]-3-(4-ethoxyphenyl)urea (9)

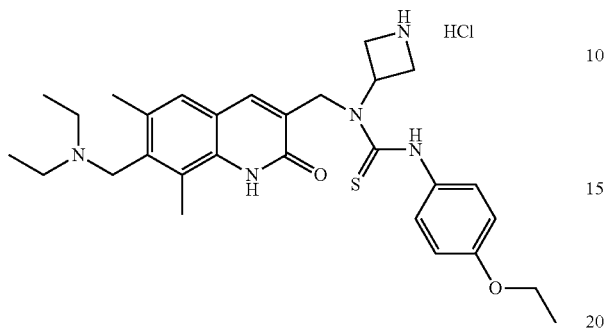

Compound 9 is synthesized using a similar experimental procedure as for compound 7 using 4N HCl/Dioxane. LCMS ESI: 506.8 (M+H).

Example 28

7-(diethylaminomethyl)-3-[[(3-hydroxycyclobutyl)amino]methyl]-6,8-dimethyl-1H-quinolin-2-one (XII)

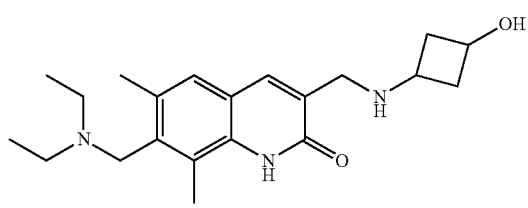 [SMILES: CCN(CC)Cc1c(C)cc2cc(CNC3CC(O)C3)c(=O)[nH]c2c1C]

Intermediate (XII) is synthesized using procedure similar to that for intermediate (IV) by treating intermediate (III) (0.349 mmole) with azetidin-3-ol (0.086 g, 2 eq) to afford the desired product. LCMS ESI: 358.6 (M+H).

Example 29

1-[[7-(diethylaminomethyl)-6,8-dimethyl-2-oxo-1H-quinolin-3-yl]methyl]-3-(4-ethoxyphenyl)-1-(3-hydroxycyclobutyl)thiourea (10)

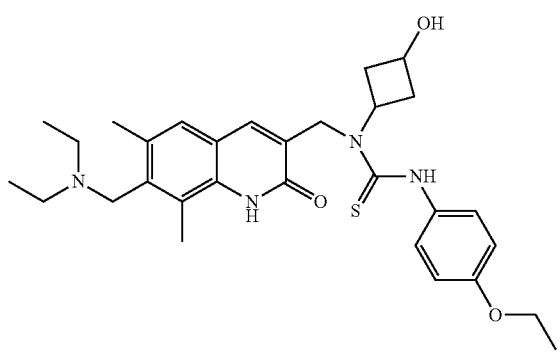 [SMILES: CCOc1ccc(NC(=S)N(Cc2cc3cc(C)c(CN(CC)CC)c(C)c3[nH]c2=O)C2CC(O)C2)cc1]

Compound 10, is synthesized using a similar procedure to that in compound 2, by treating intermediate (XII) (0.070 mmole) with 1-ethoxy-4-isocyanato-benzene (0.070 mmole) to afford the desired product P162. LCMS ESI: 537.8 (M+H).

Example 30

1-[[7-(diethylaminomethyl)-6,8-dimethyl-2-oxo-1H-quinolin-3-yl]methyl]-3-(4-ethoxyphenyl)-1-(3-hydroxycyclobutyl)urea (11)

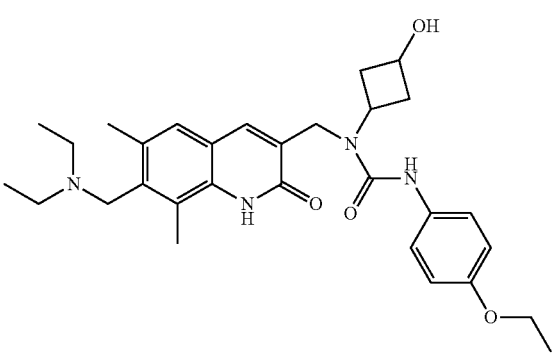 [SMILES: CCOc1ccc(NC(=O)N(Cc2cc3cc(C)c(CN(CC)CC)c(C)c3[nH]c2=O)C2CC(O)C2)cc1]

Compound 11, is synthesized using a similar procedure to that in compound 2, by treating intermediate (XII) (0.070 mmole) with 1-ethoxy-4-isocyanato-benzene (0.070 mmole) to afford the desired product P161. LCMS ESI: 521.7

Example 31

6,8-dimethyl-7-(morpholinomethyl)-2-oxo-1H-quinoline-3-carbaldehyde (XIII)

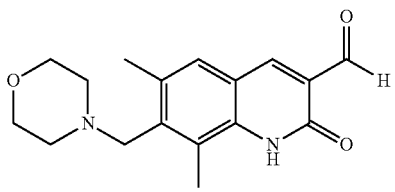 [SMILES: Cc1cc2cc(C=O)c(=O)[nH]c2c(C)c1CN1CCOCC1]

To a solution of 6,8-dimethyl-7-(morpholinomethyl)-2-oxo-1H-quinoline-3-carbaldehyde (0.25 g, 1.0 mmole) in AcCN (6 mL) is added N-methylmorpholine (0.261 mL, 3 eq). The contents are refluxed for 16 hrs. After concentration under vacuum, the crude product is columned over silica gel using DCM/MeOH (0-10%) to afford the product as a yellow solid. LCMS ESI: 301.4 (M+H).

Example 32

3-[(2-hydroxyethylamino)methyl]-6,8-dimethyl-7-(morpholinomethyl)-1H-quinolin-2-one (XIV)

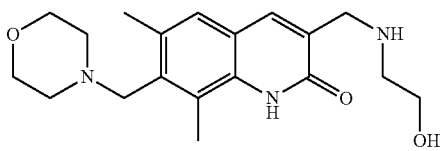 [SMILES: Cc1cc2cc(CNCCO)c(=O)[nH]c2c(C)c1CN1CCOCC1]

To 6,8-dimethyl-7-(morpholinomethyl)-2-oxo-1H-quinoline-3-carbaldehyde (0.125 g, 0.42 mmole) in DCE is added acetic acid (0.090 mL) followed by the addition of 2-aminoethanol (0.381 mL, 1.5 eq) and sodium triacetoxyborohydride (0.36 g, 4 eq). The contents are stirred for 12 hrs, after addition of satd NaHCO3, the contents are stirred for 30 min, ethyl acetate is then added and the layers separated. The organic layer is dried with magnesium sulfate, concentrated under vacuum and then columned over silica gel using DCM/MeOH (0-15%) to afford the desired product. LCMS ESI: 346.2 (M+H).

Example 33

1-[[6,8-dimethyl-7-(morpholinomethyl)-2-oxo-1H-quinolin-3-yl]methyl]-3-(4-ethoxyphenyl)-1-(2-hydroxyethyl)urea (12)

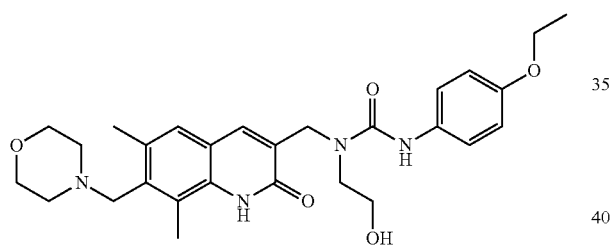

To a solution of 3-[(2-hydroxyethylamino)methyl]-6,8-dimethyl-7-(morpholinomethyl)-1H-quinolin-2-one (0.075 mmole) is added 1-ethoxy-4-isocyanato-benzene (0.075 mmole) and the contents stirred at room temperature for 15 hrs. After concentration, the crude product is purified over silica gel using Ethyl acetate/hexane (0-100%) to afford the desired product. LCMS ESI: 509.5 (M+H).

Example 34

1-[[6,8-dimethyl-7-(morpholinomethyl)-2-oxo-1H-quinolin-3-yl]methyl]-3-(4-ethoxyphenyl)-1-(2-hydroxyethyl)thiourea (13)

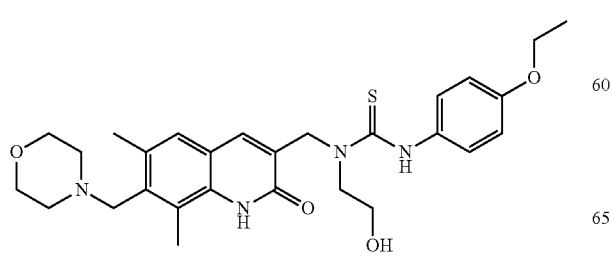

To a solution of 3-[(2-hydroxyethylamino)methyl]-6,8-dimethyl-7-(morpholinomethyl)-1H-quinolin-2-one (0.075 mmole) is added 1-ethoxy-4-isothiocyanato-benzene (0.075 mmole) using similar conditions to that in compound 2. After concentration, the crude product is purified over silica gel using Ethyl acetate/hexane (0-100%) to afford the desired product. LCMS ESI: 525.4 (M+H).

Using similar procedures, the following compounds were made:

Example 35

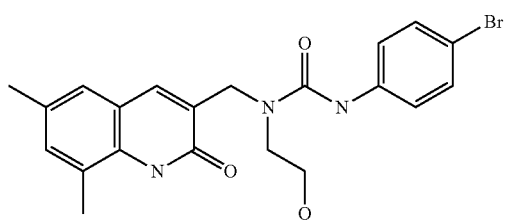 [SMILES: Cc1cc(C)c2[nH]c(=O)c(CN(CCO)C(=O)Nc3ccc(Br)cc3)cc2c1]

1H NMR (500 MHz, DMSO-$d_6$) δ ppm 2.31 (s, 3H) 2.42 (s, 3H) 3.41 (t, J=5.62 Hz, 2H) 3.60 (q, J=5.54 Hz, 2H) 4.46 (s, 2H) 5.00 (br. s., 1H) 7.21 (s, 1H) 7.35 (s, 1H) 7.42 (s, 4H) 7.82 (s, 1H) 11.28 (br. s., 1H). [M+1]$^+$=444/446.

Example 36

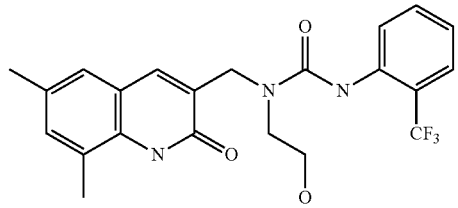 [SMILES: Cc1cc(C)c2[nH]c(=O)c(CN(CCO)C(=O)Nc3ccccc3C(F)(F)F)cc2c1]

1H NMR (500 MHz, DMSO-$d_6$) δ ppm 2.31 (s, 3H) 2.40 (s, 3H) 3.54 (t, J=7.83 Hz, 2H) 3.70 (t, J=7.83 Hz, 2H) 4.25 (s, 2H) 7.17 (s, 1H) 7.28 (s, 1H) 7.51-7.60 (m, 2H) 7.66 (s, 1H) 7.71-7.83 (m, 2H) 11.00 (s, 1H). LCMS ESI (M+H): 416 ((M−H2O)+1)

Example 37

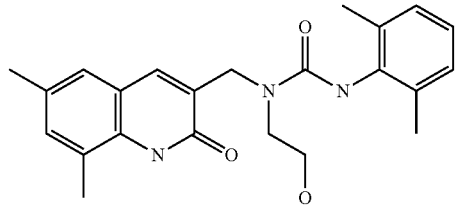 [SMILES: Cc1cc(C)c2[nH]c(=O)c(CN(CCO)C(=O)Nc3c(C)cccc3C)cc2c1]

LCMS ESI (M+H): 394

Example 38

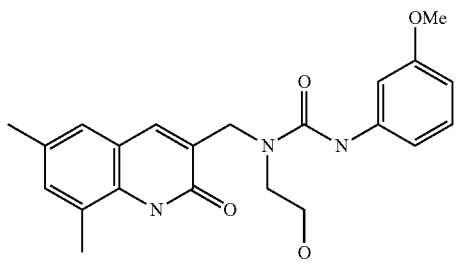 [SMILES: COc1cccc(NC(=O)N(CCO)Cc2cc3cc(C)cc(C)c3[nH]c2=O)c1]

1H NMR (500 MHz, CHLOROFORM-d) δ ppm 2.40 (s, 3H) 2.43 (s, 3H) 3.43-3.53 (m, 2H) 3.79 (s, 3H) 3.89 (d, J=4.40 Hz, 2H) 4.46 (s, 2H) 6.55 (dd, J=8.31, 2.45 Hz, 1H) 6.96-7.02 (m, 1H) 7.16 (t, J=8.07 Hz, 1H) 7.19-7.23 (m, 1H) 7.24 (s, 1H) 7.25-7.30 (m, 1H) 7.75 (s, 1H) 8.95 (br. s., 1H) 10.07 (br. s., 1H). LCMS ESI (M+H): 396

Example 39

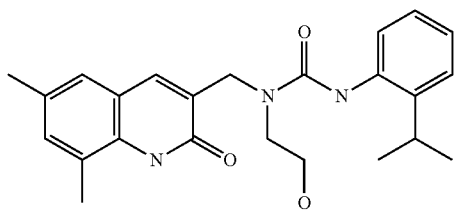 [SMILES: Cc1cc(C)c2[nH]c(=O)c(CN(CCO)C(=O)Nc3ccccc3C(C)C)cc2c1]

1H NMR (500 MHz, CHLOROFORM-d) δ ppm 1.23 (d, J=6.85 Hz, 6H) 2.39 (s, 3H) 2.43 (s, 3H) 3.15-3.30 (m, 1H) 3.44-3.57 (m, 2H) 3.88 (d, J=4.40 Hz, 2H) 4.30 (br. s., 1H) 4.51 (s, 2H) 7.06-7.18 (m, 2H) 7.19-7.32 (m, 3H) 7.44 (d, J=7.83 Hz, 1H) 7.75 (s, 1H) 8.85 (br. s., 1H) 8.89-9.01 (m, 1H). LCMS ESI (M+H): 408

Example 40

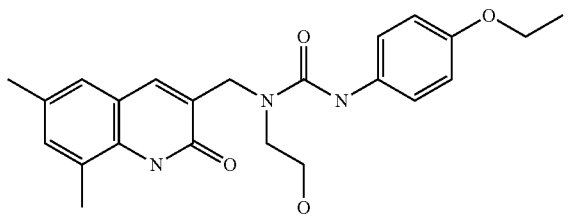 [SMILES: CCOc1ccc(NC(=O)N(CCO)Cc2cc3cc(C)cc(C)c3[nH]c2=O)cc1]

1H NMR (500 MHz, CHLOROFORM-d) δ ppm 1.38 (t, J=6.85 Hz, 3H) 2.40 (s, 3H) 2.43 (s, 3H) 3.42-3.54 (m, 2H) 3.89 (q, J=4.73 Hz, 2H) 3.99 (q, J=6.85 Hz, 2H) 4.38-4.49 (m, 3H) 6.82 (d, J=8.80 Hz, 2H) 7.19-7.30 (m, 2H) 7.35 (d, J=8.80 Hz, 2H) 7.74 (s, 1H) 8.94 (br. s., 1H) 9.83 (d, J=96 Hz, 1H). LCMS ESI (M+H): 410

Example 41

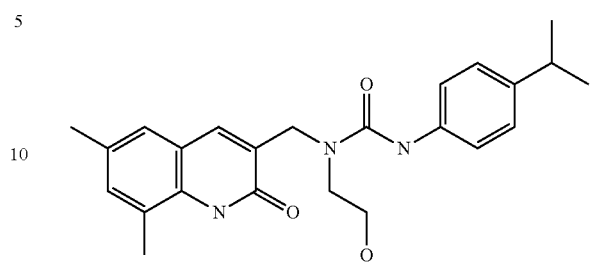

1H NMR (500 MHz, DMSO-d$_6$) δ ppm 1.14 (d, J=6.85 Hz, 6H) 2.28 (s, 3H) 2.39 (s, 3H) 2.71-2.83 (m, 1H) 3.32-3.42 (m, 2H) 3.50-3.62 (m, 2H) 4.42 (br. s., 2H) 4.96 (d, J=3.42 Hz, 1H) 7.07 (d, J=8.31 Hz, 2H) 7.17 (br. s., 1H) 7.29 (d, J=8.31 Hz, 3H) 7.75 (br. s., 1H) 9.37 (br. s., 1H) 11.21 (br. s., 1H). LCMS ESI (M+H): 408

Example 42

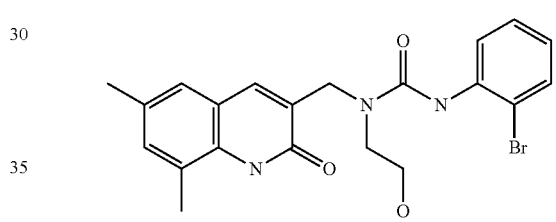

1H NMR (500 MHz, DMSO-d$_6$) δ ppm 2.27 (s, 3H) 2.39 (s, 3H) 3.41-3.50 (m, 2H) 3.57-3.66 (m, 2H) 4.43 (s, 2H) 6.86-6.99 (m, 1H) 7.16 (s, 1H) 7.22-7.38 (m, 2H) 7.56 (d, J=7.83 Hz, 1H) 7.68-7.84 (m, 2H) 8.89 (br. s., 1H) 10.95-11.19 (m, 1H). LCMS ESI (M+H): 443/445

Example 43

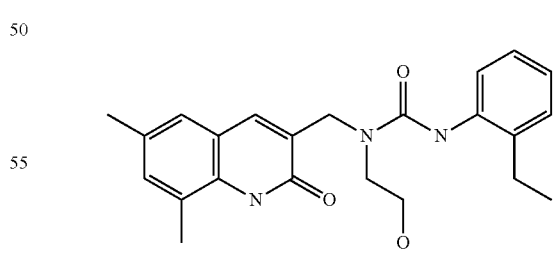

1H NMR (500 MHz, DMSO-d$_6$) δ ppm 1.13 (t, J=7.58 Hz, 3H) 2.27 (s, 3H) 2.37 (s, 3H) 2.62-2.75 (m, 2H) 3.40 (m, 2H) 3.56 (t, J=5.87 Hz, 2H) 4.38 (s, 2H) 6.91-7.00 (m, 2H) 7.06 (d, J=9.29 Hz, 2H) 7.14 (d, J=6.36 Hz, 2H) 7.41 (d, J=7.83 Hz, 1H) 7.53-7.64 (m, 1H) 8.51 (s, 1H). LCMS ESI (M+H): 394

Example 44

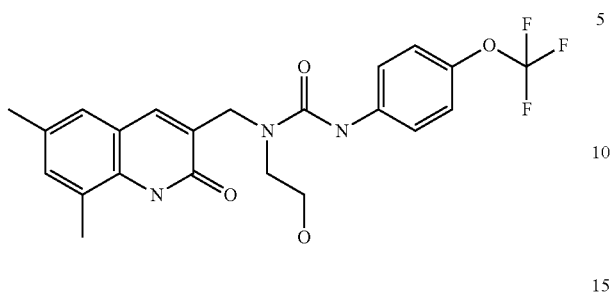

1H NMR (500 MHz, DMSO-d$_6$) δ ppm 2.28 (s, 3H) 2.40 (s, 3H) 3.36-3.44 (m, 2H) 3.54-3.63 (m, 2H) 4.43-4.48 (m, 2H) 7.16-7.21 (m, 1H) 7.21-7.26 (m, 2H) 7.31-7.35 (m, 1H) 7.47-7.54 (m, 2H) 7.73-7.82 (m, 1H)) 11.25 (br. s., 1H). LCMS ESI (M+H): 450

Example 45

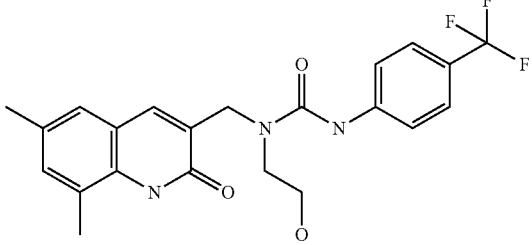

Example 46

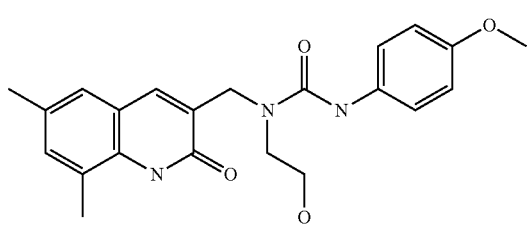

1H NMR (500 MHz, CHLOROFORM-d) δ ppm 2.39 (s, 3H) 2.43 (s, 3H) 3.43-3.53 (m, 2H) 3.77 (s, 3H) 3.88 (d, J=3.91 Hz, 2H) 4.39-4.50 (m, 2H) 6.76-6.87 (m, 2H) 7.19-7.29 (m, 2H) 7.34 (d, J=8.80 Hz, 2H) 7.76 (s, 1H) 9.17 (br. s., 1H) 9.80 (br. s., 1H). LCMS ESI (M+H): 396

Example 47

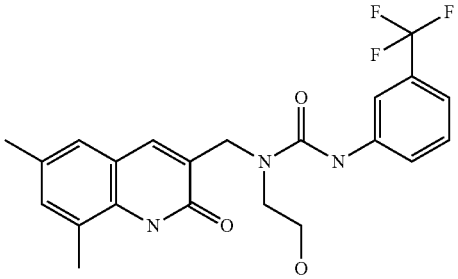 [SMILES: Cc1cc(C)c2[nH]c(=O)c(CN(CCO)C(=O)Nc3cccc(C(F)(F)F)c3)cc2c1]

1H NMR (500 MHz, CHLOROFORM-d) δ ppm 2.41 (s, 3H) 2.47 (s, 3H) 3.49 (br. s., 2H) 3.92 (br. s., 2H) 4.49 (s, 2H) 7.22-7.34 (m, 3H) 7.35-7.43 (m, 1H) 7.66 (br. s., 1H) 7.77 (br. s., 1H) 7.80-7.87 (m, 1H). LCMS ESI (M+H): 434

Example 48

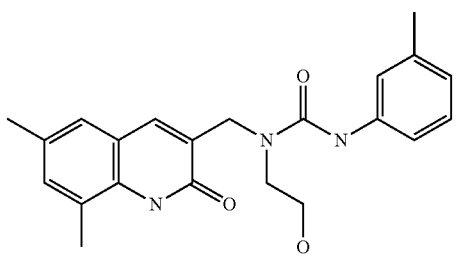 [SMILES: Cc1cccc(NC(=O)N(CCO)Cc2cc3cc(C)cc(C)c3[nH]c2=O)c1]

LCMS ESI (M+H): 380

In addition, the present invention includes certain N-BOC-glycinol esters as synthetic intermediates, which may be synthesized using the following general procedure: N-BOCglycinol (10 mmol) was taken in CH$_2$C$_2$ (70 mL) at room temperature under nitrogen. Hunig's base (2.1 ml, 1.2 eq.) was added and after 5 minutes acid chloride was added. The resulting reaction mixture was stirred at room temperature overnight. At this time TLC (2:1, hexanes/EA) showed mainly non-polar spots and minor amount of starting glycinol. Hence the reaction mixture was worked up in CH$_2$Cl$_2$—H$_2$O. The aqueous layer was extracted with CH$_2$Cl$_2$ and the combined organic layer was washed with H$_2$O (four times), dried over MgSO$_4$, filtered and concentrated. The crude product was subjected to isco purification; 40 g silica cartridge was used and eluted with 0-60% ethyl acetate-hexane mixture. The fractions containing the desired product were combined and concentrated.

The following compounds were made using the above procedure:

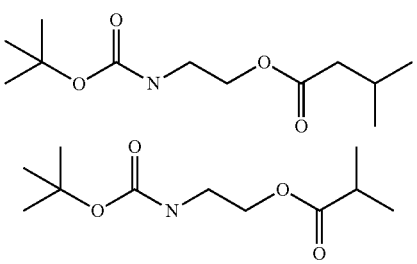

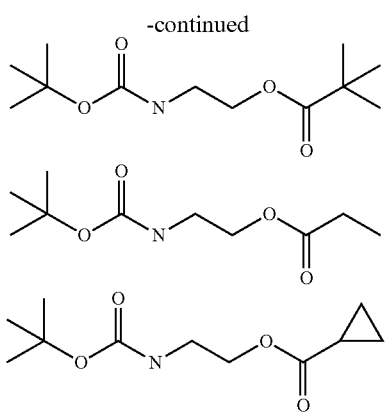

In addition, the present invention includes certain deprotected synthetic intermediates, which may be synthesized using the following general procedure N-BOCglycinol esters (4 mmol) was taken in CH₂Cl₂ (12 mL) at room temperature under nitrogen. HCl/dioxane (4 mL, 4N, 4 eq.) was added and stirred at room temperature for 3 h. At this time TLC showed no starting material remains, hence concentrated. Additional CH₂Cl₂ was added to the residue and again concentrated; this was repeated one additional time and then dried under vacuum, white solids. This HCl was taken to next step.

The following glycinol esters salts were made:

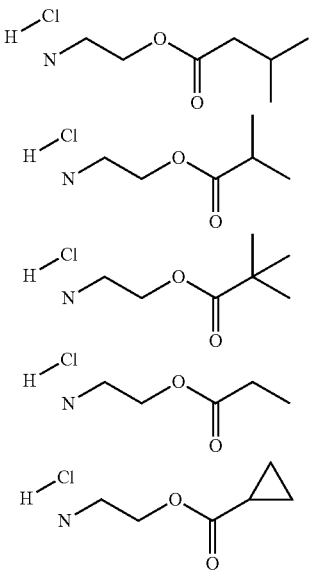

In addition, the present invention includes certain glycinol esters as synthetic intermediates, through reductive amination with 3-formylquinolones, which may be synthesized using the following general procedure:

The 3-formylquinolone (1.5 mmol) and glycinol ester HCl salts (3 mmol, 2 eq) were taken in DMF (9 mL) at room temperature under nitrogen. MgSO₄ (450 mg) was added. The resulting heterogeneous mixture was stirred at room temperature for 3 h. At this time, sodium triacetoxyborohydride (STAB, 1.28 g, 4 eq.) was added and stirring continued. After overnight stirring TLC showed (5% MeOH/CH₂Cl₂) showed more polar spot compared to starting aldehyde. Hence, solid NaHCO₃ (1 g) was added and stirred for 1 h. Diluted with CH₂Cl₂ and filtered via pad of celite. The filter cake was rinsed with CH₂Cl₂ followed by 20% MeOH—CH₂Cl₂. The filtrate was concentrated and purified in an isco, eluting with 0-10% MeOH—CH₂Cl₂. The fractions containing the desired product were combined and concentrated.

In addition, the present invention includes certain urea and thio-urea derivatives, which may be synthesized using the following general procedure:

The reductive amination product (0.15 mmol) and 4-ethoxy phenylisocyanate (0.17 mmol, 1.1 eq) were taken in dioxane (3 mL) and stirred at room temperature overnight under N₂ atmosphere. At this time LC showed major as the desired urea and hence concentrated. The residue was purified in an isco using 12 g cartridge and eluting with 0-70% ethyl acetate-hexanes.

The fractions containing the desired product were combined and concentrated.

In the case of thio urea synthesis, the reaction mixture was heated to 60° C. in dioxane overnight.

Example 49

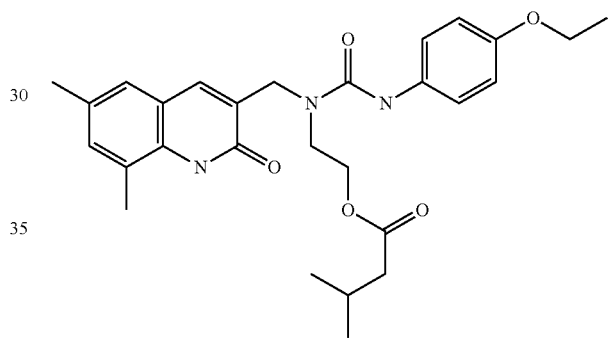

1H NMR (599 MHz, CHLOROFORM-d) δ ppm 0.84-0.93 (m, 6H) 1.32-1.39 (m, 3H) 1.99-2.08 (m, 1H) 2.08-2.13 (m, 2H) 2.40 (s, 3H) 2.48 (s, 3H) 3.55-3.63 (m, 2H) 3.92-4.02 (m, 2H) 4.29 (t, J=6.15 Hz, 2H) 4.51 (s, 2H) 6.81 (d, J=9.22 Hz, 2H) 7.27 (s, 1H) 7.32 (s, 1H) 7.35 (d, J=9.22 Hz, 2H) 8.00 (br. s., 1H). LCMS ESI (M+H): 494

Example 50

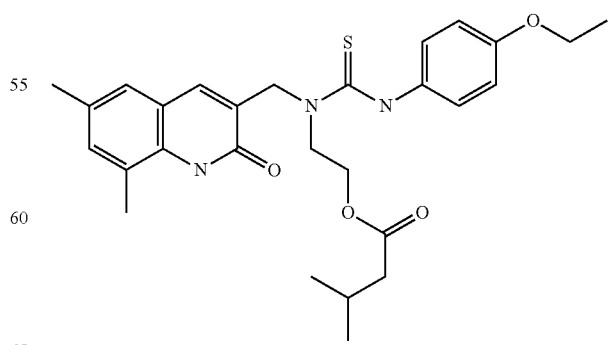

LCMS ESI (M+H): 510

Example 51

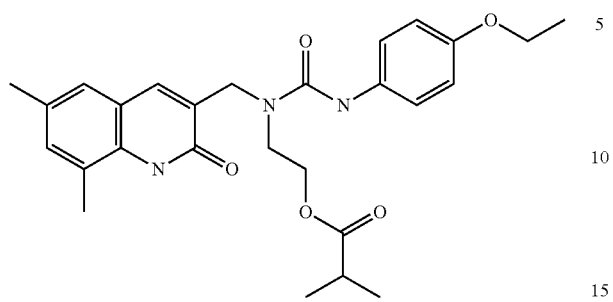

1H NMR (599 MHz, DMSO-$d_6$) δ ppm 0.96 (d, 6H) 1.26 (t, J=7.03 Hz, 3H) 2.27 (s, 3H) 2.33 (ddd, J=13.73, 7.03, 6.92 Hz, 1H) 2.37-2.41 (m, 3H) 3.56 (t, J=5.05 Hz, 2H) 3.92 (q, J=7.03 Hz, 2H) 4.13 (t, J=5.49 Hz, 2H) 4.40 (s, 2H) 6.74-6.84 (m, 2H) 7.17 (s, 1H) 7.25-7.35 (m, 3H) 7.78 (s, 1H) 9.32 (br. s., 1H). LCMS ESI (M+H): 480

Example 52

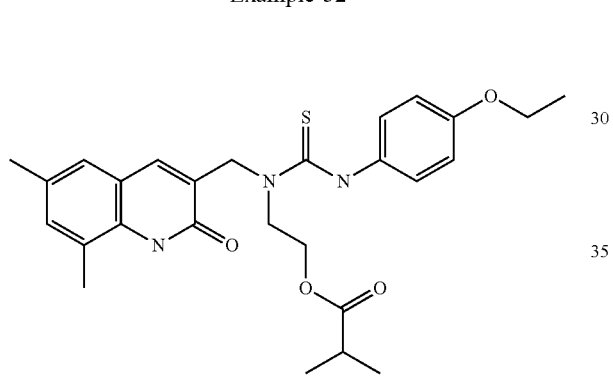

1H NMR (599 MHz, DMSO-$d_6$) δ ppm 0.98 (d, J=7.03 Hz, 6H) 1.25-1.31 (m, 3H) 2.28 (s, 3H) 2.31-2.38 (m, 1H) 2.39 (s, 3H) 3.96 (q, J=7.03 Hz, 2H) 4.05 (t, J=5.27 Hz, 2H) 4.27 (t J=5.71 Hz, 2H) 4.76 (br. s., 2H) 6.83 (d, J=9.22 Hz, 2H) 7.16-7.25 (m, 3H) 7.33 (s, 1H) 7.80 (br. s., 1H). LCMS ESI (M+H): 496

Example 53

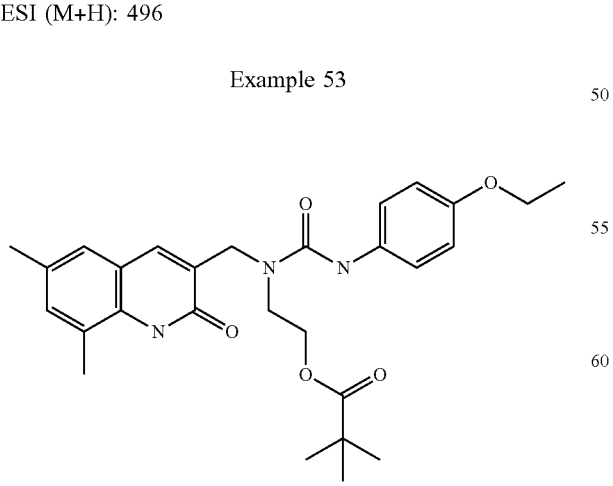

LCMS ESI (M+H): 494

Example 54

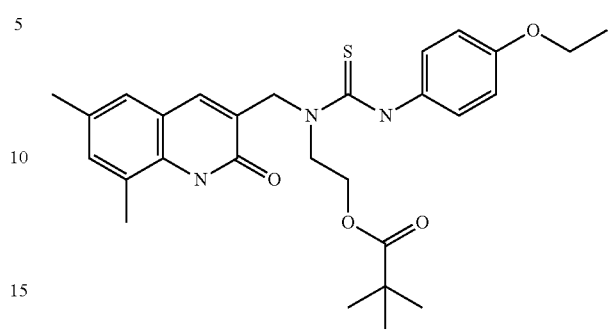

LCMS ESI (M+H): 510

Example 55

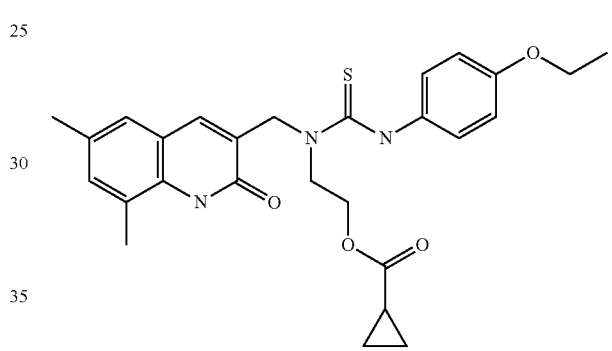

LCMS ESI (M+H): 494

Example 56

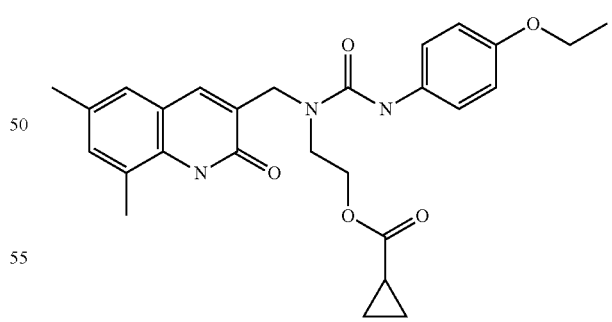

1H NMR (599 MHz, DMSO-$d_6$) δ ppm 0.65-0.78 (m, 4H) 1.25 (t, J=6.88 Hz, 3H) 1.40 (br. s., 1H) 2.28 (s, 3H) 2.38 (s, 3H) 3.51-3.60 (m, 2H) 3.87-3.98 (m, 2H) 4.12 (d, J=5.27 Hz, 2H) 4.40 (br. s., 2H) 6.67-6.88 (m, 2H) 7.17 (br. s., 1H) 7.29 (d, J=8.20 Hz, 3H) 7.78 (br. s., 1H) 9.35 (br. s., 1H) 11.26 (br. s., 1H). LCMS ESI (M+H): 478

Example 57

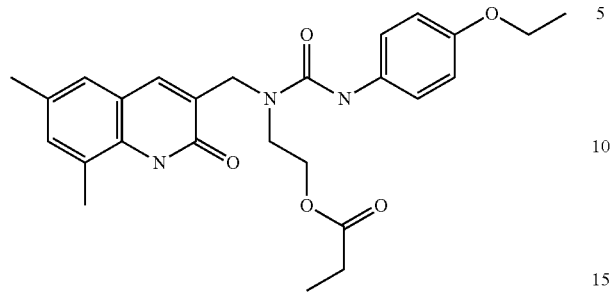

1H NMR (500 MHz, DMSO-d$_6$) δ ppm 0.90 (t, J=7.58 Hz, 3H) 1.25-1.31 (m, 3H) 2.30 (s, 3H) 2.40 (s, 3H) 3.52-3.60 (m, 2H) 3.90-3.99 (m, 2H) 4.15 (t, J=5.62 Hz, 2H) 4.42 (s, 2H) 6.77-6.85 (m, 2H) 7.20 (s, 1H) 7.26-7.35 (m, 3H) 7.81 (s, 1H) 9.39 (br. s., 1H) 11.30 (br. s., 1H). LCMS ESI (M+H): 466

Example 58

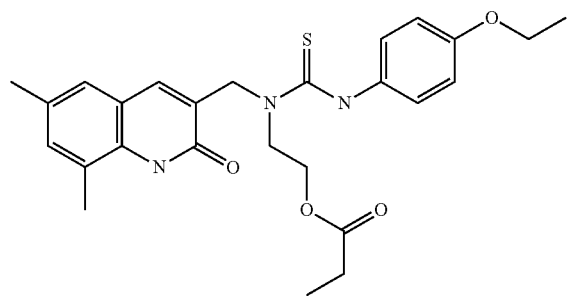 [SMILES: CCOc1ccc(NC(=S)N(CCOC(=O)CC)Cc2cc3cc(C)cc(C)c3[nH]c2=O)cc1]

LCMS ESI (M+H): 482

Synthesis Scheme 3
In addition, several compounds were made by the following synthetic schemes

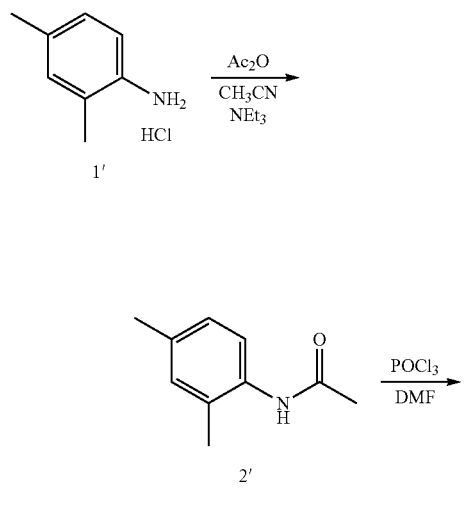

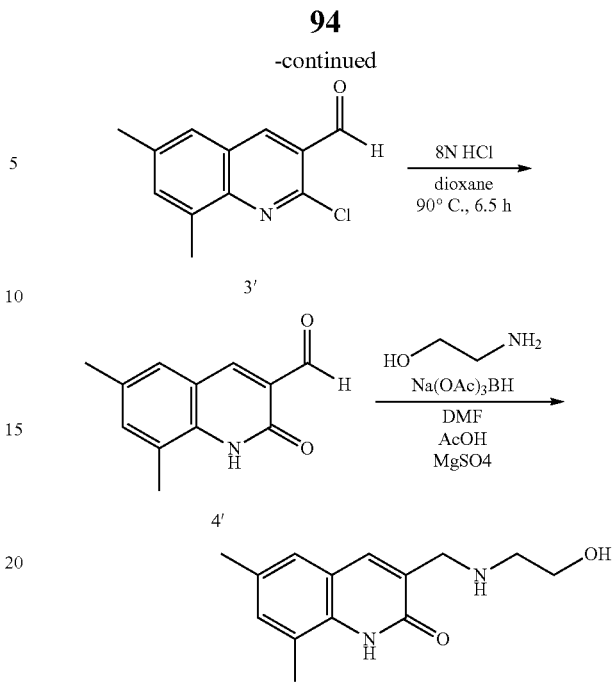

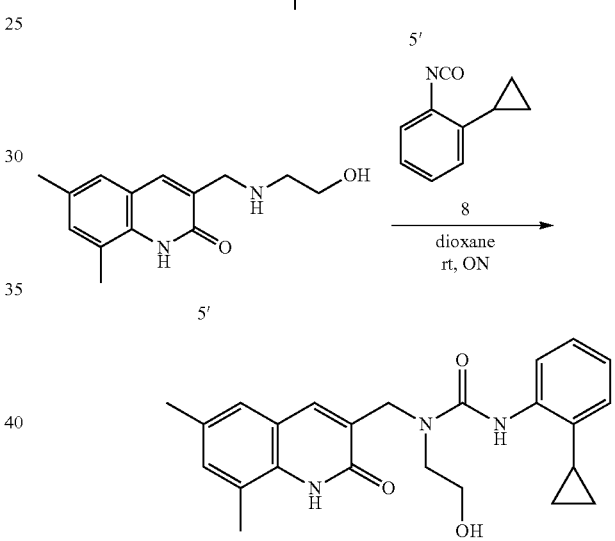

Example 59

(6'): 3-(2-Cyclopropylphenyl)-1-[(6,8-dimethyl-2-oxo-1H-quinolin-3-yl)methyl]-1-(2-hydroxyethyl)urea: To a suspension of compound 5' (75 mg, 0.3 mmol) in dioxane (2 mL) was added compound 8 (53.3 mg, 0.33 mmol). The reaction mixture was stirred at room temperature overnight. Then the solvent was concentrated and the crude was purified by column chromatography (silica gel, ethyl acetate/hexanes gradient 0-100%) to give 15 mg of compound 6 as a white solid (12%).

1H NMR (500 MHz, CHLOROFORM-d) δ ppm 0.57-0.62 (m, 2H) 0.85-0.91 (m, 2H) 2.40 (s, 3H) 2.47 (br. s., 3H) 3.59-3.63 (m, 2H) 3.90-3.95 (m, 2H) 4.59 (s, 2H) 6.94-7.00 (m, 1H) 7.04-7.07 (m, 1H) 7.15-7.20 (m, 1H) 7.28-7.33 (m, 1H) 7.79-7.83 (m, 1H) 7.89-7.97 (m, 1H) 8.58-8.66 (m, 1H). LCMS ESI (M+H) 406

Example 60

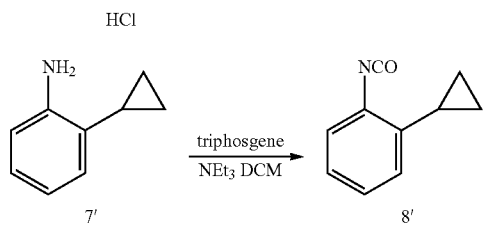

(8'): 1-cyclopropyl-2-isocyanato-benzene: Compound 7' (0.64 g, 0.0038 mol) was dissolved in DCM (38 mL). Then triethylamine (1.1 mL, 0.0076 mol) and triphosgene (0.45 g, 0.0015 mol) were added. The mixture was heated at reflux under nitrogen for 2 hours. The reaction mixture was washed with water and the organic layer was dried over magnesium sulfate to give 690 mg of a brown oil.

Example 61

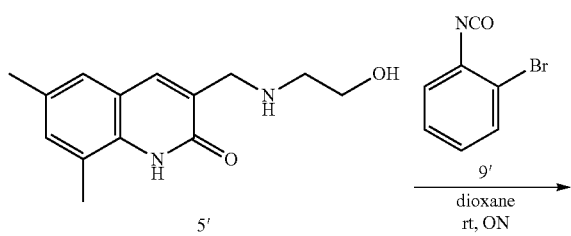

(10'): 3-(2-Bromophenyl)-1-[(6,8-dimethyl-2-oxo-1H-quinolin-3-yl)methyl]-1-(2-hydroxyethyl)urea: To a suspension of compound 5' (75 mg, 0.3 mmol) in dioxane (2 mL) was added compound 9' (42 uL, 0.34 mmol). The reaction mixture was stirred at room temperature for 24 h. Then the solvent was concentrated and the crude was purified by column chromatography (silica gel, ethyl acetate/hexanes gradient 0-100%) to give 27 mg of compound 10 as a white solid (20%).

1H NMR (500 MHz, DMSO-$d_6$) δ ppm 2.29 (s, 3H) 2.39 (s, 3H) 3.42-3.49 (m, 2H) 3.59-3.66 (m, 2H) 4.41-4.47 (m, 2H) 6.92-6.98 (m, 1H) 7.15-7.18 (m, 1H) 7.26-7.34 (m, 2H) 7.54-7.58 (m, 1H) 7.70-7.81 (m, 2H) 8.84-8.94 (m, 1H) 11.03-11.13 (m, 1H). LCMS ESI (M+H) 444,446; 466,468

Example 62

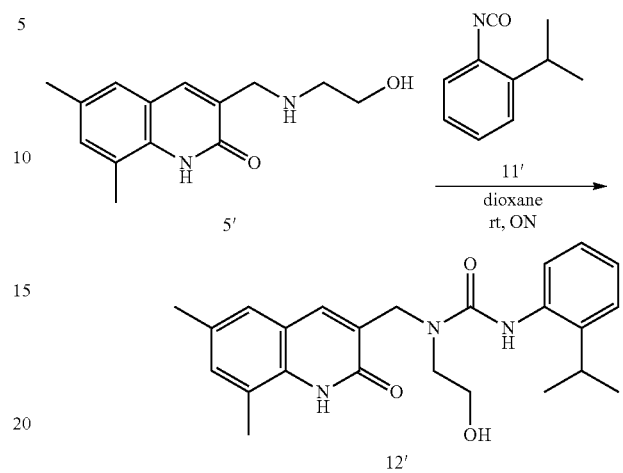

(12'): 1-[(6,8-dimethyl-2-oxo-1H-quinolin-3-yl)methyl]-1-(2-hydroxyethyl)-3-(2-isopropylphenyl)urea: To a suspension of compound 5' (75 mg, 0.3 mmol) in dioxane (2 mL) was added compound 1T (53 uL, 0.34 mmol). The reaction mixture was stirred at room temperature for 40 h. Then the solvent was concentrated and the crude was purified by column chromatography (silica gel, ethyl acetate/hexanes gradient 0-100%) to give 33 mg of compound 12 as a white solid (27%).

1H NMR (500 MHz, DMSO-$d_6$) δ ppm 1.10-1.15 (m, 6H) 2.29-2.31 (m, 3H) 2.39-2.42 (m, 3H) 3.13-3.21 (m, 1H) 3.40-3.46 (m, 2H) 3.57-3.63 (m, 2H) 4.41-4.46 (m, 2H) 7.03-7.11 (m, 2H) 7.16-7.19 (m, 1H) 7.21-7.25 (m, 1H) 7.28-7.32 (m, 2H) 7.63-7.77 (m, 1H) 8.57-8.70 (m, 1H) 11.05-11.14 (m, 1H). LCMS ESI (M+Na) 430

Example 63

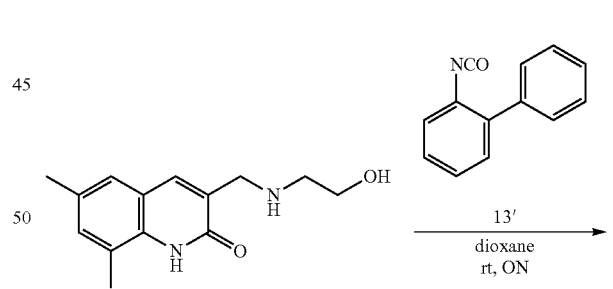

(14'): 1-[(6,8-dimethyl-2-oxo-1H-quinolin-3-yl)methyl]-1-(2-hydroxyethyl)-3-(2-phenylphenyl)urea: To a suspension of compound 5' (30 mg, 0.1 mmol) in dioxane (1 mL)

was added compound 13' (0.026 g, 0.13 mmol). The reaction mixture was stirred at room temperature overnight. Then the solvent was concentrated and the crude was triturated with methanol to give 4 mg of a white solid (8%).

1H NMR (500 MHz, DMSO-$d_6$) δ ppm 2.30 (s, 3H) 2.38 (s, 3H) 3.39 (d, J=4.40 Hz, 2H) 3.42 (m, 2H) 4.26 (s, 2H) 7.06-7.35 (m, 8H) 7.42 (br. s., 1H) 7.61 (d, J=7.83 Hz, 1H) 8.13 (s, 1H) 10.97 (br. s., 1H). LCMS ESI (M+H) 442

Example 64

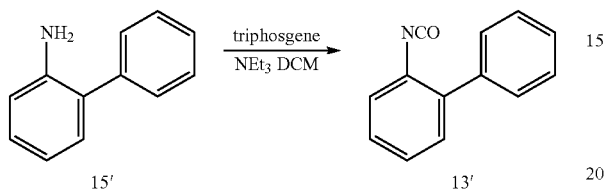

(13'): 1-isocyanato-2-phenyl-benzene: Compound 15' (1 g, 0.0059 mol) was dissolved in DCM (50 mL). Then triethylamine (1.6 mL, 0.0118 mol) and triphosgene (0.7 g, 0.0024 mol) were added. The mixture was heated at reflux under nitrogen for 2 hours. The reaction mixture was washed with water and the organic layer was dried over magnesium sulfate to give 1.15 g of a brown oil.

Example 65

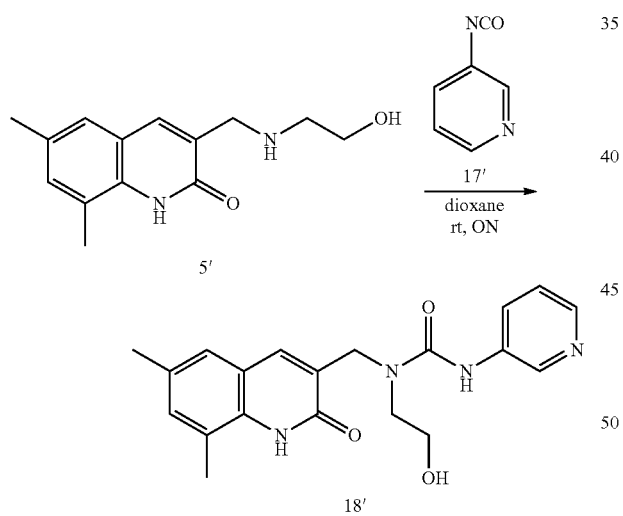

(18'): 1-[(6,8-dimethyl-2-oxo-1H-quinolin-3-yl)methyl]-1-(2-hydroxyethyl)-3-(3-pyridyl)urea: To a suspension of compound 5' (50 mg, 0.2 mmol) in dioxane (2 mL) was added compound 17' (0.027 g, 0.22 mmol). The reaction mixture was stirred at room temperature overnight. Then the solvent was concentrated and the crude was purified by column chromatography (silica gel, ethyl acetate/hexanes gradient 0-45%) to give 23 mg of compound 18 as a white solid (31%).

1H NMR (500 MHz, CHLOROFORM-d) δ ppm 2.37 (s, 3H) 2.45 (s, 3H) 3.52 (t, J=4.40 Hz, 2H) 3.91 (t, J=4.65 Hz, 2H) 4.48 (s, 2H) 7.20 (s, 1H) 7.23 (s, 1H) 7.76 (s, 1H) 7.96 (d, J=7.83 Hz, 1H) 8.16 (br. s., 1H) 8.61 (br. s., 1H) 9.57-9.73 (m, 1H). LCMS ESI (M+H) 367

Example 66

(17'): 3-isocyanatopyridine: Compound 16' (1 g, 0.01 mol) was dissolved in DCM (50 mL). Then triethylamine (2.8 mL, 0.02 mol) and triphosgene (1.26 g, 0.0043 mol) were added. The mixture was heated at reflux under nitrogen for 2.5 hours. The reaction mixture was washed with water and the organic layer was dried over magnesium sulfate to give 0.5 g of a brown oil.

Example 67

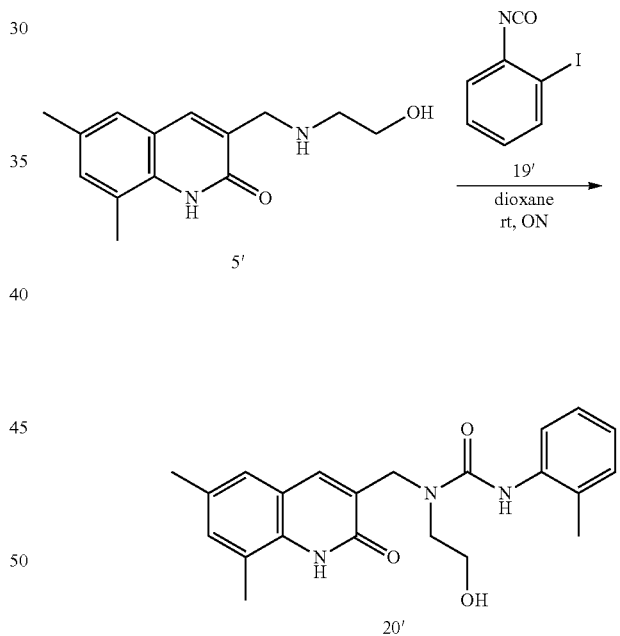

(20'): 1-[(6,8-dimethyl-2-oxo-1H-quinolin-3-yl)methyl]-1-(2-hydroxyethyl)-3-(2-iodophenyl)urea: To a suspension of compound 5' (50 mg, 0.2 mmol) in dioxane (2 mL) was added compound 19' (0.054 g, 0.22 mmol). The reaction mixture was stirred at room temperature overnight. Then the solvent was concentrated and the crude triturated with DCM to give 35 mg of a yellow solid (35%).

1H NMR (500 MHz, DMSO-$d_6$) δ ppm 2.30 (s, 3H) 2.40 (s, 3H) 3.41-3.49 (m, 2H) 3.56-3.69 (m, 2H) 4.46 (br. s., 1H) 6.84 (s, 1H) 7.17 (s, 1H) 7.28-7.36 (m, 1H) 7.58 (s, 1H) 7.72-7.77 (m, 1H) 7.81 (d, J=7.83 Hz, 1H) 11.08 (br. s., 1H). LCMS ESI (M+H) 492

Example 68

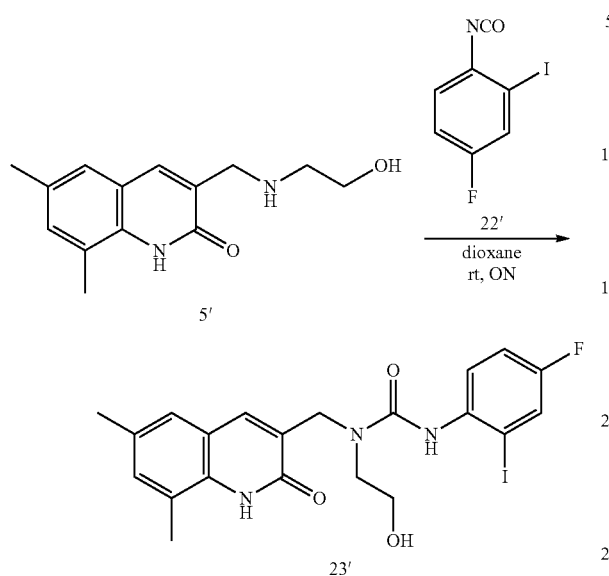

(23'): 1-[(6,8-dimethyl-2-oxo-1H-quinolin-3-yl)methyl]-3-(4-fluoro-2-iodo-phenyl)-1-(2-hydroxyethyl)urea: To a suspension of compound 5' (50 mg, 0.2 mmol) in dioxane (2 mL) was added compound 22' (0.058 g, 0.22 mmol). The reaction mixture was stirred at room temperature overnight. Then 26 mg more of 22' (0.5 eq) were added and the mixture stirred at room temperature for 24 hours. Then the solvent was concentrated and the crude triturated with DCM to give 15 mg of a white solid (15%).

1H NMR (500 MHz, DMSO-$d_6$) δ ppm 2.29 (s, 3H) 2.39 (s, 3H) 3.45 (br. s., 2H) 3.62 (br. s., 2H) 4.46 (br. s., 2H) 7.17 (s, 1H) 7.21 (dd, J=8.31, 5.87 Hz, 1H) 7.33 (s, 1H) 7.51 (dd, J=9.05, 5.62 Hz, 1H) 7.69 (dd, J=8.31, 2.93 Hz, 1H) 7.72-7.77 (m, 1H) 8.65-8.81 (m, 1H) 11.09 (br. s., 1H). LCMS ESI (M+H) 510

Example 69

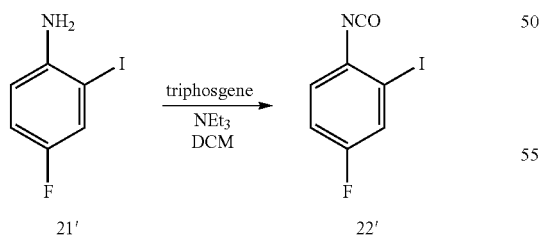

(22'): 4-fluoro-2-iodo-1-isocyanato-benzene: Compound 2T (1 g, 0.0042 mol) was dissolved in DCM (44 mL). Then triethylamine (1.2 mL, 0.0084 mol) and triphosgene (0.5 g, 0.0017 mol) were added. The mixture was heated at reflux under nitrogen for 4 hours. The reaction mixture was washed with water and the organic layer was dried over magnesium sulfate to give 1 g of a yellow solid.

Example 70

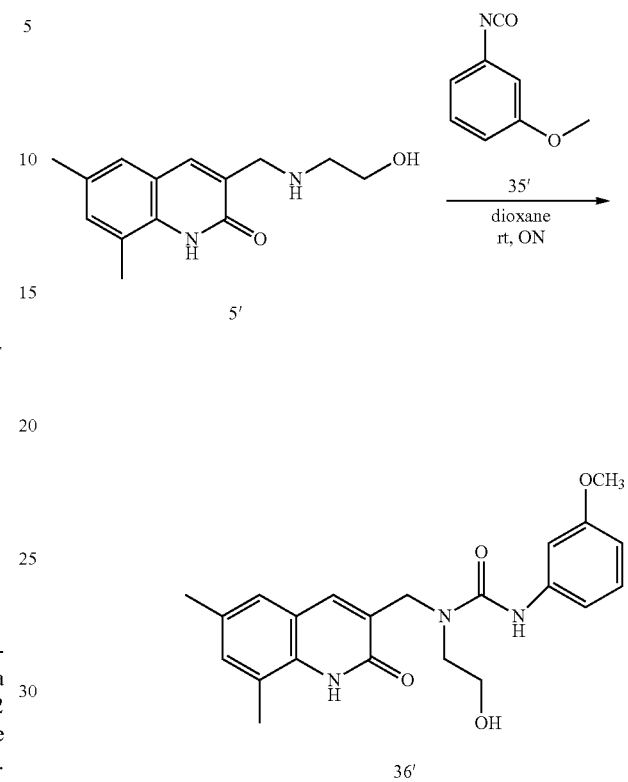

(36'): 1-[1-(6,8-dimethyl-2-oxo-1H-quinolin-3-yl)ethyl]-1-(2-hydroxyethyl)-3-(3-methoxyphenyl)urea: To a suspension of compound 5' (25 mg, 0.096 mmol) in dioxane (1 mL) was added compound 35' (14 uL, 0.1 mmol). The reaction mixture was stirred at room temperature overnight. Solvent was removed and crude purified by silica gel column chromatography (ethyl acetate/hexanes gradient 0-100%) to give 10 mg of a white solid (25%). 1H NMR (500 MHz, DMSO-$d_6$) δ ppm 2.29 (s, 3H) 2.39 (s, 3H) 3.37-3.42 (m, 2H) 3.54-3.62 (m, 2H) 3.69 (s, 1H) 4.43 (s, 1H) 4.98 (br. s., 1H) 6.46-6.52 (m, 1H) 6.94-6.99 (m, 1H) 7.10-7.15 (m, 1H) 7.18-7.21 (m, 1H) 7.28-7.38 (m, 1H) 7.73-7.85 (m, 1H) 11.16-11.28 (m, 1H). LCMS ESI (M+H) 396

Example 71

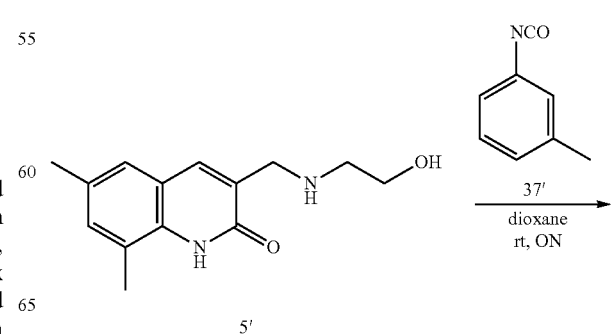

-continued

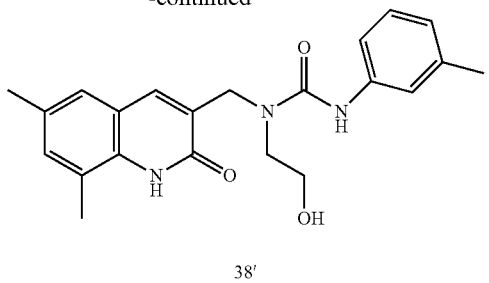

38'

(38'): 1-[(6,8-dimethyl-2-oxo-1H-quinolin-3-yl)methyl]-1-(2-hydroxyethyl)-3-(m-tolyl)urea: To a suspension of compound 5' (25 mg, 0.096 mmol) in dioxane (1 mL) was added compound 37' (14 uL, 0.1 mmol). The reaction mixture was stirred at room temperature overnight. Solvent was removed and was purified by trituration with dichloromethane to give 16 mg of a yellow solid (41%).

1H NMR (500 MHz, DMSO-$d_6$) δ ppm 2.23 (s, 3H) 2.30 (s, 3H) 2.41 (s, 3H) 3.36-3.44 (m, 2H) 3.58 (q, J=5.05 Hz, 2H) 4.43 (s, 2H) 4.99 (br. s., 1H) 7.10 (t, J=7.83 Hz, 1H) 7.18-7.25 (m, 3H) 7.33 (s, 1H) 7.80 (s, 1H) 11.25 (br. s., 1H). LCMS ESI (M+H) 380; (M+Na) 402

Example 72

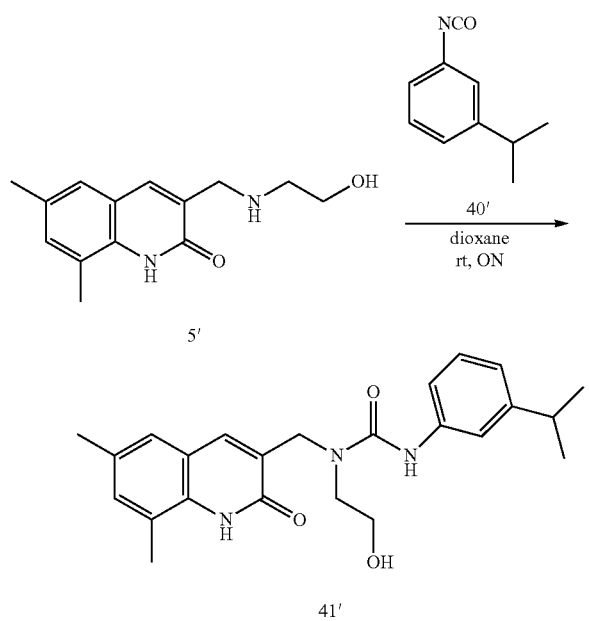

(41'): 1-[(6,8-dimethyl-2-oxo-1H-quinolin-3-yl)methyl]-1-(2-hydroxyethyl)-3-(3-isopropylphenyl)urea: To a suspension of compound 5' (25 mg, 0.096 mmol) in dioxane (1 mL) was added compound 40' (18 mg, 0.1 mmol). The reaction mixture was stirred at room temperature overnight. Solvent was removed and was purified by trituration with 5% ethyl acetate/hexanes to give 11 mg of a yellow solid (27%).

1H NMR (500 MHz, DMSO-$d_6$) δ ppm 1.14-1.21 (m, 6H) 2.29 (s, 3H) 2.41 (s, 3H) 2.74-2.83 (m, 1H) 3.38-3.42 (m, 2H) 3.56-3.62 (m, 2H) 4.44 (s, 1H) 6.79 (d, J=7.83 Hz, 1H) 7.13 (t, J=7.56 Hz, 1H) 7.19 (s, 1H) 7.24-7.29 (m, 1H) 7.33 (s, 1H) 7.78 (s, 1H) 9.44 (br. s., 1H) 11.22 (br. s., 1H). LCMS ESI (M+H) 408

Example 73

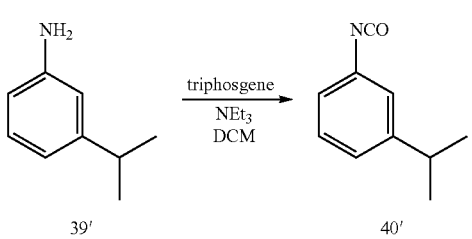

(40'): 1-isocyanato-3-isopropyl-benzene: Compound 39' (1 g, 0.0074 mol) was dissolved in DCM (40 mL). Then triethylamine (2 mL, 0.0148 mol) and triphosgene (0.88 g, 0.0029 mol) were added. The mixture was heated at reflux under nitrogen for 4 hours. The reaction mixture was washed with water and the organic layer was dried over magnesium sulfate to give 1.2 g of a brown oil.

Example 74

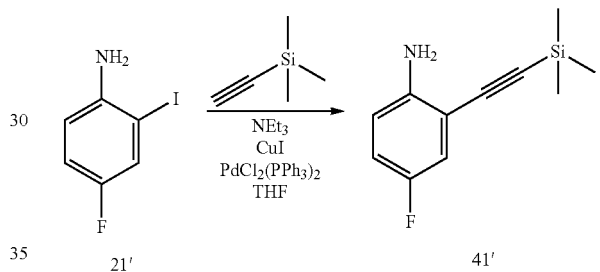

(41'): 4-fluoro-2-(2-trimethylsilylethynyl)aniline: Compound 21' (1 g, 0.0042 mol) was dissolved in THF (20 mL). Then triethylamine (3.5 mL, 0.0252 mol) and ethynyl(trimethyl)silane (0.6 mL, 0.005 mol) were added and the mixture bubbled with nitrogen for 5 minutes. Then CuI (0.16 g, 0.00084 mol) and PdCl$_2$(PPh$_3$)$_2$ (0.29 g, 0.00042 mol) were added. The mixture was stirred at room temperature for 2.5 hours and filtered through celite. The filtrate was concentrated and the crude purified by plug of silica gel (gradient ethyl acetate/hexanes 2-5%) to give 654 mg of a yellow liquid (75%).

1H NMR (500 MHz, CHLOROFORM-d) δ ppm 0.26 (s, 9H) 6.62 (dd, J=8.80, 4.40 Hz, 1H) 6.85 (td, J=8.56, 2.93 Hz, 1H) 6.99 (dd, J=8.80, 2.93 Hz, 1H). LCMS ESI (M+H) 208

Example 75

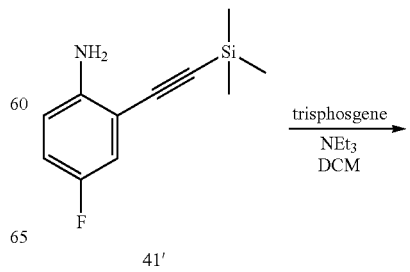

41'

103

-continued

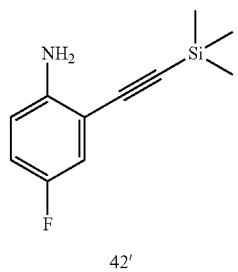

42'

(42'): 2-(5-fluoro-2-isocyanato-phenyl)ethynyl-trimethylsilane: Compound 4T (0.65 g, 0.0031 mol) was dissolved in DCM (40 mL). Then triethylamine (0.85 mL, 0.0062 mol) and triphosgene (0.37 g, 0.00126 mol) were added. The mixture was heated at reflux under nitrogen for 6 hours. The reaction mixture was washed with water and the organic layer was dried over magnesium sulfate to give 0.727 g of a brown oil.

Example 76

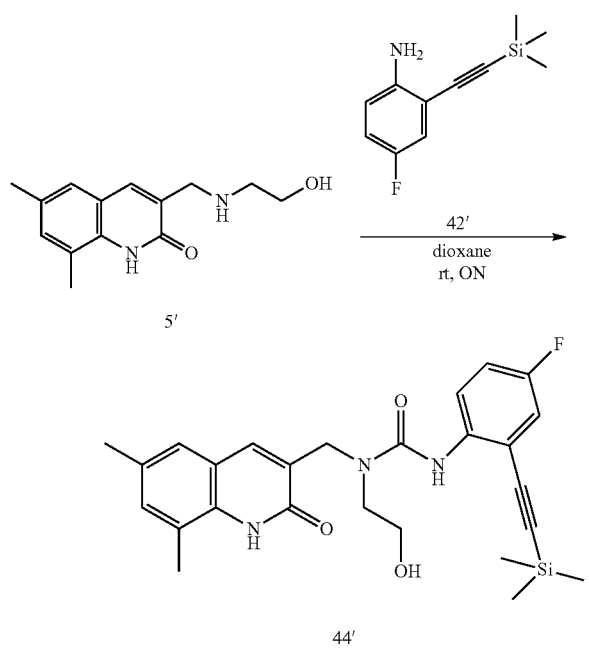

44'

(44'): 1-[(6,8-dimethyl-2-oxo-1H-quinolin-3-yl)methyl]-1-(2-hydroxyethyl)-3-[4-methyl-2-(2-trimethylsilylethynyl)phenyl]urea: To a suspension of compound 5' (25 mg, 0.096 mmol) in dioxane (1 mL) was added compound 42' (26 mg, 0.1 mmol). The reaction mixture was stirred at room temperature overnight Solvent was removed and was purified by trituration with 5% ethyl acetate/hexanes to give 16 mg of a yellow oil (33%).

1H NMR (500 MHz, DMSO-$d_6$) δ ppm 0.18 (s, 9H) 2.28 (s, 3H) 2.38 (s, 3H) 3.41-3.47 (m, 2H) 3.58-3.63 (m, 2H) 4.44 (s, 2H) 7.14-7.20 (m, 2H) 7.23 (dd, J=8.80, 2.93 Hz, 1H) 7.32 (s, 1H) 7.74 (br. s., 1H) 8.03 (dd, J=9.05, 5.14 Hz, 1H) 11.10 (br. s., 1H). LCMS ESI (M+H) 480

104

Example 77

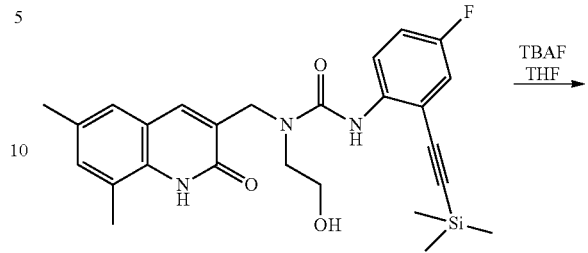

44'

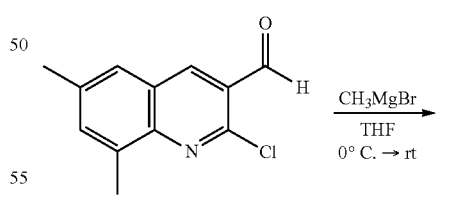

45'

(44'): 1-[(6,8-dimethyl-2-oxo-1H-quinolin-3-yl)methyl]-3-(2-ethynyl-4-fluoro-phenyl)-1-(2-hydroxyethyl)urea: To a solution of compound 43' (0.03 g, 0.063 mmol) in THF (1 mL), was added TBAF.3H$_2$O (22 mg, 0.069 mmol) and the mixture was stirred at room temperature for 1 hour. Then, water (300 mL) and ethyl acetate (200 ml) were added to the reaction mixture. The organic layer was dried over magnesium sulfate and the solvent removed. The crude was purified by silica gel plug (gradient methanol/DCM 5-15%) to give 12 mg of a yellow solid (50%).

1H NMR (500 MHz, DMSO-$d_6$) δ ppm 2.29 (s, 3H) 2.39 (s, 3H) 3.41-3.48 (m, 3H) 3.61 (t, J=4.89 Hz, 2H) 4.37-4.46 (m, 3H) 7.15-7.21 (m, 2H) 7.26 (dd, J=8.80, 2.93 Hz, 1H) 7.31 (s, 1H) 7.70 (br. s., 1H) 7.86 (dd, J=9.29, 5.38 Hz, 1H) 8.88 (s, 1H) 11.03 (br. s., 1H). LCMS ESI (M+H) 408

Example 78

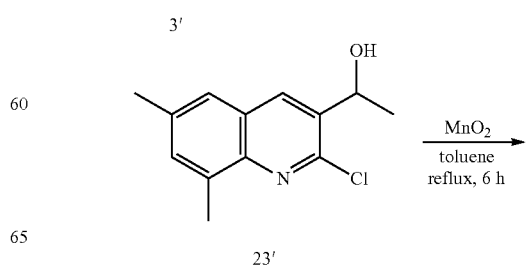

105

-continued

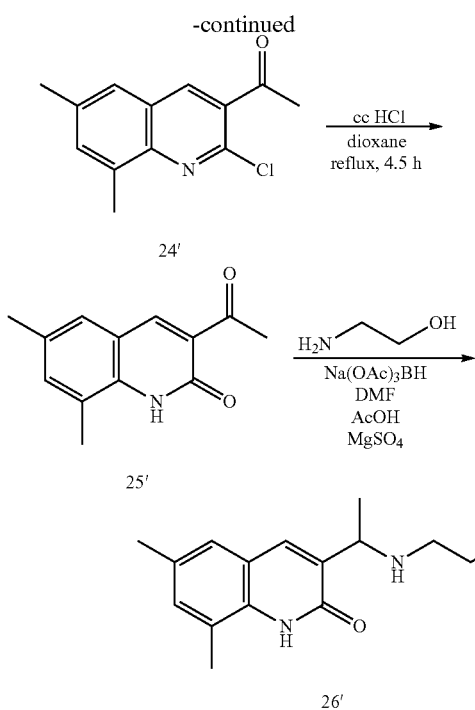

(23'): 1-(2-chloro-6,8-dimethyl-3-quinolyl)ethanol: Compound 3' (2 g, 0.0091 mol) was dissolved in THF (30 mL) and CH₃MgBr (4.6 mL of a 3M solution in ether, 0.013 mol) was added dropwise at 0° C. The temperature was allowed to reach room temperature and the mixture was stirred at this temperature overnight.

Saturated solution of NH₄Cl and ether were added to the reaction mixture at 0° C. and stirred for 10 minutes. Organic layer was separated, washed with water and dried over sodium sulfate, filtered and solvent removed to give 1.9 g of a brown oil (94% crude).

Example 79

(24'): 1-(2-chloro-6,8-dimethyl-3-quinolyl)ethanone: Compound 23' (1.9 g, 0.0086 mol) was dissolved in toluene (70 mL). MnO₂ was added (5.9 g, 0.068 mol) and the mixture was heated at reflux for 4 hours. Then 1 g of MnO₂ (1.4 eq) was added and the mixture refluxed for 2 more hours. The reaction mixture was then filtered through celite and washed with DCM. The filtrate was concentrated to give 1.54 g of an orange oil (82% crude).

1H NMR (500 MHz, CHLOROFORM-d) δ ppm 2.50 (s, 3H) 2.74 (s, 3H) 2.76 (s, 3H) 7.48 (s, 1H) 7.50 (s, 1H) 8.26 (s, 1H)

Example 80

(25'): 3-acetyl-6,8-dimethyl-1H-quinolin-2-one: Compound 24' (0.5 g, 0.0023 mol) was dissolved in dioxane (10 mL) and cc HCl (40 mL, 0.48 mol) was added. The mixture was heated at reflux for 4.5 hours. Dioxane was evaporated and the aqueous layer was extracted with DCM and washed with ss NaHCO₃, and brine, dried over sodium sulfate and solvent removed to give 0.47 g of a yellow solid (96% crude).

1H NMR (500 MHz, CHLOROFORM-d) δ ppm 2.39 (s, 3H) 2.50 (s, 3H) 2.78 (s, 3H) 7.28 (s, 1H) 7.34 (s, 1H) 8.47 (s, 1H) 9.87 (br. s., 1H)

106

Example 81

(26'): 3-[1-(2-hydroxyethylamino)ethyl]-6,8-dimethyl-1H-quinolin-2-one: Compound 25' (0.27 g, 0.0013 mol) was dissolved in DMF (10 mL). Ethanolamine (0.11 mL, 0.0018 mol), acetic acid (70 uL), MgSO₄ (0.4 g, 0.003 mol) and Na(OAc)₃BH (1.08 g, 0.005 mol) were added and the mixture stirred at 50° C. overnight. Then 0.25 g (0.0012 mol) of reducing agent were added and heated at reflux for 2 hours. Methanol/DCM (1/1, 20 mL) was added and the mixture stirred at room temperature for 1 hour. The reaction mixture was filtered through celite. The filtrate was concentrated and purified by a silica gel plug (methanol/dichloromethane gradient 0-5%) to give 256 mg of a yellow solid (78% from compound 25 crude).

LCMS ESI (M+H) 261

Example 82

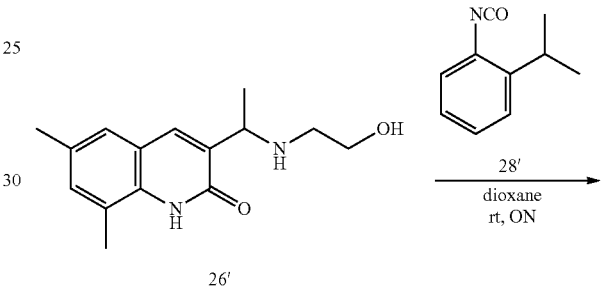

(29'), 1-[1-(6,8-dimethyl-2-oxo-1H-quinolin-3-yl)ethyl]-1-(2-hydroxyethyl)-3-(2-isopropylphenyl)urea: To a suspension of compound 26' (25 mg, 0.096 mmol) in dioxane (1 mL) was added compound 28' (0.017 g, 0.1 mmol). The reaction mixture was stirred at room temperature for 2 days. Then the solvent was concentrated and the crude triturated with 5% ethyl acetate/hexanes to give 22 mg of a yellow solid (55%).

1H NMR (500 MHz, DMSO-d₆) δ ppm 1.13 (d, J=6.85 Hz, 6H) 1.50 (d, J=7.34 Hz, 3H) 2.30 (s, 3H) 2.40 (s, 3H) 3.09-3.21 (m, 1H) 3.17 3.33-3.42 (m, 4H) 5.34-5.42 (m, 1H) 7.01 (t, J=7.34 Hz, 1H) 7.04-7.09 (m, 1H) 7.18 (s, 1H) 7.22 (d, J=7.34 Hz, 1H) 7.34-7.38 (m, 2H) 7.88 (s, 1H) 8.79 (br. s., 1H) 11.03 (br. s., 1H)

Example 83

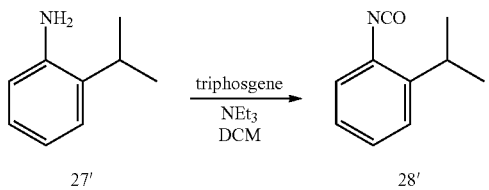

(28'): 1-isocyanato-2-isopropyl-benzene: Compound 27' (2 g, 0.015 mol) was dissolved in DCM (80 mL). Then triethylamine (4.2 mL, 0.03 mol) and triphosgene (1.76 g, 0.006 mol) were added. The mixture was heated at reflux under nitrogen for 3 hours, then 0.8 g of triphosgene (0.5 eq) were added and heated at reflux for 2 more hours. The reaction mixture was washed with water and the organic layer was dried over magnesium sulfate to give 2.2 g of a brown oil.

Example 84

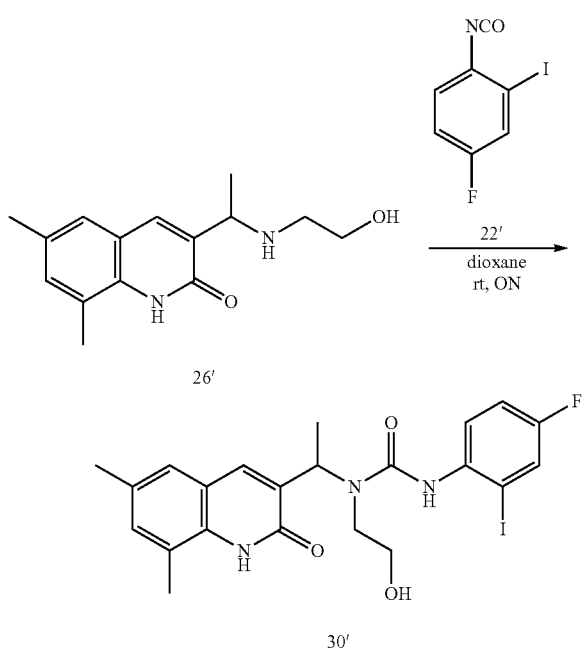

(30'): 1-[1-(6,8-dimethyl-2-oxo-1H-quinolin-3-yl)ethyl]-3-(4-fluoro-2-iodo-phenyl)-1-(2-hydroxyethyl)urea: To a suspension of compound 26' (25 mg, 0.096 mmol) in dioxane (1 mL) was added compound 22' (0.028 g, 0.1 mmol). The reaction mixture was stirred at room temperature overnight. Then the solvent was concentrated and 10% methanol/DCM was added. The solid was filtered and the filtrate containing the product (30) was concentrated to give 4 mg of 30 (8%).

1H NMR (500 MHz, DMSO-$d_6$) δ ppm 1.57 (s, 3H) 2.29 (s, 3H) 2.36 (s, 3H) 3.3-3.46 (m, 4H) 5.4 (m, 1H) 7.15 (s, 1H) 7.25 (m, 1H) 7.33 (s, 1H) 7.51 (m, 1H) 7.70 (m, 1H) 7.72-7.75 (m, 1H) 8.65 (s, 1H) 11.0 (br. s., 1H). LCMS ESI (M+H) 524

Example 85

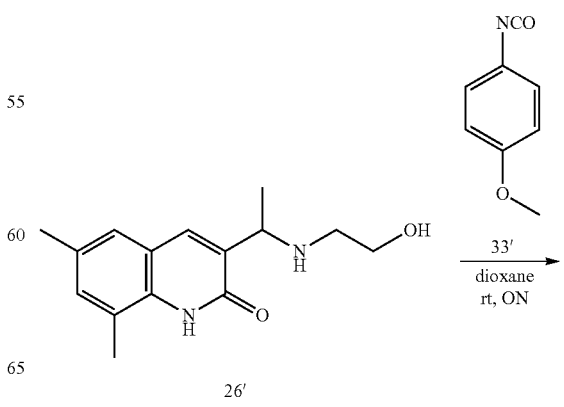

(31'): 1-[1-(6,8-dimethyl-2-oxo-1H-quinolin-3-yl)ethyl]-1-(2-hydroxyethyl)-3-(o-tolyl)urea: To a suspension of compound 26' (25 mg, 0.096 mmol) in dioxane (1 mL) was added compound 32' (0.028 g, 0.1 mmol). The reaction mixture was stirred at room temperature overnight. The solid was filtered to give 9 mg of 31 as a yellow solid (24%).

1H NMR (500 MHz, DMSO-$d_6$) δ ppm 1.47-1.55 (m, 3H) 2.23 (s, 3H) 2.31 (s, 3H) 2.40 (s, 3H) 3.20-3.44 (m, 4H) 5.34-5.42 (m, 1H) 6.89 (t J=7.41 Hz, 1H) 7.04-7.14 (m, 2H) 7.19 (s, 1H) 7.36 (s, 1H) 7.52 (d, J=8.23 Hz, 1H) 7.91 (s, 1H) 8.93 (br. s., 1H) 11.06 (br. s., 1H); LCMS ESI (M+H) 394; (M+Na) 416.5

Example 86

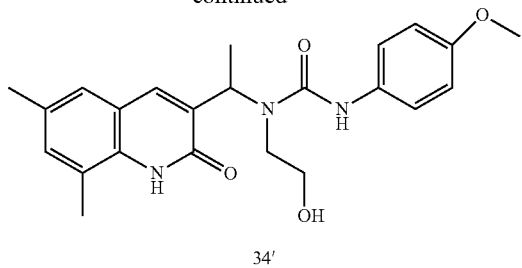

34'

(34'): 1-[1-(6,8-dimethyl-2-oxo-1H-quinolin-3-yl)ethyl]-1-(2-hydroxyethyl)-3-(4-methoxyphenyl)urea: To a suspension of compound 26' (25 mg, 0.096 mmol) in dioxane (1 mL) was added compound 33' (14 uL, 0.1 mmol). The reaction mixture was stirred at room temperature overnight. Solvent was removed and crude purified by silica gel column chromatography (ethyl acetate/hexanes gradient 0-90%) to give 7 mg of a white solid (18%).

1H NMR (500 MHz, DMSO-$d_6$) δ ppm 1.49 (d, J=7.14 Hz, 3H) 2.29 (s, 3H) 2.39 (s, 3H) 3.3-3.4 (m, 4H) 3.69 (s, 3H) 5.33 (q, J=6.77 Hz, 1H) 6.71-6.88 (m, 2H) 7.19 (s, 1H) 7.26 (d, J=8.78 Hz, 2H) 7.36 (s, 1H) 7.94 (s, 1H) 9.40 (br. s., 1H) 11.12 (br. s., 1H). LCMS ESI (M+H) 410

BIOLOGICAL EXAMPLES

The biological activity of the compounds of the present invention were tested using the test methods described below.

Successful drug candidate compounds were subjected to numerous biochemical and cellular assays. Purified bacterial β-glucuronidases were challenged with compounds to determine inhibition properties in a standard, robust activity assay, utilizing p-nitrophenyl glucuronide (PNPG) as the enzymatic substrate. Reactions (n=3/inhibitor concentration) were conducted in a 96-well assay, consisting of PNPG substrate (12 concentrations between 25 μM and 5 mM), inhibitor solution (8 concentrations between 0.1 nM and 100 μM), and 5 nM enzyme. Preferred compounds exhibited potent $IC_{50}$ values with values <1 μM.

Additionally, preferred compounds exhibited negligible, if any, effect on purified mammalian β-glucuronidases, specifically, preferred compounds are >500-fold more selective and potent against purified bacterial enzymes. Purified bovine liver and human β-glucuronidase were dissolved in a reaction mixture containing 1 μM enzyme and 1 mM PNPG as substrate.

Live, cultured bacterial cells (*E. coli, Bacteroides vulgatus, Clostridium ramosum*, as well as *Lactobacillus rauteri* and *Bifidobacterium infantis* as negative controls) mixed with the compounds (8 concentrations between 0.1 nM and 100 μM) may have reduced β-glucuronidase activity when challenged with 1 mM PNPG as a substrate. A potent inhibition profile was observed for the preferred compounds of the invention namely displaying EC50 values <500 nM.

Additionally, live cells were incubated with drug candidates (1 μM to 10 mM in half-log units) for extended time-points and plated on LB-Agar plates to conduct standard colony-forming assays. There was not an observable or quantifiable impact on cellular growth and viability after extended incubations of NCEs and cultured bacteria. As such, preferred compounds of the present invention did not exhibit anti-microbial characteristics. Furthermore, cultured mammalian cells (HCT116 cells) incubated (6 to 24 hr incubation time-points) with drug candidates continued to grow and be viable, as evidenced by the conversion of rezasurin to resorufin indicating mammalian cell viability. Critically, the compounds were not cytotoxic to mammalian cells.

In vivo efficacy of the compounds was determined in treated mouse models, developed by Symberix, Inc., Durham NC Efficacy was determined by reduction in bloody diarrhea (observed and scored) and reduced SN-38 levels in feces (determined bioanalytically). Compounds were given p.o. at 0.1 mg/kg to 1 mg/kg dose-strength and twice daily, to multiple cohorts of mice, including untreated, vehicle, inhibitor-only, and treated groups. Treatment were dosed at 50 mg/kg, unless otherwise noted. Compounds of the invention evidenced by a decrease in bloody diarrheal events in mice as well as diminished SN-38 levels in fecal matter, represented a reduction in bacterial β-glucuronidase activity due to inhibition.

Table 2 describes the compounds tested by the above described assay.

TABLE 2

| Reference No. | Compound Structure | FW | IC50 (μM) |
|---|---|---|---|
| Ref #6' | 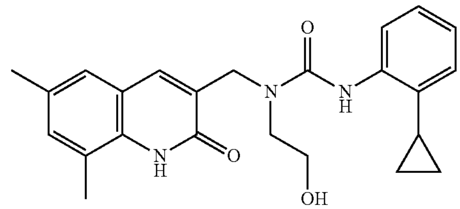 [SMILES: Cc1cc(C)c2[nH]c(=O)c(CN(CCO)C(=O)Nc3ccccc3C3CC3)cc2c1] | 405.49 | 0.759 |
| Ref #10' | 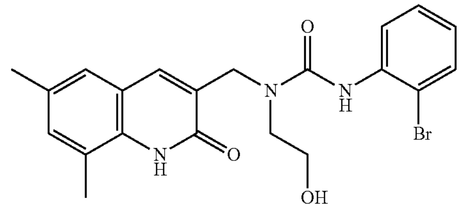 [SMILES: Cc1cc(C)c2[nH]c(=O)c(CN(CCO)C(=O)Nc3ccccc3Br)cc2c1] | 444.32 | 0.347 |

TABLE 2-continued

| Reference No. | Compound Structure | FW | IC50 (μM) |
|---|---|---|---|
| Ref #12' | 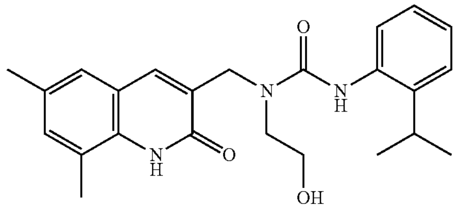 [SMILES: Cc1cc(C)c2[nH]c(=O)c(CN(CCO)C(=O)Nc3ccccc3C(C)C)cc2c1] | 407.5 | 0.468 |
| Ref #14' | 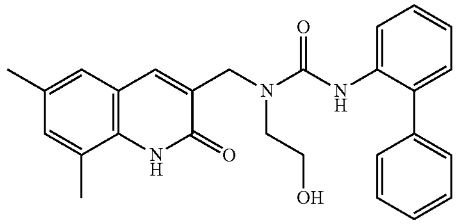 [SMILES: Cc1cc(C)c2[nH]c(=O)c(CN(CCO)C(=O)Nc3ccccc3-c3ccccc3)cc2c1] | 441.5 | 6.164 |
| Ref #18' | 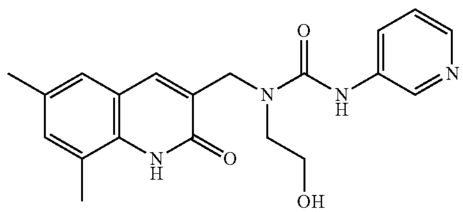 [SMILES: Cc1cc(C)c2[nH]c(=O)c(CN(CCO)C(=O)Nc3cccnc3)cc2c1] | 366.41 | >50 |
| Ref #20' | 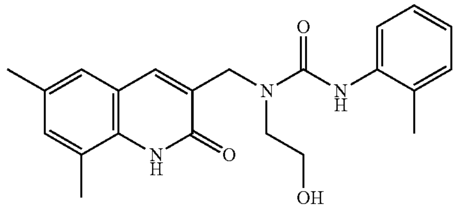 [SMILES: Cc1cc(C)c2[nH]c(=O)c(CN(CCO)C(=O)Nc3ccccc3C)cc2c1] | 491.3 | 0.118 |
| Ref #23' | 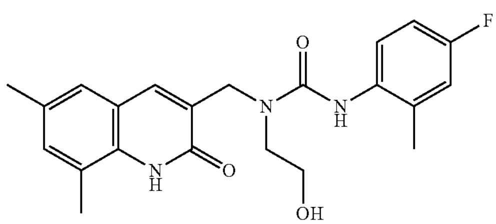 [SMILES: Cc1cc(C)c2[nH]c(=O)c(CN(CCO)C(=O)Nc3ccc(F)cc3C)cc2c1] | 509.31 | 0.1423 |
| Ref #29' | 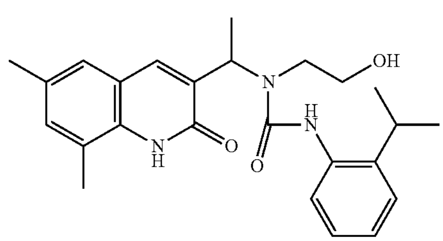 [SMILES: Cc1cc(C)c2[nH]c(=O)c(C(C)N(CCO)C(=O)Nc3ccccc3C(C)C)cc2c1] | 421.53 | 6.44 |

TABLE 2-continued

| Reference No. | Compound Structure | FW | IC50 (μM) |
|---|---|---|---|
| Ref #30' | 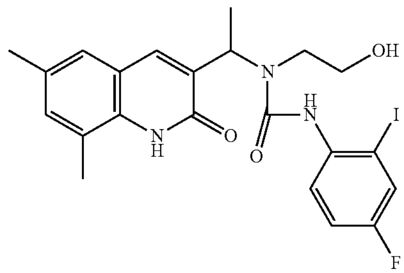 [SMILES: Cc1cc(C)c2[nH]c(=O)c(C(C)N(CCO)C(=O)Nc3ccc(F)cc3I)cc2c1] | 523.3 | 13.03 |
| Ref #31' | 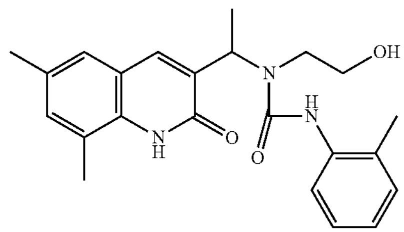 | 393.5 | >50 |
| Ref #34' | 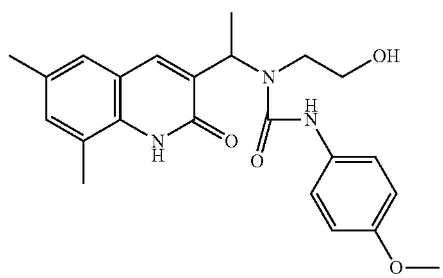 | 409.5 | >50 |
| Ref #36' | 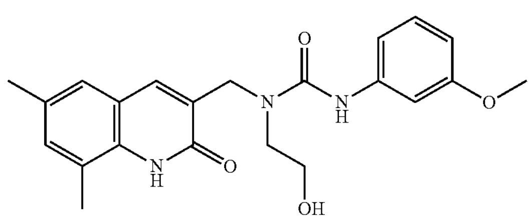 | 395.5 | 3.712 |
| Ref #38' | 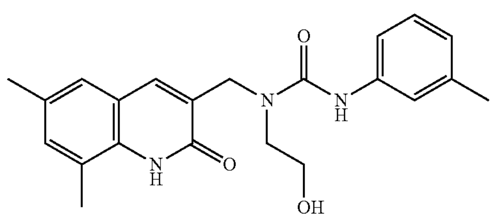 | 379.5 | 1.661 |
| Ref #41' | 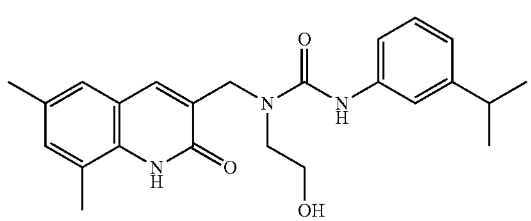 [SMILES: Cc1cc(C)c2[nH]c(=O)c(CN(CCO)C(=O)Nc3cccc(C(C)C)c3)cc2c1] | 407.5 | 6.731 |

TABLE 2-continued

| Reference No. | Compound Structure | FW | IC50 (µM) |
|---|---|---|---|
| Ref #44' | (structure) | 479.6 | 19.058 |
| Ref #45' | (structure) | 407.4 | 1.105 |
| Ref #14' | (structure) | 441.5 | 6.44 |

Table 3 describes data demonstrating the increased potency of inhibitor-glucuronides in the cellular assays described above with a 2 hour incubation time.

TABLE 3

2 hour incubation

| | Cell Based Inhibition IC$_{50}$ (nM) | |
|---|---|---|
| Compound Structure | Parent | Glucuronide |
| Inh1 | 890.0 | 8.8 |
| (structure) | 890.0 | 12.9 |
| (structure) | 100.0 | 2.0 |

Example A

The pharmacologic target of the present compounds is the β-glucuronidase enzyme (GUS) expressed by *Escherichia Coli* (*E. coli*). The *E. coli* GUS enzyme is one of three *E. coli* proteins involved in processing β-D-glucuronides, the broad class of glucuronides to which SN-38-glucuronide and most NSAID-glucuronides belong. The three *E. coli* proteins are encoded by the gusA, gusB and gusC genes. The product of gusA is the GUS (β-glucuronidase) enzyme, and the products of gusB and gusC are two membrane-associated transporter proteins that collectively mediate the uptake of β-D-glucuronides from outside to inside the bacterial cell. This uptake of β-D-glucuronides is active, meaning it is fueled by the electrochemical potential across the bacterial cell membranes. The bacterial-selective GUS inhibitor, Inhibitor-1 (Inh1), preferentially inhibits the subclass of bacterial GUS orthologs to which *E. coli* GUS belongs. Crystal structure of inhibitor-bound to *E. coli* GUS reveal that the hydroxylethyl moiety (highlighted in FIG. 1A) is the region of the molecule that is buried deepest in the enzyme binding site. This hydroxylethy moiety is also a glucuronidation site. We synthesized the Inh1-glucuronide (Inh-1G) shown in FIG. 1B to determine whether Inh-1G is an inhibitor or a substrate of *E. coli* GUS. The standard PNPG-PNP GUS cleavage assay was used to evaluate whether Inh1-G is an inhibitor of GUS purified from *E. coli* as well as GUS activity in live *E. coli*, and whether inhibition is dependent on incubation time with purified enzyme of in live cells. The time course of incubation between Inh1 & purified GUS, Inh1 & live cells, Inh1-G & purified GUS, and Inh1-G & live cells were one minute, 2 hours and 4 hours. The results are summarized in FIG. 2A. As expected, Inh1 inhibited the cleavage of PNPG to PNP in purified *E. coli* GUS and in live *E. coli* GUS with $IC_{50}$ values ranging from 1.9 to 0.75 µM. The $IC_{50}$ values for Inh1 remain relatively constant for both purified GUS and in live bacteria following inhibitor preincubation times ranging from one minute to four hours. Inh1-G also inhibited purified *E. coli* GUS with similar potency as Inh1. Inhibition of purified *E. coli* GUS by Inh1-G remained constant ($IC_{50}$~1 µM) over the 1-minute to 4-hour incubation period. In contrast the potency of Inh1-G increases by approximately 20-, 100- and 1000-fold following 1-min, 2-hr and 4-hr pre-incubation in live *E. coli*. After 4 hr incubation in live *E. coli*, the potency of Inh1-G increases by >1000-fold ($IC_{50}$ 1 nM). The time- and dose-dependent inhibition ($IC_{50}$) curves are shown in FIG. 3.

The time-dependent increase in Inh-1G potency in live *E. coli* may be due to active GUS transporter-mediated, accumulation of Inh-1G inside the cell by the gusB and gusC genes. If GUS is able to cleave Inh1-G, then the $IC_{50}$ should reach steady state. However, the $IC_{50}$ potencies of Inh1-G continues to strengthen with no signs of abatement even after four hours of incubation in live *E. coli*. To determine whether *E. coli* is able to cleave Inh1-G, the compounds of the present invention were subjected to an assay that can detect the liberation of free glucuronic acid (GA) from GUS-mediated cleavage of glucuronides by coupling the GUS reaction with a uronate dehydrogenase (UDH) reaction. Addition of UDH and nicotinamide adenine dinucleotide (NAD+) to a reaction solution containing free GA results in the catalysis of free GA to D-glucurate and the concomitant reduction of NAD+ to NADH. NADH can be detected photometrically by monitoring absorbance at 340 nm (FIG. 4). These findings indicate that *E. coli* GUS does not cleave Inh1-G (FIG. 5). Furthermore, none of the compounds in our GUSome library (which includes human and bovine GUS) can cleave Inh1-G. The present invention is believed to provide a novel and unique glucuronide that binds to (but cannot be cleaved by) GUS enzymes.

All publications, patents and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound selected from the group consisting of:
   [3-[[(4-ethoxyphenyl)carbamothioyl-(2-hydroxyethyl)amino]methyl]-6,8-dimethyl-2-oxo-1H-quinolin-7-yl]methyl acetate;
   1-[[6,8-dimethyl-7-[(4-methylpiperazin-1-yl)methyl]-2-oxo-1H-quinolin-3-yl]methyl]-3-(4-ethoxyphenyl)-1-(2-hydroxyethyl)thiourea;
   1-[[6,8-dimethyl-7-[(4-methylpiperazin-1-yl)methyl]-2-oxo-1H-quinolin-3-yl]methyl]-3-(4-ethoxyphenyl)-1-(2-hydroxyethyl)urea;
   1-[[7-(diethylaminomethyl)-6,8-dimethyl-2-oxo-1H-quinolin-3-yl]methyl]-3-(4-ethoxyphenyl)-1-(2-hydroxyethyl)thiourea;
   1-[[7-(diethylaminomethyl)-6,8-dimethyl-2-oxo-1H-quinolin-3-yl]methyl]-3-(4-ethoxyphenyl)-1-(2-hydroxyethyl)urea;
   tert-butyl-3-[[7-(diethylaminomethyl)-6,8-dimethyl-2-oxo-1H-quinolin-3-yl]methyl-[(4-ethoxyphenyl)carbamoyl]amino]pyrrolidine-1-carboxylate;
   1-[[7-(diethylaminomethyl)-6,8-dimethyl-2-oxo-1H-quinolin-3-yl]methyl]-3-(4-ethoxyphenyl)-1-pyrrolidin-3-yl-thiourea;
   1-[[7-(diethylaminomethyl)-6,8-dimethyl-2-oxo-1H-quinolin-3-yl]methyl]-3-(4-ethoxyphenyl)-1-pyrrolidin-3-yl-urea;
   tert-butyl 3-[[7-(diethylaminomethyl)-6,8-dimethyl-2-oxo-1H-quinolin-3-yl]methyl-[(4-ethoxyphenyl)carbamothioyl]amino]azetidine-1-carboxylate;
   tert-butyl 3-[[7-(diethylaminomethyl)-6,8-dimethyl-2-oxo-1H-quinolin-3-yl]methyl-[(4-ethoxyphenyl)carbamoyl]amino]azetidine-1-carboxylate;
   1-(azetidin-3-yl)-1-[[7-(diethylaminomethyl)-6,8-dimethyl-2-oxo-1H-quinolin-3-yl]methyl]-3-(4-ethoxyphenyl)thiourea;
   1-(azetidin-3-yl)-1-[[7-(diethylaminomethyl)-6,8-dimethyl-2-oxo-1H-quinolin-3-yl]methyl]-3-(4-ethoxyphenyl)urea;
   1-[[7-(diethylaminomethyl)-6,8-dimethyl-2-oxo-1H-quinolin-3-yl]methyl]-3-(4-ethoxyphenyl)-1-(3-hydroxycyclobutyl)thiourea;
   1-[[7-(diethylaminomethyl)-6,8-dimethyl-2-oxo-1H-quinolin-3-yl]methyl]-3-(4-ethoxyphenyl)-1-(3-hydroxycyclobutyl)urea;

1-[[6,8-dimethyl-7-(morpholinomethyl)-2-oxo-1H-quinolin-3-yl]methyl]-3-(4-ethoxyphenyl)-1-(2-hydroxyethyl)urea; and
1-[[6,8-dimethyl-7-(morpholinomethyl)-2-oxo-1H-quinolin-3-yl]methyl]-3-(4-ethoxyphenyl)-1-(2-hydroxyethyl)thiourea;
or a pharmaceutically acceptable salt thereof.
2. A compound selected from the group consisting of:
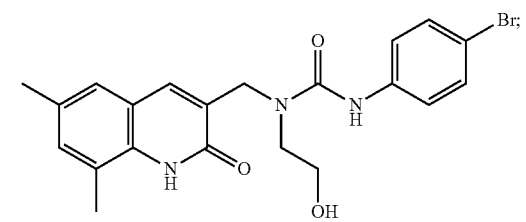
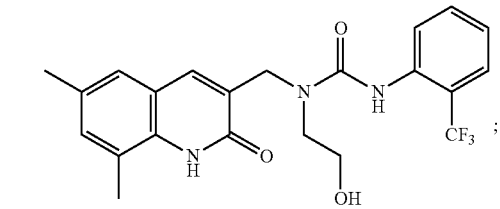
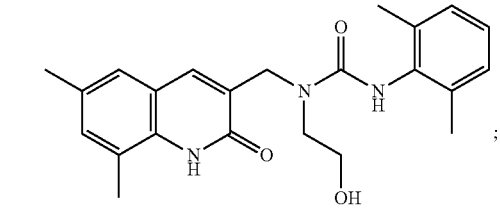
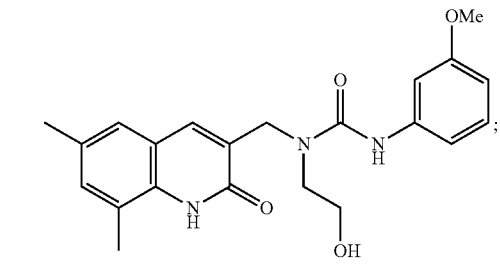
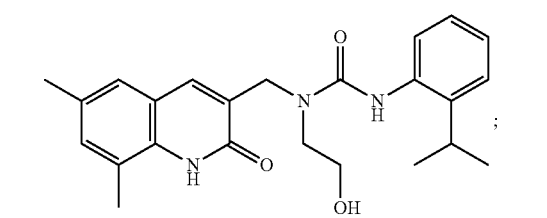
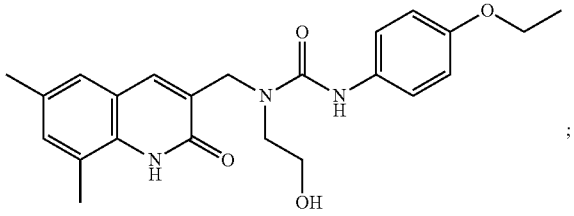
-continued
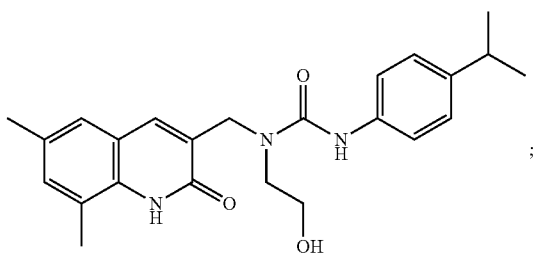
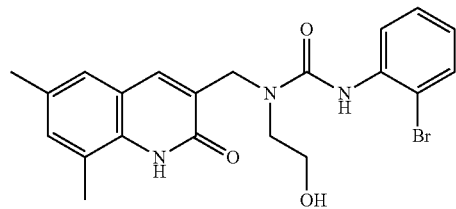
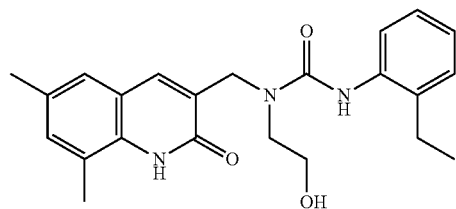
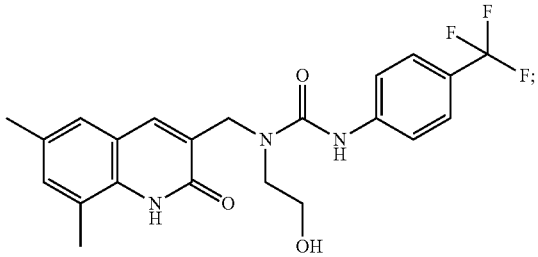
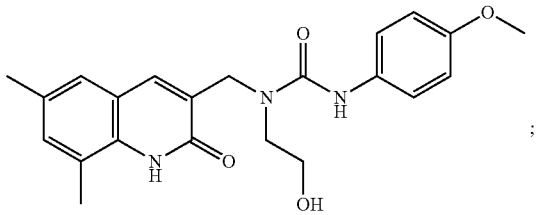
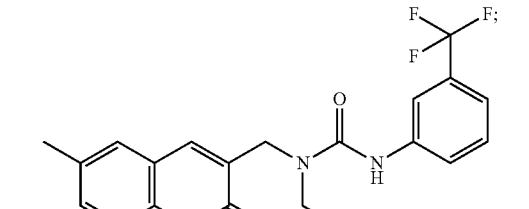
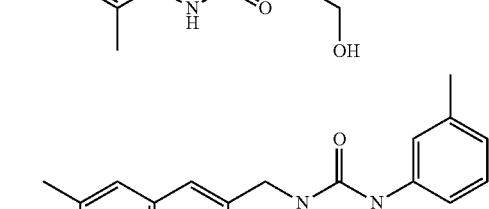
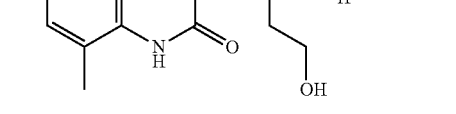

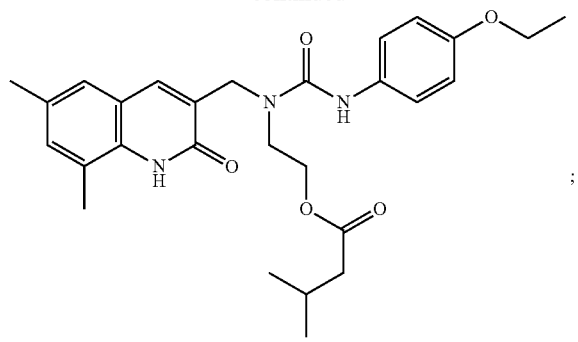
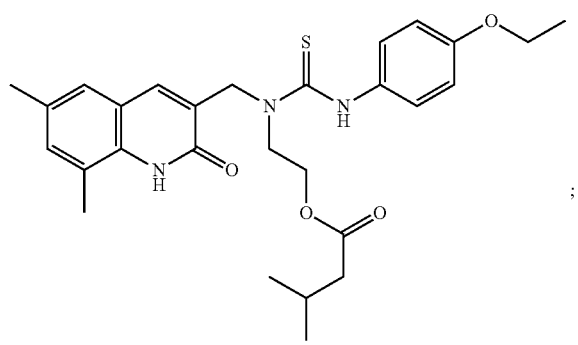
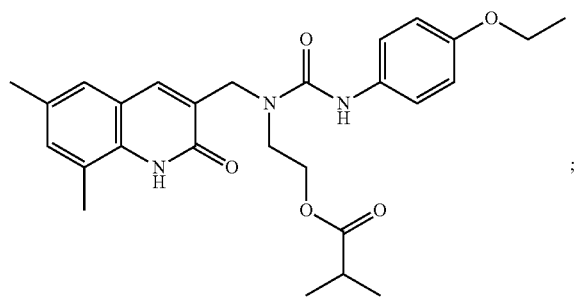
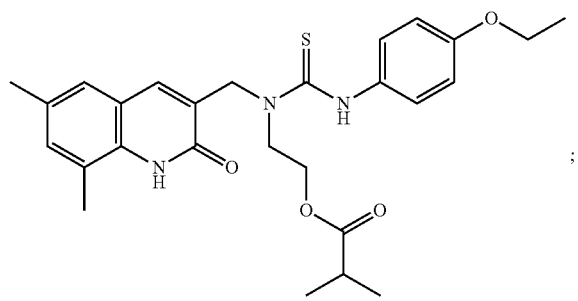
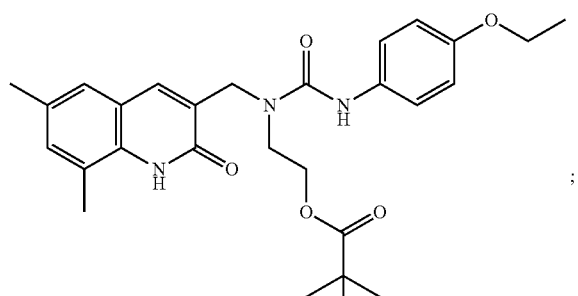
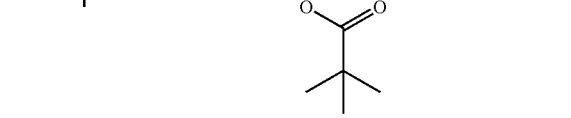
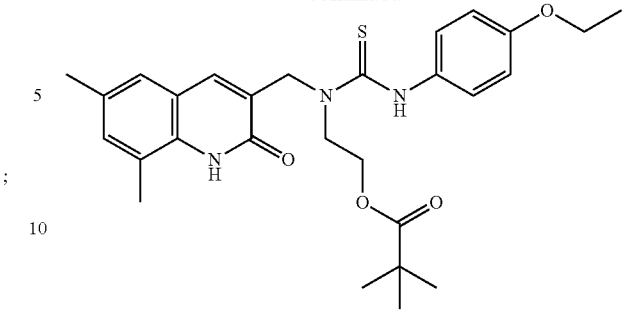
; and
or a pharmaceutically acceptable salt thereof.
3. A compound selected from the group consisting of:
3-(2-Bromophenyl)-1-[(6,8-dimethyl-2-oxo-1H-quinolin-3-yl)methyl]-1-(2-hydroxyethyl)urea;
1-[(6,8-dimethyl-2-oxo-1H-quinolin-3-yl)methyl]-1-(2-hydroxyethyl)-3-(2-isopropylphenyl)urea;
1-[(6,8-dimethyl-2-oxo-1H-quinolin-3-yl)methyl]-1-(2-hydroxyethyl)-3-(2-phenylphenyl)urea;

1-[(6,8-dimethyl-2-oxo-1H-quinolin-3-yl)methyl]-1-(2-hydroxyethyl)-3-(3-pyridyl)urea;
1-[(6,8-dimethyl-2-oxo-1H-quinolin-3-yl)methyl]-1-(2-hydroxyethyl)-3-(2-iodophenyl)urea;
1-[(6,8-dimethyl-2-oxo-1H-quinolin-3-yl)methyl]-3-(4-fluoro-2-iodo-phenyl)-1-(2-hydroxyethyl)urea;
1-[1-(6,8-dimethyl-2-oxo-1H-quinolin-3-yl)ethyl]-1-(2-hydroxyethyl)-3-(3-methoxyphenyl)urea;
1-[(6,8-dimethyl-2-oxo-1H-quinolin-3-yl)methyl]-1-(2-hydroxyethyl)-3-(m-tolyl)urea;
1-[(6,8-dimethyl-2-oxo-1H-quinolin-3-yl)methyl]-1-(2-hydroxyethyl)-3-(3-isopropylphenyl)urea;
1-[(6,8-dimethyl-2-oxo-1H-quinolin-3-yl)methyl]-1-(2-hydroxyethyl)-3-[4-methyl-2-(2-trimethylsilylethynyl)phenyl]urea;
1-[(6,8-dimethyl-2-oxo-1H-quinolin-3-yl)methyl]-3-(2-ethynyl-4-fluoro-phenyl)-1-(2-hydroxyethyl)urea;
1-[1-(6,8-dimethyl-2-oxo-1H-quinolin-3-yl)ethyl]-1-(2-hydroxyethyl)-3-(2-isopropylphenyl)urea;
1-[1-(6,8-dimethyl-2-oxo-1H-quinolin-3-yl)ethyl]-3-(4-fluoro-2-iodo-phenyl)-1-(2-hydroxyethyl)urea;
1-[1-(6,8-dimethyl-2-oxo-1H-quinolin-3-yl)ethyl]-1-(2-hydroxyethyl)-3-(o-tolyl)urea; and
1-[1-(6,8-dimethyl-2-oxo-1H-quinolin-3-yl)ethyl]-1-(2-hydroxyethyl)-3-(4-methoxyphenyl)urea;

or a pharmaceutically acceptable salt thereof.

4. A composition comprising one or more compounds of claim 1, and one or more pharmaceutically acceptable carriers.

5. A method for attenuating the side effects of drug induced diarrhea (DID) from one or more drugs, said method comprising: administering to a subject in need thereof an effective amount of one or more compounds of claim 1.

6. The method of claim 5, wherein the one or more compounds selectively inhibit β-glucuronidase.

7. The method of claim 5, wherein the one or more compounds can be co-administered with one or more therapeutic compounds or products.

8. A compound or a pharmaceutically acceptable salt thereof, having the structure:

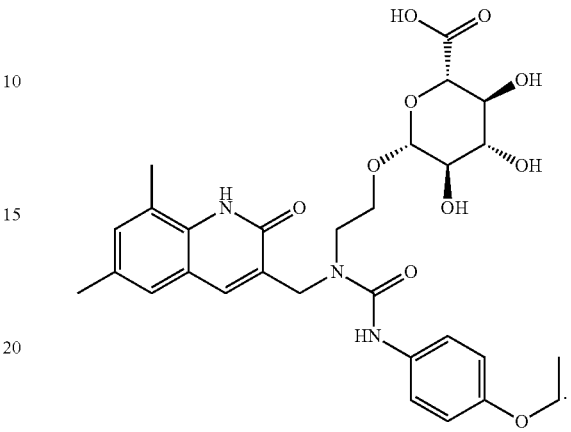

9. A composition comprising the compound of claim 8, and one or more pharmaceutically acceptable carriers.

10. A method for attenuating the side effects of drug induced diarrhea (DID) from one or more drugs, said method comprising: administering to a subject in need thereof an effective amount of the compound of claim 8.

11. The method of claim 10, wherein the one or more compounds selectively inhibit β-glucuronidase.

12. The method of claim 10, wherein the one or more compounds can be co-administered with one or more therapeutic compounds or products.

* * * * *